United States Patent
Yu et al.

(10) Patent No.: US 10,166,246 B2
(45) Date of Patent: Jan. 1, 2019

(54) TGR5 AGONIST COMPLEXES FOR TREATING DIABETES AND CANCER

(71) Applicant: City of Hope, Duarte, CA (US)

(72) Inventors: Donna Yu, Arcadia, CA (US); James Lester Figarola, West Covina, CA (US); Donald David, Northridge, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 15/312,157

(22) PCT Filed: May 26, 2015

(86) PCT No.: PCT/US2015/032404
§ 371 (c)(1),
(2) Date: Nov. 17, 2016

(87) PCT Pub. No.: WO2015/183794
PCT Pub. Date: Dec. 3, 2015

(65) Prior Publication Data
US 2017/0196890 A1      Jul. 13, 2017

Related U.S. Application Data

(60) Provisional application No. 62/003,140, filed on May 27, 2014.

(51) Int. Cl.
| | | |
|---|---|---|
| A61K 31/575 | (2006.01) | |
| A61K 31/155 | (2006.01) | |
| C07C 279/26 | (2006.01) | |
| C07J 9/00 | (2006.01) | |
| C07J 41/00 | (2006.01) | |

(Continued)

(52) U.S. Cl.
CPC .......... A61K 31/575 (2013.01); A61K 31/155 (2013.01); A61K 31/19 (2013.01); C07C 279/26 (2013.01); C07J 9/005 (2013.01); C07J 41/0061 (2013.01); C07J 63/008 (2013.01)

(58) Field of Classification Search
None
See application file for complete search history.

(56) References Cited

U.S. PATENT DOCUMENTS

| | | |
|---|---|---|
| 4,080,472 A | 3/1978 | Bohuon |
| 4,861,760 A | 8/1989 | Mazuel et al. |

(Continued)

FOREIGN PATENT DOCUMENTS

| | | | |
|---|---|---|---|
| CN | 101691344 | | 4/2010 |
| FR | 2796551 | * | 1/2001 |

(Continued)

OTHER PUBLICATIONS

Belcher, G. et al. (Oct. 2005). "Safety and tolerability of pioglitazone, metformin, and gliclazide in the treatment of type 2 diabetes," *Diabetes Res. Clin. Pract.* 70(1): 53-62.

(Continued)

*Primary Examiner* — Karl J Puttlitz
(74) *Attorney, Agent, or Firm* — Mintz Levin Cohn Ferris Glovsky and Popeo, P.C.

(57) ABSTRACT

Provided herein are complexes of metformin or metformin analogues and a TGR5 ligand that are useful in treating diseases including diabetes, cardiovascular disease, and cancer.

7 Claims, 12 Drawing Sheets

(1): $R^1 = OH, R^2 = H, R^7 = OH, R^5 = H, R^{11} = H$.
(2): $R^1 = OH, R^2 = H, R^7 = H, R^5 = Et, R^{11} = H$.
(3): $R^1 = H, R^2 = OH, R^7 = H, R^5 = Et, R^{11} = H$.
(4): $R^1 = H, R^2 = OH, R^7 = H, R^5 = H, R^{11} = H$.
(5): $R^1 = H, R^2 = H, R^7 = H, R^5 = H, R^{11} = H$.
(6): $R^1 = OH, R^2 = H, R^7 = H, R^5 = H, R^{11} = CH_3$
(7): $R^1 = H, R^2 = H, R^7 = H, R^5 = H, R^{11} = CH_3$
(8): $R^1 = H, R^2 = OH, R^7 = H, R^5 = H, R^{11} = CH_3$

(51) Int. Cl.
*C07J 63/00* (2006.01)
*A61K 31/19* (2006.01)

(56) References Cited

U.S. PATENT DOCUMENTS

| | | | |
|---|---|---|---|
| 4,911,920 | A | 3/1990 | Jani et al. |
| 5,212,162 | A | 5/1993 | Missel et al. |
| 5,403,841 | A | 4/1995 | Lang et al. |
| 5,955,106 | A | 9/1999 | Moeckel et al. |
| 6,031,004 | A | 2/2000 | Timmins et al. |
| 6,676,966 | B1 | 1/2004 | Odidi et al. |
| 8,703,183 | B2 | 4/2014 | Lara |
| 2005/0101565 | A1 | 5/2005 | Dasseaux |
| 2005/0182029 | A1 | 8/2005 | Lal |
| 2011/0021634 | A1 | 1/2011 | Patel et al. |
| 2011/0171142 | A1 | 7/2011 | Lara |
| 2011/0257432 | A1 | 10/2011 | DiMauro |
| 2012/0202849 | A1 | 8/2012 | Pareek |
| 2012/0219623 | A1 | 8/2012 | Meinicke |
| 2012/0220664 | A1 | 8/2012 | Struhl et al. |
| 2014/0018308 | A1 | 1/2014 | Brown et al. |
| 2017/0037043 | A1* | 2/2017 | Liu .................. A61K 31/4375 |

FOREIGN PATENT DOCUMENTS

| | | | |
|---|---|---|---|
| FR | 2796551 | A1 | 1/2001 |
| FR | 2796551 | B1 | 1/2001 |
| IN | 2468/DEL/2011 | * | 1/2013 |
| IN | DEL-2011-02468 | | 3/2013 |
| WO | WO-99/40904 | A2 | 8/1999 |
| WO | WO-99/40904 | A3 | 8/1999 |
| WO | WO-2002/012177 | A1 | 2/2002 |
| WO | WO-2002/080971 | A1 | 10/2002 |
| WO | WO-2004/110422 | A1 | 12/2004 |
| WO | WO-2008/112166 | A2 | 9/2008 |
| WO | WO-2008/112166 | A3 | 9/2008 |
| WO | WO-2013/188452 | A1 | 12/2013 |
| WO | WO-2014/006093 | A1 | 1/2014 |

OTHER PUBLICATIONS

Ben Sahra I. et al. (May 2010, e-published May 4, 2010). "Metformin in cancer therapy: a new perspective for an old antidiabetic drug?" *Mol Cancer Ther* 9(5):1092-1099.

Davidson, M. B. et al. (Jan. 1997). "An overview of metformin in the treatment of type 2 diabetes mellitus," *Am. J. Med.* 102(1):99-110.

Forman, B. M. et al. (1995). "Identification of a nuclear receptor that is activated by farnesol metabolites," *Cell* 81(5): 687-693.

Ganie M.A. et al. (Sep. 2013, e-published Jul. 11, 2013). "Improved efficacy of low-dose spironolactone and metformin combination than either drug alone in the management of women with polycystic ovary syndrome (PCOS): a six-month, open-label randomized study," *J. Clin. Endocrinol. Metat.* 98(9):3599-3607.

Genet, C. et al. (Jan. 14, 2010). "Structure-activity relationship study of betulinic acid, a novel and selective TGR5 agonist, and its synthetic derivatives: potential impact in diabetes," *J. Med. Chem.* 53(1):178-190.

Gordon, G. S. et al. (Nov. 1985). "Nasal absorption of insulin: enhancement by hydrophobic bile salts," *Proc. Natl. Acad. Sci. USA* 82(21):7419-7423.

International Search Report dated Aug. 5, 2015, for PCT Application No. PCT/US2015/032404, filed May 26, 2015, 4 pages.

Kappe, C. et al. (Mar. 2013, e-published Aug. 2, 2012). "Metformin protects against lipoapoptosis and enhances GLP-1 secretion from GLP-1-producing cells," *J Gastroenterol*. 48:322-332.

Katsuma, S. et al. (Apr. 2005). "Bile acids promote glucagon-like peptide-1 secretion through TGR5 in a murine enteroendocrine cell line STC-1," *Biochem Biophys Res Commun* 329(1):386-390.

Keitel, V. et al. (Jul. 18, 2008, e-published May 9, 2008). Expression and function of the bile acid receptor TGR5 in Kupffer cell, *Biochem. Biophys. Res. Commun.* 372(1):78-84.

Maruyama, T. et al. (Nov. 15, 2002). "Identification of membrane-type receptor for bile acids (M-BAR)," *Biochem. Biophys. Res. Commun.* 298(5):714-719.

Porez, G. et al. (Sep. 2012, e-published May 1, 2012). "Bile acid receptors as targets for the treatment of dyslipidemia and cardiovascular disease," *J Lipid Res.* 53(9):1723-1737.

Posa, M. et al. (Aug. 7, 2008, e-published May 9, 2008). "Formation of hydrogen-bonded complexes between bile acids and lidocaine in the lidocaine transfer from an aqueous phase to chloroform," *Eur J Pharm Sci* 34(4-5):281-292.

Proctor, W. R. et al. (Aug. 2008, e-published May 5, 2008). "Mechanisms underlying saturable intestinal absorption of metformin," *Drug Metab. Dispos.* 36(8):1650-1658.

Sato, H. et al. (Mar. 27, 2008, e-published Feb. 29, 2008). Novel potent and selective bile acid derivatives as TGR5 agonists: biological screening, structure-activity relationships, and molecular modeling studies, *J. Med. Chem.* 51(6):1831-1841.

Stratton, I. M. et al. (Aug. 2000). "Association of glycaemia with macrovascular and microvascular complications of type 2 diabetes (UKPDS 35): prospective observational study," *BMJ* 321(7258):405-412.

Thomas, C. et al. (Aug. 2008). "Targeting bile-acid signalling for metabolic diseases," *Nature Reviews Drug Discovery* 7(8):678-693.

Thomas, C. et al. (Sep. 2009). "TGR5-mediated bile acid sensing controls glucose homeostasis," *Cell Metab.* 10(3):167-177.

Tiwari, A. et al. (May 2009, e-published Feb. 25, 2009). "TGR5: an emerging bile acid G-protein-coupled receptor target for the potential treatment of metabolic disorders," *Drug Discovery Today* 14(9-10):523-530.

Tucker, G. T. et al. (Aug. 1981). "Metformin kinetics in healthy subjects and in patients with diabetes mellitus," *Br. J. Clin. Pharmacol.* 12(2): 235-246.

Wahdan-Alaswad, R. et al. (Dec. 15, 2013, e-published Oct. 3, 2013). "Glucose promotes breast cancer aggression and reduces metformin efficacy," *Cell Cycle* 12(24):3759-3769.

Wang, H. et al. (May 1999). "Endogenous bile acids are ligands for the nuclear receptor FXR/BAR," *Mol. Cell* 3(5): 543-553.

Woo, L.C. et al. (Sep. 1999). "Vanadyl-biguanide complexes as potential synergistic insulin mimics," *J. Inorg. Biochem.* 76(3-4):251-257.

Written Opinion dated Aug. 5, 2015, for PCT Application No. PCT/US2015/032404, filed May 26, 2015, 10 pages.

Yu, D. et al. (Nov. 2012, e-published Sep. 21, 2012). "An improved synthesis of 6α-ethylchenodeoxycholic acid (6ECDCA), a potent and selective agonist for the Farnesoid X Receptor (FXR)," *Steroids* 77(13):1335-1338.

* cited by examiner

FIG. 1

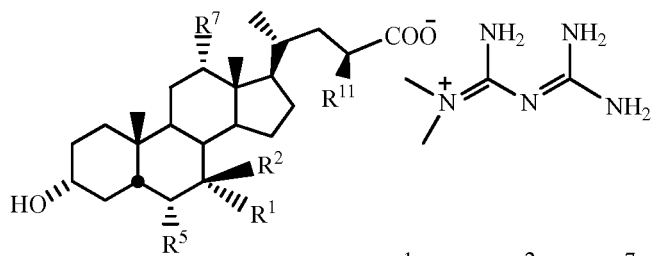

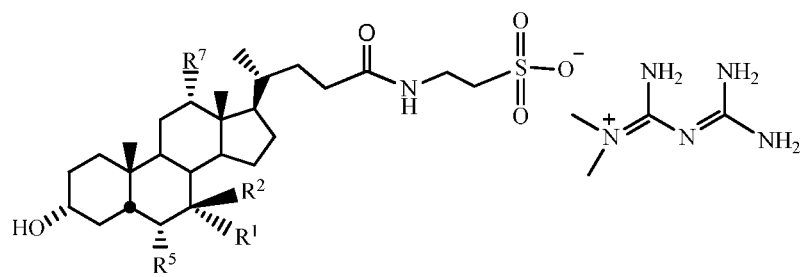

(1): $R^1$ = OH, $R^2$ = H, $R^7$ = OH, $R^5$ = H.
(2): $R^1$ = OH, $R^2$ = OH, $R^7$ = H, $R^5$ = H.
(3): $R^1$ = OH, $R^2$ = H, $R^7$ = OH, $R^5$ = H.
(4): $R^1$ = H, $R^2$ = H, $R^7$ = H, $R^5$ = H.
(5): $R^1$ = H, $R^2$ = H, $R^7$ = OH, $R^5$ = H.

(1): $R^1 = OH, R^2 = H, R^7 = OH, R^5 = H.$
(2): $R^1 = OH, R^2 = OH, R^7 = H, R^5 = H.$
(3): $R^1 = OH, R^2 = H, R^7 = OH, R^5 = H.$
(4): $R^1 = H, R^2 = H, R^7 = H, R^5 = H.$
(5): $R^1 = H, R^2 = H, R^7 = OH, R^5 = H.$ oleanolic acid    betulinic acid    ursolic acid

FIG. 6
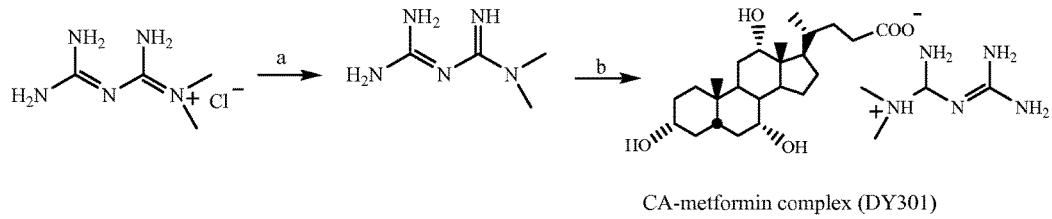
CA-metformin complex (DY301)
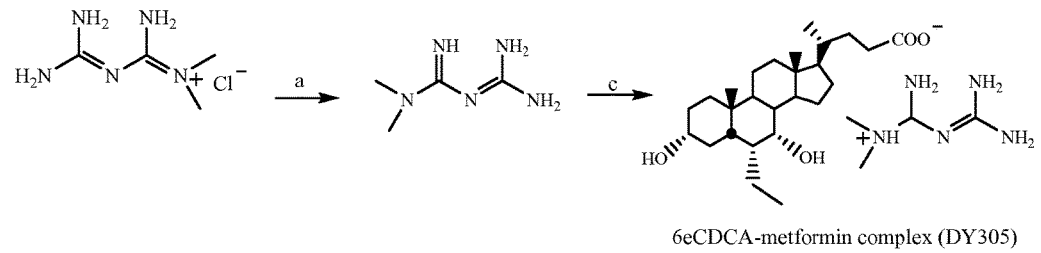
6eCDCA-metformin complex (DY305)
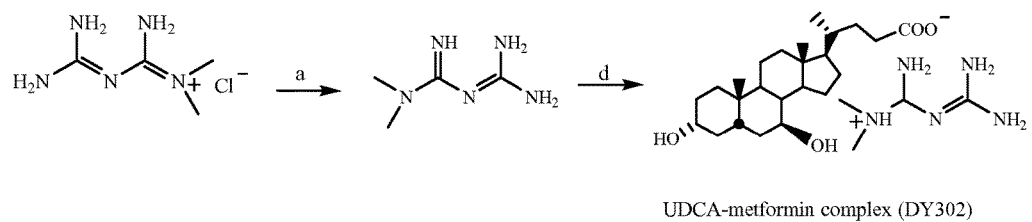
UDCA-metformin complex (DY302)
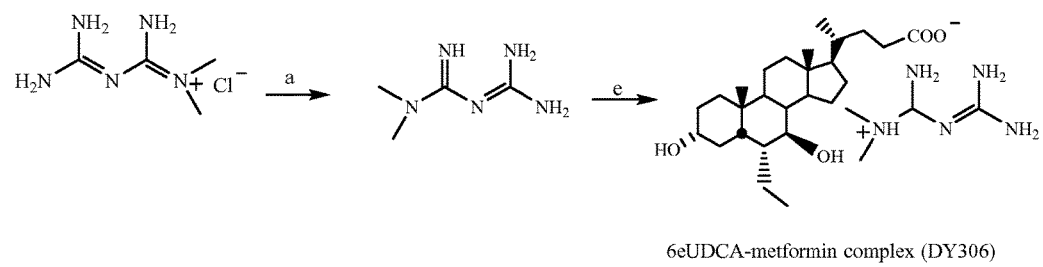
6eUDCA-metformin complex (DY306)

TGR5 AGONIST COMPLEXES FOR TREATING DIABETES AND CANCER

CROSS-REFERENCES TO RELATED APPLICATIONS

This application claims priority to U.S. Provisional Application No. 62/003,140, filed May 27, 2014, the content of which is incorporated herein by reference in its entirety and for all purposes.

BACKGROUND OF THE INVENTION

Diabetes mellitus is a major health epidemic categorized into two subclasses: type 1, known as insulin dependent diabetes mellitus (IDDM), and type 2, noninsulin dependent diabetes mellitus (NIDDM).[1] Type 2 diabetes is a chronic and progressive metabolic disorder of carbohydrate and lipid metabolism and accounts for nearly 90% of diabetes mellitus and results from impaired insulin secretion and reduced peripheral insulin sensitivity—a burgeoning, worldwide health problem affecting almost twenty-six million people in the United States.[2] Current oral therapies for this disease are limited by availability of effective medications, including, for example, insulin secretagogues, such as sulfonylureas; activators of the peroxisome proliferator-activated receptor-γ ("PPAR-γ") such as the thiazolidinediones; and effectors of glucose-lowering, exemplified by metformin and its analogues. All of the existing oral hypoglycemic agents have subsequent failure after long term administration. Deficiencies associated with currently available treatments include hypoglycemic episodes, weight gain, gastrointestinal problems, edema, and loss of responsiveness over time.

Metformin is a commonly used medication in the treatment of diabetes. Recent interest in metformin as a potential anticancer agent has sparked studies suggesting cancer patients with or without diabetes may benefit in lowering insulin levels. The currently marketed metformin hydrochloride salt was approved by the United States Food and Drug Administration (FDA) in 1995 as an oral hypoglycemic agent. Given alone or in combination with a sulfonylurea and insulin, metformin reduces hyperglycemia through decreased hepatic glucose output and enhanced glucose uptake by skeletal muscle. However, metformin HCl has poor oral bioavailability (only about 50%) because of its poor absorption from lower gastrointestinal tract. Thus there is a need in the art to develop new therapies for diabetes and cancer as well as a need to develop compositions having greater bioavailability to patients suffering from diabetes and its associated diseases, and cancer. Provided herein are solutions to these and other problems in the art.

BRIEF SUMMARY OF THE INVENTION

Provided herein, inter alia, are complexes useful for treating diabetes, polycystic ovary syndrome, cardiovascular disease, fatty liver disease and cancer.

The complexes described herein include metformin or metformin analogue and a TGR5 ligand. In one aspect is a complex that includes a metformin or metformin analogue non-covalently bound to a TGR5 ligand. In another aspect is a complex between a metformin or metformin analogue and a TGR5 ligand, wherein the TGR5 ligand is non-covalently bound to the metformin or metformin analogue.

Also provided herein are pharmaceutical compositions. In one aspect, is a pharmaceutical composition including a metformin or a metformin analogue, a TGR5 ligand, and a pharmaceutically acceptable excipient.

Methods of treating cancer are provided herein. In one aspect, is a method of treating cancer by administering to a subject in need thereof a combined therapeutically effective amount of a metformin or metformin analogue and a TGR5 ligand as described herein.

Methods of treating diabetes and its associated diseases are included herein. In one aspect is a method of treating diabetes in a subject in need thereof by administering a combined therapeutically effective amount of a metformin or metformin analogue and a TGR5 ligand as described herein. In another aspect is a method of treating a metabolic disease associated with diabetes in a subject in need thereof by administering a combined therapeutically effective amount of a metformin or metformin analogue and a TGR5 ligand as described herein. In another aspect is a method of treating hyperglycemia, insulin resistance, hyperinsulinemia, dyslipidemia, hypertriglyceridemia, hypertension, fibrinolysis, or endothelial dysfunction by administering a combined therapeutically effective amount of a metformin or metformin analogue and a TGR5 ligand as described herein. In yet another aspect is a method of reducing blood pressure by administering a combined therapeutically effective amount of a metformin or metformin analogue and a TGR5 ligand as described herein. In another aspect is a method of decreasing glycated hemoglobin (HbA1c) by administering a combined therapeutically effective amount of a metformin or metformin analogue and a TGR5 ligand as described herein. In another aspect is a method of reducing liver weight or reducing kidney weight by administering a combined therapeutically effective amount of a metformin or metformin analogue and a TGR5 ligand as described herein.

Also provided herein are methods for treating cardiovascular disease. In one aspect is a method for treating cardiovascular disease in a subject in need thereof by administering a combined therapeutically effective amount of a metformin or metformin analogue and a TGR5 ligand as described herein.

Methods for treating polycystic ovary syndrome are also provided herein. In one aspect is a method for treating polycystic ovary syndrome in a subject in need thereof by administering a combined therapeutically effective amount of a metformin or metformin analogue and a TGR5 ligand as described herein.

BRIEF DESCRIPTION OF THE DRAWINGS

FIG. 1 Chemical structures of exemplary metformin-based bile acid complexes.

FIG. 2 Chemical structures of exemplary metformin-based bile acid tauro-form complexes.

FIG. 6 Synthesis of TGR5 agonist-metformin complexes, reaction conditions; (a) NaOH/EtOH; (b) CA, (c) UDCA, (d) 6eCDCA, (e) 6eUDCA, and EtOH, 50° C., 12 h.

FIG. 7A: DY301 and LCA; FIG. 7F: DY301 and CA.

DETAILED DESCRIPTION OF THE INVENTION

Figure 3:
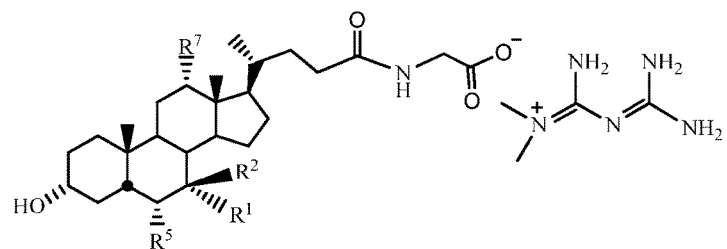
FIG. 3 Chemical structures of exemplary metfornin-based bile acid glycol form complexes.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention.

The following definitions are provided to facilitate understanding of certain terms used frequently herein and are not meant to limit the scope of the present disclosure.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds (e.g. alkene, alkyne). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. Heteroalkyl is not cyclized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—OCH$_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—OCH$_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Cycloalkyl and heterocycloalkyl are non-aromatic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR'"NR'"R"", —CN, —NO$_2$, monophosphate (or derivatives thereof), diphosphate (or derivatives thereof), triphosphate (or derivatives thereof), in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR'"NR'"R"", —CN, —NO$_2$, —R', —N$_3$, —CH(Ph)$_2$, fluoro(C$_1$-C$_4$)alkoxy, and fluoro(C$_1$-C$_4$)alkyl, monophosphate (or derivatives thereof), diphosphate (or derivatives thereof), triphosphate (or derivatives thereof), in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In embodiments, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U-, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (B) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (ii) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (b) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), and triphosphate (or derivatives thereof).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth in the Examples section below.

The term "pharmaceutically acceptable salts" is meant to include salts of active compounds or complexes prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Thus, in embodiments, contacting basic metformin with acidic TGR5 ligands herein may result in forming a salt. In embodiments, salts of metformin or metformin analogues, or salts of TGR5 ligands described herein, when contacted with a sufficient amount of base or acid, may yield a salt or salt complex. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds and complexes of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (-)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in a conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the complexes of the present invention by chemical or biochemical methods in an ex vivo environment. For example, prodrugs can be slowly converted to the compounds of the present invention when placed in a transdermal patch reservoir with a suitable enzyme or chemical reagent. In embodiments, prodrug moieties described in Murakami et al. J. Med Chem., 2011, 54, 5902; Sofia et al., J. Med Chem. 2010, 53, 7202; Lam et al. ACC, 2010, 54, 3187; Chang et al., ACS Med Chem Lett., 2011, 2, 130; Furman et al., Antiviral Res., 2011, 91, 120; Vernachio et al., ACC, 2011, 55, 1843; Zhou et al, AAC, 2011, 44, 76; Reddy et al., BMCL, 2010, 20, 7376; Lam et al., J. Virol., 2011, 85, 12334; Sofia et al., J. Med. Chem., 2012, 55, 2481, Hecker et al., J. Med. Chem., 2008, 51, 2328; or Rautio et al., Nature Rev. Drug. Discov., 2008, 7, 255, all of which are incorporated herein by reference in their entirety for all purposes, may be added to compounds described herein or used in methods described herein.

Certain complexes and compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus, a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13}$A, $R^{13B}$, $R^{13C}$, $R^{13D}$, etc. is defined within the scope of the definition of $R^{13}$ and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

"Analog," "analogue," or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analogue is a compound that is similar or comparable in function and appearance but not in structure or origin to a reference compound.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, electrocardiogram, echocardiography, radio-imaging, nuclear scan, and/or stress testing, neuropsychiatric exams, and/or a psychiatric evaluation. For example, certain methods herein treat diabetes, its associated diseases, cancer, or cardiovascular disease. In embodiments, certain methods herein treat diabetes by decreasing, for example, glucose levels, insulin resistance, hypertriglyceridemia, or hyperinsulinemia. In embodiments, certain methods herein treat cancer, where the cancer may be associated with hyperinsulinemia. In embodiments, certain methods herein treat cardiovascular disease by, for example, decreasing hypertension (i.e. by lowering diastolic or systolic blood pressure), atherosclerosis, atherothrombosis, or the incidence of coronary heart disease or myocardial infarction, or by increasing cardiac performance, improving exercise tolerance, preventing heart failure, increasing blood oxygen content, or improving respiratory function. The term "treating" and conjugations thereof, include prevention of an injury, pathology, condition, or disease.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In embodiments, a patient is human.

"Disease" or "condition" refer to a state of being or health status of a patient or subject capable of being treated with a compound, pharmaceutical composition, or method provided herein. In embodiments, the disease is diabetes. In embodiments, the disease is a disease associated with diabetes. In embodiments, the disease is a cancer. In embodiments, the disease is cardiovascular disease.

The term "associated" or "associated with" in the context of a substance or substance activity or function associated with a disease (e.g. a protein associated disease, a symptom associated with cancer, diabetes, or cardiovascular disease) means that the disease is caused or characterized by (in whole or in part), or a symptom of the disease is caused or characterized by (in whole or in part) the substance or substance activity or function. For example, a symptom of a disease or condition associated with an increased glucose levels or insulin resistance. As used herein, what is described as being associated with a disease, if a causative or characterizing agent, could be a target for treatment of the disease. For example, a disease associated with diabetes, may be treated with an agent (e.g. complex as described herein) effective for decreasing, for example, glucose levels in a patient.

The term "diabetes" as used herein refers to onset and inducement of diabetes mellitus in any manner and includes type 1, type 2, gestational, steroid-induced, HIV treatment induced and autoimmune diabetes. Diabetes is recognized as a complex, chronic disease in which 60% to 70% of all case fatalities among diabetic patients are a result of cardiovascular complications. Diabetes is not only considered a coronary heart disease risk equivalent but is also identified as an independent predictor of adverse events, including recurrent myocardial infarction, congestive heart failure, and death following a cardiovascular incident. The adoption of tighter glucose control and aggressive treatment for cardiovascular risk factors would be expected to reduce the risk of coronary heart disease complications and improve overall survival among diabetic patients. Yet, diabetic patients are two to three times more likely to experience an acute myocardial infarction than non-diabetic patients, and diabetic patients live eight to thirteen years less than non-diabetic patients.

As used herein, the term "cancer" refers to all types of cancer, neoplasm, or malignant or benign tumors found in mammals, including leukemia, carcinomas and sarcomas. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding- Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

"Cancer model organism", as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

As used herein, "cardiovascular disease" refers to diseases associated with the heart, blood vessels or both. Cardiovascular diseases include, but are not limited to, coronary heart disease, cardiomyopathy, hypertensive heart disease, heart failure, cardiac dysrhythmias, inflammatory heart disease, peripheral arterial disease, cerebrovascular disease and inflammatory heart disease.

As used herein, the term "polycystic ovary syndrome" or "PCOS" refers to endocrine disorders and associated diseases thereof characterized by menstrual irregularity. Clinical manifestations of PCOS include, but are not limited to, hormonal imbalance, hyperandrogenism, amenorrhea, acanthosis nigricans, acne, obesity, hirsutism, alopecia, and female infertility.

As used herein, the term "administering" refers to oral administration (i.e. solid or liquid), administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. cardiovascular therapies, diabetes therapies, cancer therapies or another complex described herein).

The compounds and complexes described herein can be used in combination with one another, with other active agents known to be useful in treating a disease (e.g. anti-cancer agents, anti-diabetes agents, or cardiovascular therapy agents) or with adjunctive agents that may not be effective alone, but may contribute to the efficacy of the active agent.

In embodiments, co-administration includes administering one active agent (e.g. a complex described herein) within 0.5, 1, 2, 4, 6, 8, 10, 12, 16, 20, or 24 hours of a second active agent (e.g. anti-cancer agents, anti-diabetes agents, or cardiovascular therapy agents). Also contemplated herein, are embodiments, where co-administration includes administering one active agent (e.g. metformin) within 0.5, 1, 2, 4, 6, 8, 10, 12, 16, 20, or 24 hours of a second active agent (e.g. TGR5 ligand). Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In other embodiments, the active agents can be formulated separately. In embodiments, the active and/or adjunctive agents may be linked or conjugated to one another. In embodiments, the compounds and complexes described herein may be combined with treatments for cancer such as chemotherapy or radiation therapy.

A "cardiovascular therapy agent" refers to a composition that treats cardiovascular disease or its associated disease. Exemplary cardiovascular therapy agents include, for example, Angiotensin Converting Enzyme Inhibitors (e.g. Enalipril, Lisinopril), Angiotensin Receptor Blockers (e.g. Losartan, Valsartan), Beta Blockers (e.g. Lopressor, TOPROL-XL®), Digoxin, Diuretics (e.g. LASIX®), or combinations thereof. Likewise, a "blood pressure lowering agent" refers to compositions that treat high blood pressure. Exemplary blood pressure lowering agents include, for example, diuretics, beta blockers, ACE inhibitors, Angiotensin II receptor blockers, calcium channel blockers, alpha blockers, vasodilators, or a combination thereof.

An "anti-diabetes agent" refers to a composition that treats diabetes or a disease associated with diabetes. Exemplary anti-diabetes agents include biguanides (e.g. metformin), thiazolidinediones (e.g. pioglitazone, rosiglitazone, troglitazone), sulfonylureas (e.g. tolbutamide, acetohexamide, chlorpropamide, glipizide, glyburide, glibenclamide), non-sulfonylurea secretagogues (e.g. meglitinides such as repaglinide, nateglinide), alpha-glucosidase inhibitors (e.g. acarbose, miglitol, voglibose), incretin mimetics (e.g. exenatide, liraglutide, taspoglutide, lixisenatide), amylin analogues, glycosurics (e.g. canagliflozin, dapagliflozin), dipeptidyl peptidase-4 inhibitor (e.g. sitagliptin, saxagliptin, vildagliptin, linagliptin, alogliptin, septagliptin), or a meglitinide (e.g. repaglinide).

An "anti-PCOS agent" or "anti-polycystic ovary syndrome agent" refers to a composition that treats polycystic ovary syndrome or a disease associated with polycystic ovary syndrome. Exemplary anti-PCOS agents include spironolactone, finasteride, progesterone, medroxyprogesterone, estradiol (e.g. ethinyl estradiol), levonorgestrel, elfornithine, clomiphen, and gonadotropins (e.g. luteinizing hormone and follicle-stimulating hormone).

An "anti-cancer agent" used in accordance with its plain ordinary meaning and refers to a composition (e.g. a compound, polypeptide, amino acid, polynucleotide, nucleic acid, or antibody) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Anti-cancer agents may be selective for certain cancers or certain tissues.

"Chemotherapeutic" or "chemotherapeutic agent" is used in accordance with its plain ordinary meaning and refers to a chemical composition or compound having antineoplastic properties or the ability to inhibit the growth or proliferation of cells.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (GLEEVEC®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; hereguiln; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone BI; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or r1L.sub.2), interferon alfa-2a; interferon alfa-2b; interferon alfa-n1; interferon alfa-n3; interferon beta-la; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-azaepothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (IRESSA™), erlotinib (TARCEVA™), cetuximab (ERBITUX™), lapatinib (TYKERB™), panitumumab (VECTIBIX™), vandetanib (CAPRELSA™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. In embodiments contacting includes allowing a compound described herein to interact with a protein or enzyme that is involved in a signaling pathway.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator. In embodiments, activation refers to an increase in the activity of a signal transduction pathway or signaling pathway. Thus, activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Selective" or "selectivity" or the like of a compound refers to the compound's ability to discriminate between molecular targets. "Specific", "specifically", "specificity", or the like of a compound refers to the compound's ability to cause a particular action, such as activation, to a particular molecular target with minimal or no action to other proteins in the cell.

The terms "synergy", "synergism", "synergistic", "combined synergistic amount", and "synergistic therapeutic effect" are used herein interchangeably and refer to a measured effect of compounds administered in combination where the measured effect is greater than the sum of the individual effects of each of the compounds administered alone as a single agent.

A "TGR5 ligand" refers to a composition (e.g. compound, amino acid, peptide, polypeptide, antibody, nucleic acid, polynucleotide) which selectively binds to TGR5 ("Takeda G-protein-coupled receptor 5"). A TGR5 ligand may be a "natural product TGR5 agonist". The term "natural product TGR5 agonist" refers to physiological ligands of TGR5 which bind to, and activate TGR5. The term encompasses TGR5 ligands such as bile acids (e.g. CA, LCA, DCA, CDCA, and UDCA) as well as derivatives of bile acids which are naturally synthesized by a host organism. Natural product TGR5 agonists also include triterpenoids which bind to and activate TGR5.

The terms "cholic acid" or "CA," "deoxycholic acid" or "DCA," "lithocholic acid" or "LCA," "ursodeoxycholic acid" or "UDCA," and "chenodeoxycholic acid" or "CDCA" refer to natural product TGR5 agonist bile acids having the respective formulae:

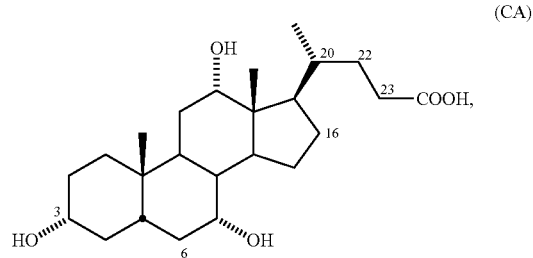

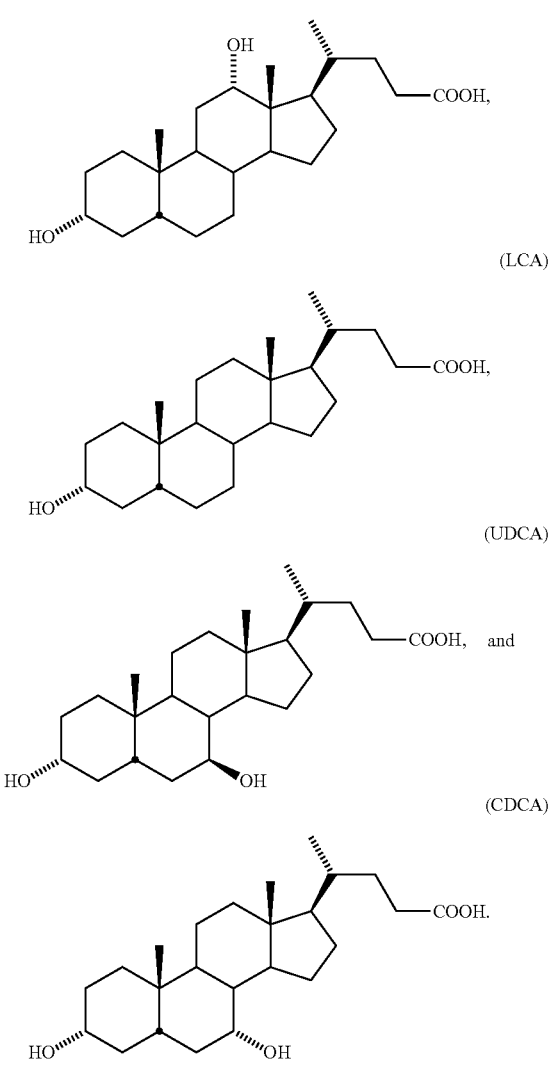

I. Compositions and Complexes

The complexes described herein may be useful for treating diabetes and its associated diseases, polycystic ovary syndrome, cardiovascular disease, and cancer. Accordingly, in one aspect is a complex that includes a metformin or metformin analogue non-covalently bound to a TGR5 ligand.

Figure 13:
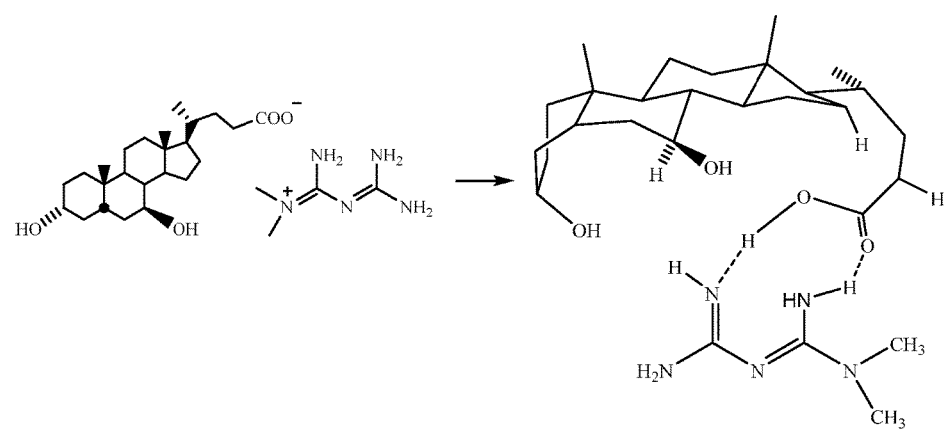
FIG. 13 Proposed metformin-UDCA complex stabilized by complexation through cations of metformin to oxygens of UDCA by intramolecular hydrogen bonds.

In another aspect is a complex between a metformin or metformin analogue and a TGR5 ligand, wherein the TGR5 ligand is non-covalently bound to the metformin or metformin analogue. In yet another aspect is a complex consisting of a metformin or metformin analogue non-covalently bound to a TGR5 ligand. The non-covalent bond may be an ionic bond. Thus, in embodiments, the non-covalent bond between the metformin or metformin analogue and the TGR5 ligand is an ionic bond and forms a salt (i.e. a salt complex). The complex may include a metformin or metformin analogue non-covalently bound to a TGR5 ligand, where the metformin or metformin analogue acts as a proton acceptor and the TGR5 ligand acts as a proton donor, thereby forming a salt (i.e. a salt complex). In embodiments, the reaction of metformin or metformin analogue with anionic TGR5 ligands described herein results in the formation metformin-based TGR5 ligand complexes (e.g. a salt) indicating the participation of both metformin and TGR5 ligands as complexing ligands. In embodiments, the ionic bond is stabilized by intramolecular hydrogen bonds. The non-covalent bond may be a hydrogen bond or a series of hydrogen bonds between the metformin or metformin analogue and the TGR5 ligand. In embodiments, the hydrogen bond or series of hydrogen bonds are part of a hydrogen bond network between the metformin or metformin analogue and the TGR5 ligand. In embodiments, the hydrogen bond is representative of FIG. 13.

In embodiments, the complexes described herein include about a 1:1 molar ratio of the metformin or metformin analogue to the TGR5 ligand. The complexes described herein may be include a 1:1 molar ratio of the metformin or metformin analogue and the TGR5 ligand.

Metformin (N,N-dimethylbiguanidine), Formula (I), is a potent anti-diabetic agent often used as a first-line treatment for patients with type II diabetes. Metformin may be administered in treating overweight and obese patients. Oral absorption of metformin is variable and incomplete with tested oral bioavailability of about 50-60% under fasting conditions. Metformin is known to be slowly absorbed with peak plasma concentrations ($C_{max}$) reached within one to three hours of taking an immediate-release metformin formulation. Metformin may not metabolized. The average elimination half-life in plasma is 6.2 hours.

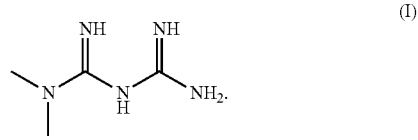

(I)

As set forth herein, the term "metformin analogue" refers to compounds having structural similarity to metformin which retain at least 10, 20, 30, 40, 50, 60, 70, 80, 85, 90, 95, 96, 97, 98, 99, or 100% of the activity of metformin. In embodiments, a metformin analogue may be more potent than metformin (i.e. have greater effect than metformin). Metformin analogues useful in the present invention include those analogues described by, for example: U.S. Pat. Appl. No. 20110021634; U.S. Pat. Appl. No. 20110171142; U.S. Pat. No. 6,031,004; U.S. Pat. No. 6,676,966; U.S. Pat. Appl. No. 20110257432; U.S. Pat. Appl. No. 20120220664; U.S. Pat. No. 5,955,106; U.S. Pat. Appl. No. 20050182029; WO 2004110422; U.S. Pat. Appl. No. 20120219623; W.O. Pat. Appl. No. 2013188452; U.S. Pat. No. 6,031,004; C.N. Pat. Appl. 10 No. 101691344; W.O. Pat. Appl. No. 2002012177; and U.S. Pat. No. 4,080,472.

The TGR5 ligand may be a natural product TGR5 agonist or a synthetic TGR5 agonist derivative. The natural product TGR5 agonist may be a natural triterpenoid TGR5 agonist or a natural product bile acid. In embodiments, the natural product TGR5 agonist is a naturally occurring analogue of the natural product TGR5 agonist. The synthetic TGR5 agonist derivative may be a synthetic TGR5 triterpenoid agonist derivative or a synthetic bile acid derivative.

In embodiments, the TGR5 ligand is a natural product bile acid or a synthetic bile acid derivative. The TGR5 ligand may be a natural product bile acid. The natural product bile acid may be cholic acid (CA), lithocholic acid (LCA), chenodeoxycholic acid (CDCA), ursodeoxycholic acid (UDCA), deoxycholic acid (DCA), or a natural analogue thereof. In embodiments, the natural analogue is, for example, muro-CA (muricholic acid α, β, γ, ω forms), tauro-CA, glyco-CA, hyo-DCA, lago-DCA, nor-DCA, HDCA, tauro-HDCA, glyco-HDCA, tauro-CDCA, glyco-CDCA, homo-UDCA, iso-UDCA, tauro-UDCA, glyco-UDCA, iso-LCA, tauro-LCA, or glyco-LCA.

The TGR5 ligand may be a synthetic bile acid derivative. The synthetic bile acid derivative may have the formula:

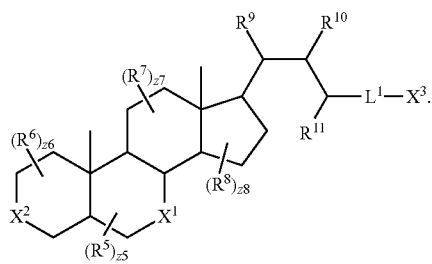

(II)

In formula (II), $L^1$ is a bond, substituted or unsubstituted alkylene, or substituted or unsubstituted heteroalkylene. $X^1$ is C(O) or C($R^1$)($R^2$) and $X^2$ is C(O) or C($R^3$)($R^4$). $X^3$ is —C(O)NH-$L^2$-$R^{12}$, —C(O)O-$L^2$-$R^{12}$, —C(O)-$L^2$-$R^{12}$, —S(O)n-$L^2$-$R^{12}$, —S(O$R^{13}$)(O$R^{14}$)O-$L^2$-$R^2$, or a first acid moiety. The symbol n1 is 1, 2, or 3. $L^2$ is independently a bond, substituted or unsubstituted alkylene, substituted or unsubstituted heteroalkylene. $R^1$, $R^2$, $R^3$, $R^4$ and $R^{11}$ are independently hydrogen, unsubstituted alkyl, or —O$R^{13}$. $R^5$, $R^6$, $R^7$, $R^8$, $R^9$, and $R^{10}$ are independently hydrogen, halogen, —$N_3$, —$CF_3$, —$CCl_3$, —$CBr_3$, —$CI_3$, —CN, —CHO, —O$R^{13}$, —N$R^{13}R^{14}$, —CON$R^{13}R^{14}$, —$NO_2$, —S$R^{13}$, —SO$_{n3}R^{13}$, —SO$_{n3}$O$R^{13}$, —SO$_{n3}$N$R^{13}R^{14}$, —NHN$R^{13}R^{14}$, —ON$R^{13}R^{14}$, —NHC(O)NH$R^{13}R^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n3 is 1 or 2. The symbol z5 is 1, 2, 3, 4, 5, or 6. The symbols z6 and z8 are independently 1, 2, 3, 4, 5, 6, 7, or 8. The symbol z7 is 1, 2, 3, 4, 5, 6, or 7. $R^{12}$ is an second acid moiety. $R^{13}$ and $R^{14}$ are independently are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$ may be a bond or substituted or unsubstituted alkylene. $L^1$ may be a bond or substituted or unsubstituted heteroalkylene. $L^1$ may be substituted or unsubstituted alkylene or substituted or unsubstituted heteroalkylene. $L^1$ may be a bond. In embodiments, $L^1$ is substituted or unsubstituted alkylene. In embodiments, $L^1$ is $R^{23}$-substituted or unsubstituted alkylene. $L^1$ may be unsubstituted alkylene. $L^1$ may be substituted or unsubstituted $C_1$-$C_{20}$ alkylene. $L^1$ may be $R^{23}$-substituted or unsubstituted $C_1$-$C_{20}$ alkylene. $L^1$ may be unsubstituted $C_1$-$C_{20}$ alkylene. $L^1$ may be substituted or unsubstituted $C_1$-$C_{10}$ alkylene. $L^1$ may be $R^{23}$-substituted or unsubstituted $C_1$-$C_{10}$ alkylene. $L^1$ may be unsubstituted $C_1$-$C_{10}$ alkylene. $L^1$ may be substituted or unsubstituted $C_1$-$C_5$ alkylene. $L^1$ may be $R^{23}$-substituted or unsubstituted $C_1$-$C_5$ alkylene. $L^1$ may be unsubstituted $C_1$-$C_5$ alkylene. $L^1$ may be substituted or unsubstituted heteroalkylene. $L^1$ may be $R^{23}$-substituted or unsubstituted heteroalkylene. $L^1$ may be unsubstituted heteroalkylene. $L^1$ may be substituted or unsubstituted 2 to 20 membered heteroalkylene. $L^1$ may be $R^{23}$-substituted or unsubstituted 2 to 20 membered heteroalkylene. $L^1$ may be unsubstituted 2 to 20 membered heteroalkylene. $L^1$ may be substituted or unsubstituted 2 to 10 membered heteroalkylene. $L^1$ may be $R^{23}$-substituted or unsubstituted 2 to 10 membered heteroalkylene. $L^1$ may be unsubstituted 2 to 10 membered heteroalkylene. $L^1$ may be substituted or unsubstituted 2 to 6 membered heteroalkylene. $L^1$ may be $R^{23}$-substituted or unsubstituted 2 to 6 membered heteroalkylene. $L^1$ may be unsubstituted 2 to 6 membered heteroalkylene.

$R^{23}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)NH$NH_2$, —NHC(O)$NH_2$, —NHSO$_2$H, —NHC(O)H, —NHC(O)OH, —NHOH, —O$CF_3$, —O$CHF_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$ substituted or unsubstituted heteroaryl.

$R^{24}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)NH$NH_2$, —NHC(O)$NH_2$, —NHSO$_2$H, —NHC(O)H, —NHC(O)OH, —NHOH, —O$CF_3$, —O$CHF_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

$R^{25}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)NH$NH_2$, —NHC(O)$NH_2$, —NHSO$_2$H, —NHC(O)H, —NHC(O)OH, —NHOH, —O$CF_3$, —O$CHF_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

$R^{26}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)NH$NH_2$, —NHC(O)$NH_2$, —NHSO$_2$H, —NHC(O)H, —NHC(O)OH, —NHOH, —O$CF_3$, —O$CHF_2$, unsubstituted alkyl, unsubstituted heteroalkyl, unsubstituted cycloalkyl, unsubstituted heterocycloalkyl, unsubstituted aryl, or unsubstituted heteroaryl.

$R^5$, $R^6$, $R^7$, $R^8$, $R^9$, and $R^{10}$ may independently be hydrogen, halogen, —$N_3$, —$CF_3$, —$CCl_3$, —$CBr_3$, —$CI_3$, —CN, —CHO, —O$R^{13}$, —N$R^{13}R^{14}$, —CON$R^{13}R^{14}$, —$NO_2$, —S$R^{13}$, —SO$_{n3}R^{13}$, —SO$_3$O$R^{13}$, —SO$_{n3}$N$R^{13}R^{14}$, —NHN$R^{13}R^{14}$, —ON$R^{13}R^{14}$, Or —NHC(O)NH$R^{13}R^{14}$. $R^5$, $R^6$, $R^7$, $R^8$, $R^9$, and $R^{10}$ may independently be hydrogen, halogen, —$N_3$, —$CF_3$, —$CCl_3$, —$CBr_3$, —$CI_3$, —CN, —CHO, —OH, —$NH_2$, —$CONH_2$, —$NO_2$, or —SH. $R^5$, $R^6$, $R^7$, $R^8$, $R^9$, and $R^{10}$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$, $R^6$, $R^7$, $R^8$, $R^9$, and $R^{10}$ may independently be substituted or unsubstituted alkyl. $R^5$, $R^6$, $R^7$, $R^8$, $R^9$, and $R^{10}$ may independently be $R^{27}$-substituted or unsubstituted alkyl. $R^5$, $R^6$, $R^7$, $R^8$, $R^9$, and $R^{10}$ may independently be unsubstituted alkyl. $R^5$, $R^6$, $R^7$, $R^8$, $R^9$, and $R^{10}$ may independently be substituted or unsubstituted $C_1$-$C_{20}$ alkyl. $R^5$, $R^6$, $R^7$, $R^8$, $R^9$, and $R^{10}$ may independently be $R^{27}$-substituted or unsubstituted $C_1$-$C_{20}$ alkyl. $R^5$, $R^6$, $R^7$, $R^8$, $R^9$, and $R^{10}$ may independently be unsubstituted $C_1$-$C_{20}$ alkyl. $R^5$, $R^6$, $R^7$, $R^8$, $R^9$, and $R^{10}$ may independently be substituted or unsubstituted $C_1$-$C_{10}$ alkyl. $R^5$, $R^6$, $R^7$, $R^8$, $R^9$, and $R^{10}$ may independently be $R^{27}$ substituted or unsubstituted $C_1$-$C_{10}$ alkyl. $R^5$, $R^6$, $R^7$, $R^8$, $R^9$, and $R^{10}$ may independently be unsubstituted $C$-$C_{10}$ alkyl. $R^5$, $R^6$, $R^7$, $R^8$, $R^9$, and $R^{10}$ may independently be substituted or unsubstituted $C_1$-$C_5$ alkyl. $R^5$, $R^6$, $R^7$, $R^8$, $R^9$, and $R^{10}$ may independently be $R^{27}$-substituted or unsubstituted $C_1$-$C_5$ alkyl. $R^5$, $R^6$, $R^7$, $R^8$, $R^9$, and $R^{10}$ may independently be unsubstituted $C_1$-$C_5$ alkyl. $R^5$, $R^6$, $R^7$, $R^8$, $R^9$, and $R^{10}$ may independently be methyl or substituted or unsubstituted ethyl. $R^5$, $R^6$, $R^7$, $R^8$, $R^9$, and $R^{10}$ may independently be methyl or $R^{27}$-substituted or unsubstituted ethyl. In embodiments, $R^5$, $R^6$, $R^7$, $R^8$, $R^9$, and $R^{10}$ are independently methyl or unsubstituted ethyl.

$R^5$, $R^6$, $R^7$, $R^8$, $R^9$, and $R^{10}$ may independently be substituted or unsubstituted heteroalkyl. $R^5$, $R^6$, $R^7$, $R^8$, $R^9$, and $R^{10}$ may independently be $R^{27}$-substituted or unsubstituted heteroalkyl. $R^5$, $R^6$, $R^7$, $R^8$, $R^9$, and $R^{10}$ may independently be unsubstituted heteroalkyl. $R^5$, $R^6$, $R^7$, $R^8$, $R^9$, and $R^{10}$ may independently be substituted or unsubstituted 2 to 20 membered heteroalkyl. $R^5$, $R^6$, $R^7$, $R^8$, $R^9$, and $R^{10}$ may independently be $R^{27}$-substituted or unsubstituted 2 to 20 membered heteroalkyl. $R^5$, $R^6$, $R^7$, $R^8$, $R^9$, and $R^{10}$ may independently be unsubstituted 2 to 20 membered heteroalkyl. $R^5$, $R^6$, $R^7$, $R^8$, $R^9$, and $R^{10}$ may independently be substituted or unsubstituted 2 to 10 membered heteroalkyl. $R^5$, $R^6$, $R^7$, $R^8$, $R^9$, and $R^{10}$ may independently be $R^{27}$-substituted or unsubstituted 2 to 10 membered heteroalkyl. $R^5$, $R^6$, $R^7$, $R^8$, $R^9$, and $R^{10}$ may independently be unsubstituted 2 to 10 membered heteroalkyl. $R^5$, $R^6$, $R^7$, $R^8$, $R^9$, and $R^{10}$ may independently be substituted or unsubstituted 2 to 6 membered heteroalkyl. $R^5$, $R^6$, $R^7$, $R^8$, $R^9$, and $R^{10}$ may independently be $R^{27}$-substituted or unsubstituted 2 to 6 membered heteroalkyl. $R^5$, $R^6$, $R^7$, $R^8$, $R^9$, and $R^{10}$ may independently be unsubstituted 2 to 6 membered heteroalkyl.

$R^5$, $R^6$, $R^7$, $R^8$, $R^9$, and $R^{10}$ may independently be substituted or unsubstituted 3 to 10 membered cycloalkyl. $R^5$, $R^6$, $R^7$, $R^8$, $R^9$, and $R^{10}$ may independently be $R^{27}$-substituted or unsubstituted 3 to 10 membered cycloalkyl. $R^5$, $R^6$, $R^7$, $R^8$, $R^9$, and $R^{10}$ may independently be unsubstituted 3 to 10 membered cycloalkyl. $R^5$, $R^6$, $R^7$, $R^8$, $R^9$, and $R^{10}$ may independently be substituted or unsubstituted 3 to 6 membered cycloalkyl. $R^5$, $R^6$, $R^7$, $R^8$, $R^9$, and $R^{10}$ may independently be $R^{27}$-substituted or unsubstituted 3 to 6 membered cycloalkyl. $R^5$, $R^6$, $R^7$, $R^8$, $R^9$, and $R^{10}$ may independently be unsubstituted 3 to 6 membered cycloalkyl. $R^5$, $R^6$, $R^7$, $R^8$, $R^9$, and $R^{10}$ may independently be substituted or unsubstituted 4 to 6 membered cycloalkyl. $R^5$, $R^6$, $R^7$, $R^8$, $R^9$, and $R^{10}$ may independently be $R^{27}$-substituted or unsubstituted 4 to 6 membered cycloalkyl. $R^5$, $R^6$, $R^7$, $R^8$, $R^9$, and $R^{10}$ may independently be unsubstituted 4 to 6 membered cycloalkyl. $R^5$, $R^6$, $R^7$, $R^8$, $R^9$, and $R^{10}$ may independently be substituted or unsubstituted 5 or 6 membered cycloalkyl. $R^5$, $R^6$, $R^7$, $R^8$, $R^9$, and $R^{10}$ may independently be $R^{27}$-substituted or unsubstituted 5 or 6 membered cycloalkyl. $R^5$, $R^6$, $R^7$, $R^8$, $R^9$, and $R^{10}$ may independently be unsubstituted 5 or 6 membered cycloalkyl.

$R^5$, $R^6$, $R^7$, $R^8$, $R^9$, and $R^{10}$ may independently be substituted or unsubstituted 3 to 10 membered heterocycloalkyl. $R^5$, $R^6$, $R^7$, $R^8$, $R^9$, and $R^{10}$ may independently be $R^{27}$-substituted or unsubstituted 3 to 10 membered heterocycloalkyl. $R^5$, $R^6$, $R^7$, $R^8$, $R^9$, and $R^{10}$ may independently be unsubstituted 3 to 10 membered heterocycloalkyl. $R^5$, $R^6$, $R^7$, $R^8$, $R^9$, and $R^{10}$ may independently be substituted or unsubstituted 3 to 6 membered heterocycloalkyl. $R^5$, $R^6$, $R^7$, $R^8$, $R^9$, and $R^{10}$ may independently be $R^{27}$-substituted or unsubstituted 3 to 6 membered heterocycloalkyl. $R^5$, $R^6$, $R^7$, $R^8$, $R^9$, and $R^{10}$ may independently be unsubstituted 3 to 6 membered heterocycloalkyl. $R^5$, $R^6$, $R^7$, $R^8$, $R^9$, and $R^{10}$ may independently be substituted or unsubstituted 4 to 6 membered heterocycloalkyl. $R^5$, $R^6$, $R^7$, $R^8$, $R^9$, and $R^{10}$ may independently be $R^{27}$-substituted or unsubstituted 4 to 6 membered heterocycloalkyl. $R^5$, $R^6$, $R^7$, $R^8$, $R^9$, and $R^{10}$ may independently be unsubstituted 4 to 6 membered heterocycloalkyl. $R^5$, $R^6$, $R^7$, $R^8$, $R^9$, and $R^{10}$ may independently be substituted or unsubstituted 5 or 6 membered heterocycloalkyl. $R^5$, $R^6$, $R^7$, $R^8$, $R^9$, and $R^{10}$ may independently be $R^{27}$-substituted or unsubstituted 5 or 6 membered heterocycloalkyl. $R^5$, $R^6$, $R^7$, $R^8$, $R^9$, and $R^{10}$ may independently be unsubstituted 5 or 6 membered heterocycloalkyl.

$R^5$, $R^6$, $R^7$, $R^8$, $R^9$, and $R^{10}$ may independently be substituted or unsubstituted 5 to 8 membered aryl. $R^5$, $R^6$, $R^7$, $R^8$, $R^9$, and $R^{10}$ may independently be $R^{27}$-substituted or unsubstituted 5 to 8 membered aryl. $R^5$, $R^6$, $R^7$, $R^8$, $R^9$, and $R^{10}$ may independently 5 to 8 membered unsubstituted aryl. $R^5$, $R^6$, $R^7$, $R^8$, $R^9$, and $R^{10}$ may independently be substituted or unsubstituted 5 or 6 membered aryl. $R^5$, $R^6$, $R^7$, $R^8$, $R^9$, and $R^{10}$ may independently be $R^{27}$ substituted or unsubstituted 5 or 6 membered aryl. $R^5$, $R^6$, $R^7$, $R^8$, $R^9$, and $R^{10}$ may independently be 5 or 6 membered unsubstituted aryl.

$R^5$, $R^6$, $R^7$, $R^8$, $R^9$, and $R^{10}$ may independently be substituted or unsubstituted 5 to 8 membered heteroaryl. $R^5$, $R^6$, $R^7$, $R^8$, $R^9$, and $R^{10}$ may independently be $R^{27}$-substituted or unsubstituted 5 to 8 membered heteroaryl. $R^5$, $R^6$, $R^7$, $R^8$, $R^9$, and $R^{10}$ may independently 5 to 8 membered unsubstituted heteroaryl. $R^5$, $R^6$, $R^7$, $R^8$, $R^9$, and $R^{10}$ may independently be substituted or unsubstituted 5 or 6 membered heteroaryl. $R^5$, $R^6$, $R^7$, $R^8$, $R^9$, and $R^{10}$ may independently be $R^{27}$-substituted or unsubstituted 5 or 6 membered heteroaryl. $R^5$, $R^6$, $R^7$, $R^8$, $R^9$, and $R^{10}$ may independently be 5 or 6 membered unsubstituted heteroaryl.

$R^5$ may be hydrogen. $R^5$ may be on the 6-position. $R^5$ may be unsubstituted alkyl. $R^5$ may be $C_1$-$C_{10}$ unsubstituted alkyl. $R^5$ is $C_1$-$C_5$ unsubstituted alkyl. $R^5$ may be ethyl. $R^5$ may be attached to a chiral carbon having α-stereochemistry. $R^5$ may be attached to a chiral carbon having α-stereochemistry on the 6-position. $R^5$ may be —$OR^3$, where $R^{13}$ is as described herein. $R^{13}$ may be hydrogen. $R^{13}$ may be unsubstituted alkyl. $R^{13}$ may be $C_1$-$C_{10}$ unsubstituted alkyl. $R^{13}$ may be $C_1$-$C_5$ unsubstituted alkyl. The symbol z5 may be 1 (e.g. $R^5$-substituted at the 6-position). The symbol z5 may be 2, 3, 4, 5, or 6.

$R^9$ may be methyl or substituted or unsubstituted ethyl. $R^9$ may be methyl. $R^9$ may be attached to a chiral carbon having (R) stereochemistry. $R^9$ may be methyl attached to a chiral carbon having (R) stereochemistry.

$R^{11}$ may be hydrogen. $R^{11}$ may be —$OR^3$, where $R^{13}$ is as described herein. In embodiments, $R^{11}$ is —$OR^{13}$, where $R^{13}$ is hydrogen, substituted or unsubstituted alkyl (e.g. $R^{27}$-substituted or unsubstituted alkyl as described herein), or substituted or unsubstituted aryl (e.g. $R^{27}$ substituted or unsubstituted aryl as described herein). In embodiments, $R^{13}$ is hydrogen, methyl (i.e. —$OCH_3$), unsubstituted ethyl (i.e. —$OCH_2CH_3$), or unsubstituted phenyl (i.e. —$O(C_6H_5)$). $R^{11}$ may be $C_1$-$C_{20}$ unsubstituted alkyl. $R^{11}$ may be $C_1$-$C_{10}$ unsubstituted alkyl. $R^{11}$ may be $C_1$-$C_5$ unsubstituted alkyl. $R^{11}$ may be methyl. $R^{11}$ may be ethyl (i.e. unsubstituted). $R^{11}$ may be propyl (i.e. unsubstituted). $R^{11}$ may be attached to a chiral carbon having an (S) stereochemistry. $R^{11}$ may be methyl attached to a chiral carbon having an (S) stereochemistry.

$R^{27}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$ substituted or unsubstituted heteroaryl.

$R^{28}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl.

$R^{29}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$X^1$ may be C(O). $X^1$ may be $C(R^1)(R^2)$. In embodiments, $X^1$ is C(H)OH or $CH_2$.

$X^2$ may be C(O). $X^2$ may be $C(R^3)(R^4)$. In embodiments, $X^2$ is C(H)OH or $CH_2$.

In embodiments, $X^1$ and $X^2$ may be C(O). In embodiments, if $X^1$ is C(O), at least one of $R^3$ and $R^4$ is —OH. In embodiments, $X^1$ is C(O) and $X^2$ is C(O) or $C(R^3)(R^4)$, and wherein $R^3$ is —OH. In embodiments, if $X^1$ is $C(R^1)(R^2)$, $X^2$ may be C(O). In embodiments, if $X^1$ is C(H)OH or $CH_2$, $R^3$ and $R^4$ is —OH. In embodiments, if $X^1$ is $C(R^1)(R^2)$ and $X^2$ is $C(R^3)(R^4)$, at least one of $R^1$, $R^2$, $R^3$, and $R^4$ is not hydrogen. Thus, in embodiments, $X^1$ and $X^2$ are not $CH_2$. In embodiments, $X^1$ and $X^2$ are C(H)OH.

$R^1$, $R^2$, $R^3$, and $R^4$ may independently be hydrogen or unsubstituted alkyl. $R^1$, $R^2$, $R^3$, and $R^4$ may independently be hydrogen or —$OR^{13}$, where $R^{13}$ is as described herein. In embodiments, $R^{13}$ is hydrogen, substituted or unsubstituted alkyl (e.g. $R^{27}$-substituted alkyl) or substituted or unsubstituted aryl (e.g. $R^{27}$-substituted aryl). In embodiments, $R^1$, $R^2$, $R^3$, and $R^4$ may independently be hydrogen, —OH, —$OCH_3$, or —$OCH_2CH_3$.

$R^1$ may be hydrogen or unsubstituted alkyl. $R^1$ may be hydrogen. $R^1$ may be unsubstituted alkyl. $R^1$ may be $C_1$-$C_{20}$ unsubstituted alkyl. $R^1$ may be $C_1$-$C_{10}$ unsubstituted alkyl. $R^1$ may be $C_1$-$C_5$ unsubstituted alkyl. In embodiments, $R^1$ is methyl. $R^1$ may be —$OR^{13}$, where $R^{13}$ is as described herein. In embodiments $R^1$ is —OH.

$R^2$ may be hydrogen or unsubstituted alkyl. $R^2$ may be hydrogen. $R^2$ may be unsubstituted alkyl. $R^2$ may be $C_1$-$C_{20}$ unsubstituted alkyl. $R^2$ may be $C_1$-$C_{10}$ unsubstituted alkyl. $R^2$ may be $C_1$-$C_5$ unsubstituted alkyl. In embodiments, $R^2$ is methyl. $R^2$ may be —$OR^3$, where $R^{13}$ is as described herein. In embodiments $R^2$ is —OH.

$R^1$ and $R^2$ may independently be hydrogen or —OH. Thus, in embodiments, $R^1$ is —OH and $R^2$ is hydrogen. In embodiments, $R^2$ is —OH and $R^1$ is hydrogen. In embodiments, $R^1$ and $R^2$ are hydrogen. In embodiments, $R^1$ and $R^2$ are —OH. In embodiments, $R^1$ and $R^2$ are unsubstituted alkyl (e.g. methyl or ethyl).

$R^3$ may be hydrogen or unsubstituted alkyl. $R^3$ may be hydrogen. $R^3$ may be unsubstituted alkyl. $R^3$ may be $C_1$-$C_{20}$ unsubstituted alkyl. $R^3$ may be $C_1$-$C_{10}$ unsubstituted alkyl. $R^3$ may be $C_1$-$C_5$ unsubstituted alkyl. In embodiments, $R^3$ is methyl. $R^3$ may be —$OR^{13}$, where $R^{13}$ is as described herein. In embodiments $R^3$ is —OH.

$R^4$ may be hydrogen or unsubstituted alkyl. $R^4$ may be hydrogen. $R^4$ may be unsubstituted alkyl. $R^4$ may be $C_1$-$C_{20}$ unsubstituted alkyl. $R^4$ may be $C_1$-$C_{10}$ unsubstituted alkyl. $R^4$ may be $C_1$-$C_5$ unsubstituted alkyl. In embodiments, $R^4$ is methyl. $R^4$ may be —$OR^{13}$, where $R^{13}$ is as described herein. In embodiments $R^4$ is —OH.

$R^3$ and $R^4$ may independently be hydrogen or —OH. Thus, in embodiments, $R^3$ is —OH and $R^4$ is hydrogen. In embodiments, $R^4$ is —OH and $R^3$ is hydrogen. In embodiments, $R^3$ and $R^4$ are hydrogen. In embodiments, $R^3$ and $R^4$ are —OH. In embodiments, $R^3$ and $R^4$ are unsubstituted alkyl (e.g. methyl or ethyl).

In embodiments, $R^1$ and $R^2$ are hydrogen and $R^3$ is —OH. In embodiments, $R^1$ is —OH and $R^3$ is —OH. In embodiments, $R^2$ is —OH and $R^3$ is —OH.

In embodiments, $R^1$, $R^2$, $R^3$, and $R^4$ are defined by formula:

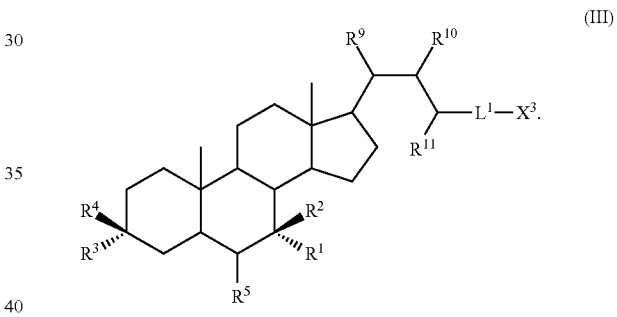

(III)

In formula (III), $R^1$, $R^2$, $R^3$, $R^4$, $R^5$, $R^9$, $R^{10}$, $R^{11}$, $L^1$, and $X^3$ are as defined herein.

$X^3$ may be —$C(O)NH$-$L^2$-$R^{12}$, —$C(O)O$-$L^2$-$R^{12}$, —$C(O)$-$L^2$-$R^{12}$, —$S(O)_{n1}$-$L^2$-$R^{12}$, or —$S(OR^{13})(OR^4)O$-$L^2$-$R^{12}$. $X^3$ may be an acid moiety. In embodiments, $X^3$ is —$C(O)NH$-$L^2$-$R^{12}$, —$C(O)O$-$L^2$-$R^{12}$, or —$C(O)$-$L^2$-$R^{12}$. $X^3$ may be —$S(O)_{n1}$-$L^2$-$R^{12}$, or —$S(OR^{13})(OR^{14})O$-$L^2$-$R^{12}$.

$L^2$ may independently be a bond or substituted or unsubstituted alkylene. $L^2$ may independently be a bond or substituted or unsubstituted heteroalkylene. $L^2$ may independently be substituted or unsubstituted alkylene or substituted or unsubstituted heteroalkylene. $L^2$ may independently be a bond. In embodiments, $L^2$ is independently substituted or unsubstituted alkylene. In embodiments, $L^2$ is independently $R^{30}$-substituted or unsubstituted alkylene. $L^2$ may independently be unsubstituted alkylene. $L^2$ may independently be substituted or unsubstituted $C_1$-$C_{20}$ alkylene. $L^2$ may independently be $R^{30}$-substituted or unsubstituted $C_1$-$C_{20}$ alkylene. $L^2$ may independently be unsubstituted $C_1$-$C_{20}$ alkylene. $L^2$ may independently be substituted or unsubstituted $C_1$-$C_{10}$ alkylene. $L^2$ may independently be $R^{30}$-substituted or unsubstituted $C_1$-$C_{10}$ alkylene. $L^2$ may independently be unsubstituted $C_1$-$C_{10}$ alkylene. $L^2$ may independently be substituted or unsubstituted $C_1$-$C_5$ alkylene. $L^2$ may independently be $R^{30}$-substituted or unsubstituted $C_1$-$C_5$ alkylene. $L^2$ may independently be unsubstituted $C_1$-$C_5$ alkylene.

$L^2$ may independently be substituted or unsubstituted heteroalkylene. $L^2$ may independently be $R^{30}$-substituted or unsubstituted heteroalkylene. $L^2$ may independently be unsubstituted heteroalkylene. $L^2$ may independently be substituted or unsubstituted 2 to 20 membered heteroalkylene. $L^2$ may independently be $R^{30}$-substituted or unsubstituted 2 to 20 membered heteroalkylene. $L^2$ may independently be unsubstituted 2 to 20 membered heteroalkylene. $L^2$ may independently be substituted or unsubstituted 2 to 10 membered heteroalkylene. $L^2$ may independently be $R^{30}$-substituted or unsubstituted 2 to 10 membered heteroalkylene. $L^2$ may independently be unsubstituted 2 to 10 membered heteroalkylene. $L^2$ may independently be substituted or unsubstituted 2 to 6 membered heteroalkylene. $L^2$ may independently be $R^{30}$-substituted or unsubstituted 2 to 6 membered heteroalkylene. $L^2$ may independently be unsubstituted 2 to 6 membered heteroalkylene.

$R^{30}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{31}$-substituted or unsubstituted alkyl, $R^{31}$-substituted or unsubstituted heteroalkyl, $R^{31}$-substituted or unsubstituted cycloalkyl, $R^{30}$-substituted or unsubstituted heterocycloalkyl, $R^{31}$-substituted or unsubstituted aryl, or $R^{31}$ substituted or unsubstituted heteroaryl.

$R^{31}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHC($NH_2$)$NH_2$, —NHOH, —$OCF_3$, —$OCHF_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl.

$R^{32}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

$R^{33}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{30}$ is independently oxo, halogen, —$CF_3$, —CN, —OH, —$NH_2$, —COOH, —SH, —$SO_3H$, $R^{31}$-substituted or unsubstituted alkyl, or $R^{31}$-substituted or unsubstituted heteroalkyl. In embodiments, $R^{30}$ is independently $R^{31}$-substituted or unsubstituted alkyl, or $R^{31}$ substituted or unsubstituted heteroalkyl. $R^{31}$ is as described herein. In embodiments, $R^{31}$ is independently oxo, —OH, —$NH_2$, —COOH, —$CONH_2$, —$NO_2$, —SH, —$SO_3H$, —NHC($NH_2$)$NH_2$, NHC(O)H, —NHC(O)OH, —NHOH, —$OCF_3$, —$OCHF_2$, $R^{32}$-substituted or unsubstituted alkyl, $R^{32}$-substituted or unsubstituted heteroalkyl, $R^{32}$-substituted or unsubstituted heterocycloalkyl, $R^{32}$-substituted or unsubstituted aryl, or $R^{32}$-substituted or unsubstituted heteroaryl.

In embodiments, the symbol z5 is 1. The symbol z5 may be 2, 3, 4, 5, or 6.

$R^{12}$ may be an organic acid. $R^{12}$ may be —COOH (i.e. —COO⁻) or —$SO_3H$ (i.e. —$SO_3^-$).

$R^{13}$ and $R^{14}$ may independently be hydrogen or substituted or unsubstituted alkyl (e.g. $R^{30}$-substituted alkyl). In embodiments, $R^{13}$ and $R^{14}$ are independently hydrogen, methyl, $R^{30}$-substituted or unsubstituted ethyl, or $R^{30}$-substituted or unsubstituted phenyl.

In embodiments, the synthetic bile acid derivative has the formula:

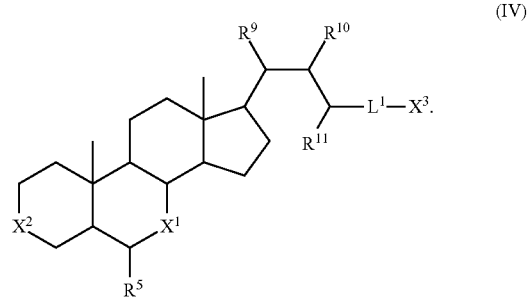

(IV)

In formula (IV), $X^1$, $X^2$, $R^5$, $R^9$, $R^{10}$, $R^{11}$, $L^1$, and $X^3$ are as defined herein, including embodiments thereof.

In embodiments of formula (II), (III), and (IV), $L^1$ is a bond or substituted or unsubstituted alkylene, $X^3$ is —C(O)NH-$L^2$-$R^{12}$, —C(O)O-$L^2$-$R^{12}$, or —C(O)-$L^2$-$R^{12}$, $L^2$ is independently substituted or unsubstituted alkylene, and $R^{12}$ is an acid moiety (e.g. —COOH). In embodiments of formula (II), (III), and (IV), $L^1$ is a bond, substituted or unsubstituted alkylene and $X^3$ is an acid moiety (e.g. —COOH).

In embodiments, the acid moiety (at position $X^3$ or $R^{12}$) forms a non-covalent bond with metformin.

In embodiments, the synthetic bile acid derivative has the formula:

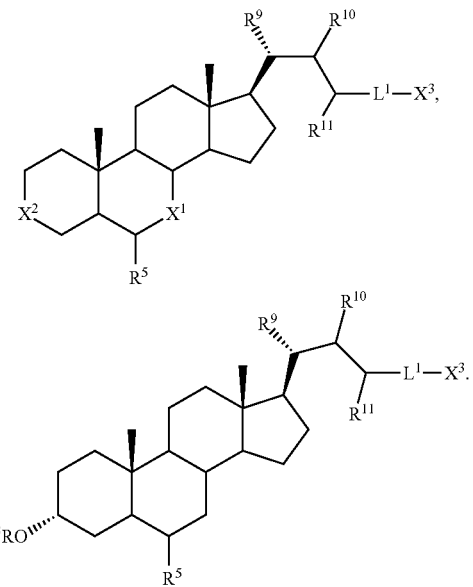

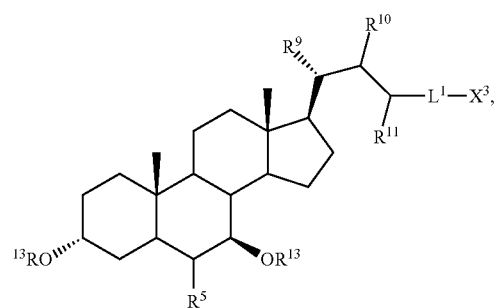
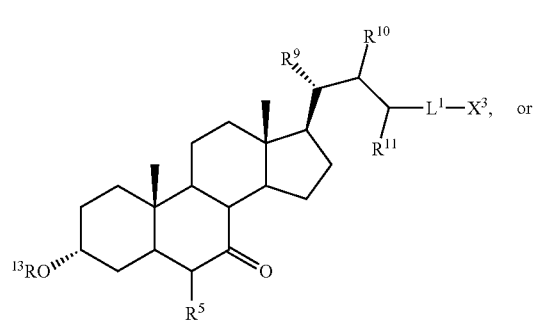
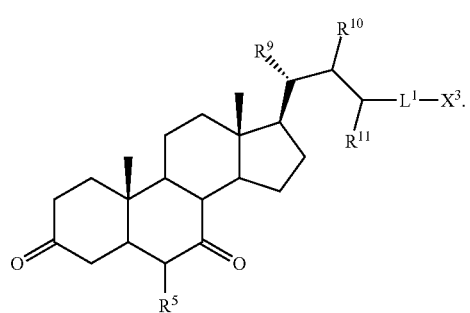
In formula (IV), $X^1$, $X^2$, $R^5$, $R^9$, $R^{10}$, $R^{11}$, $R^{13}$, $L^1$, and $X^3$ are as defined herein, including embodiments thereof.
The synthetic bile acid derivative may have the formula:
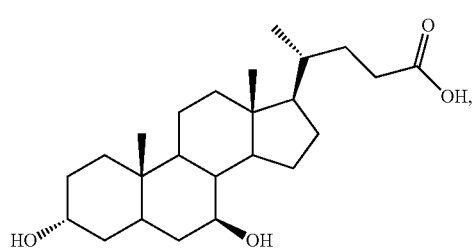
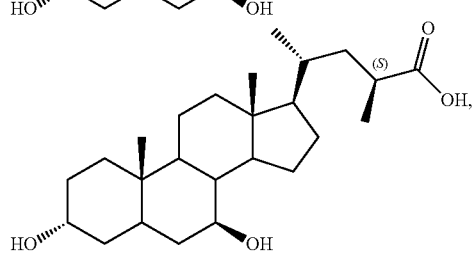
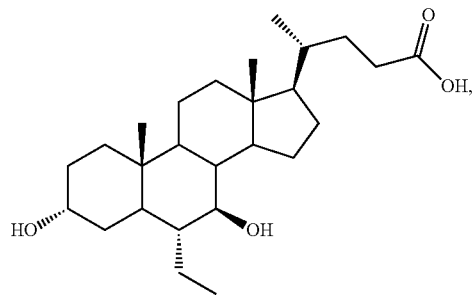
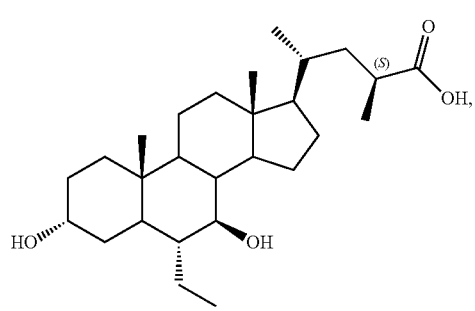
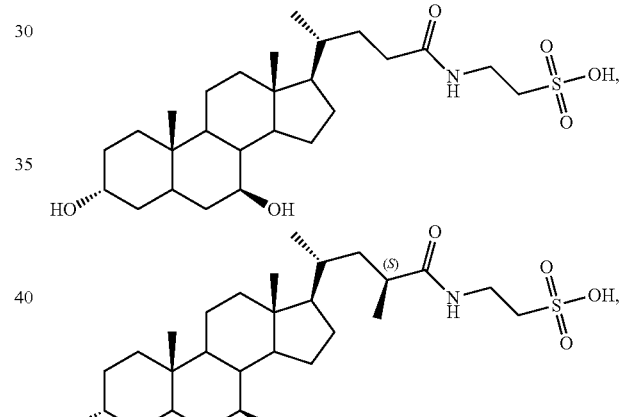
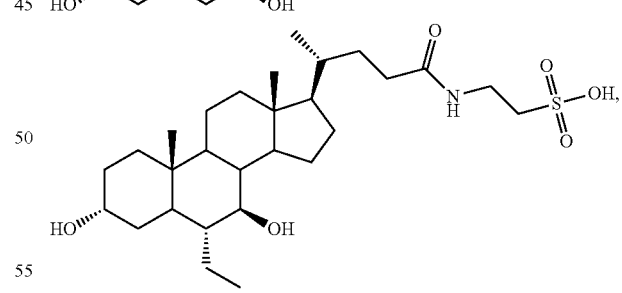
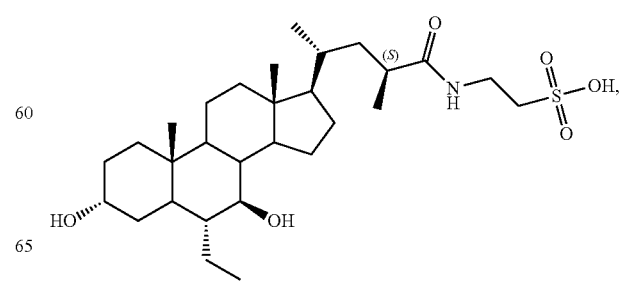

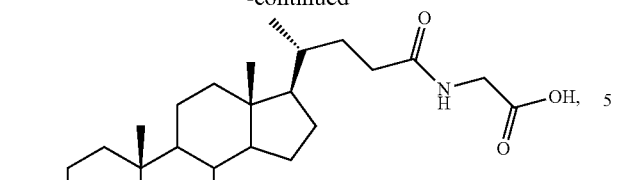
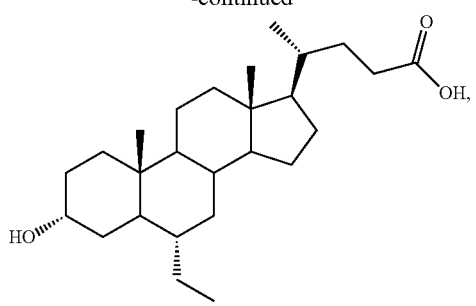
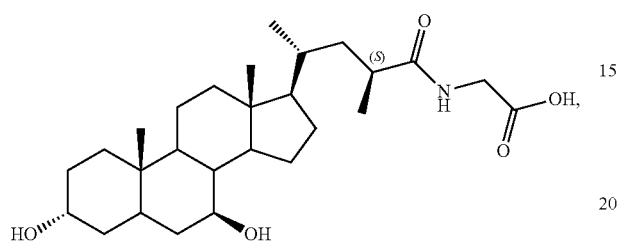
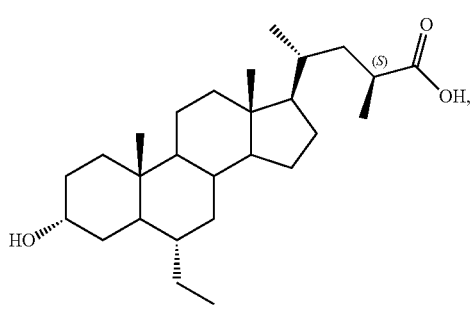
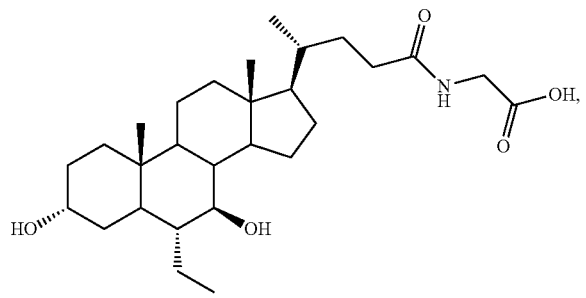
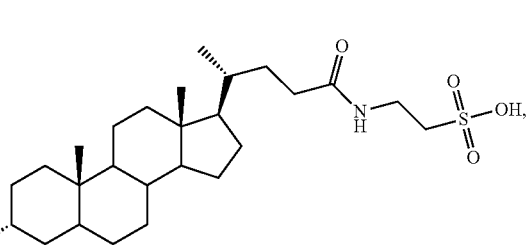
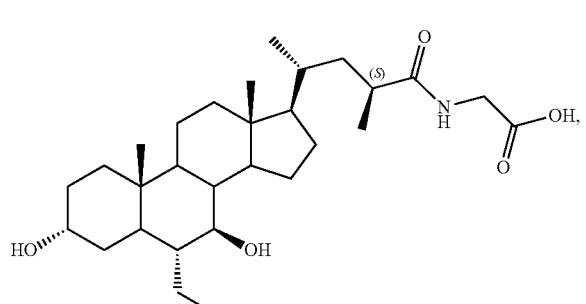
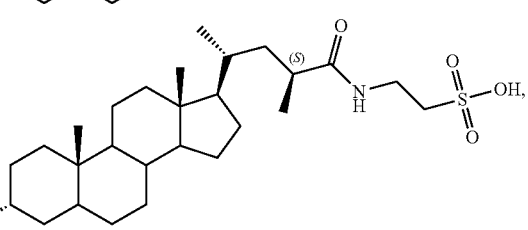
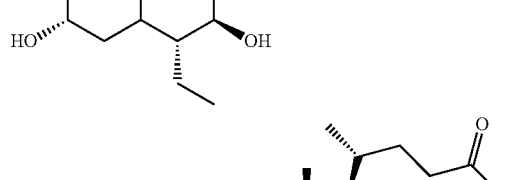
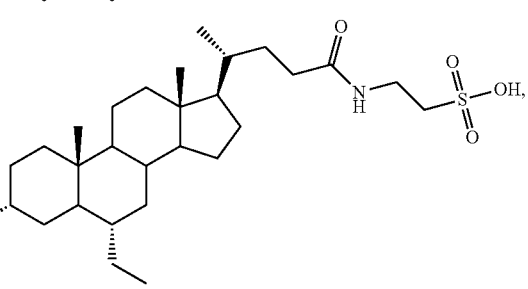
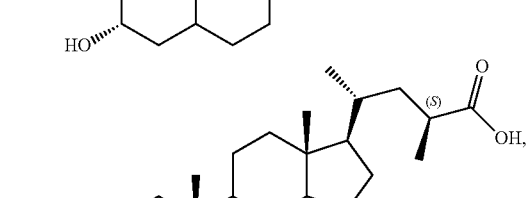
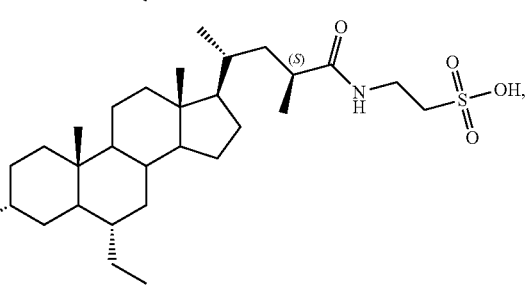

-continued
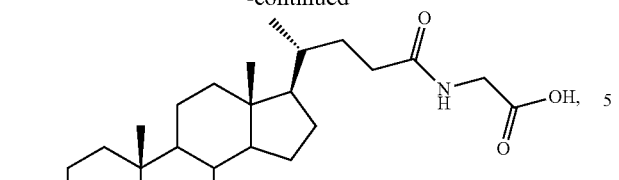
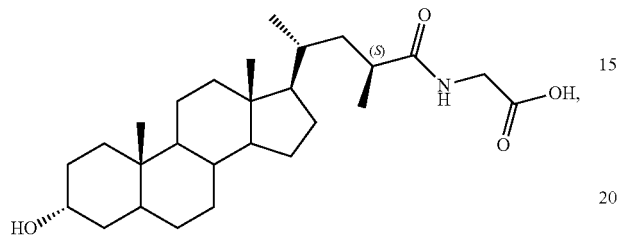
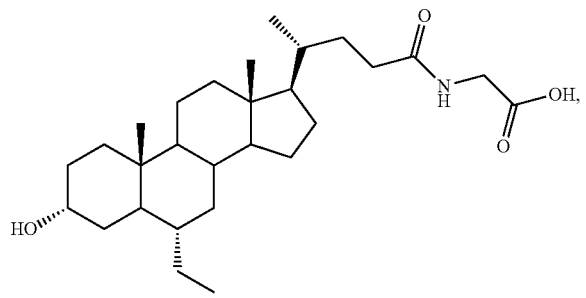
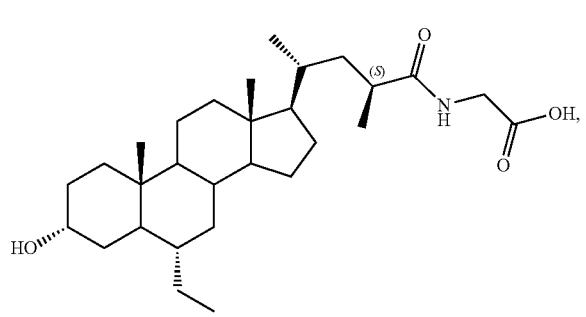
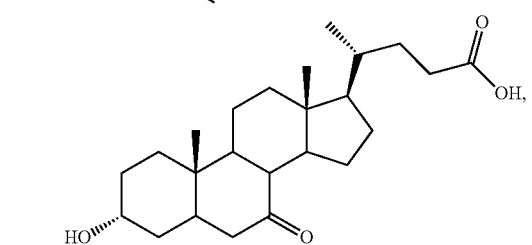
-continued
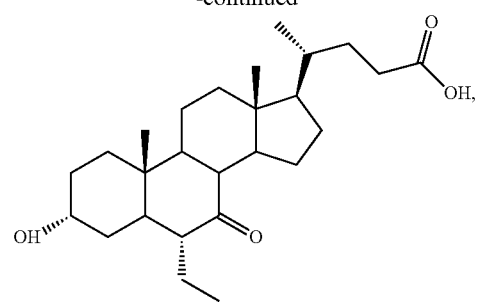
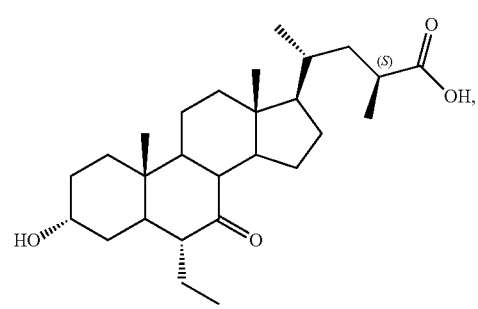
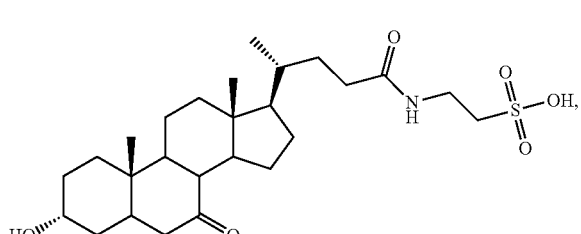
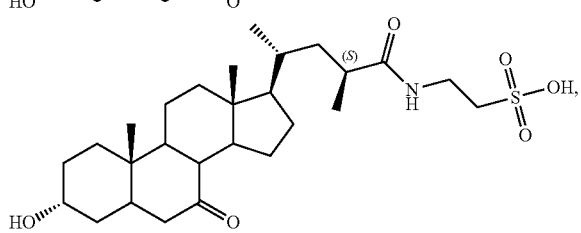
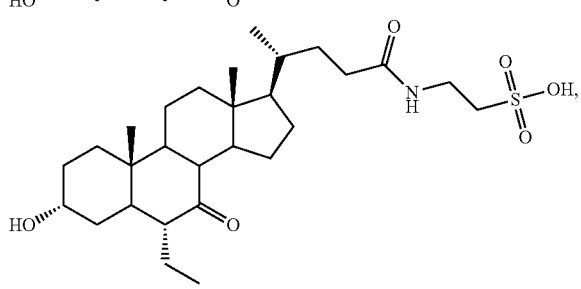
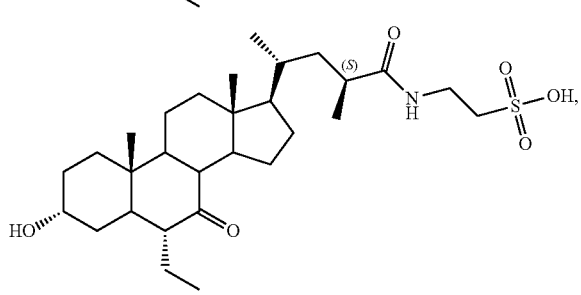

43
-continued
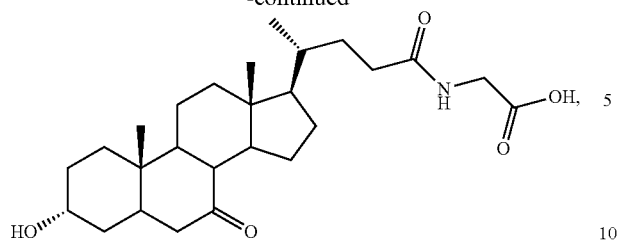
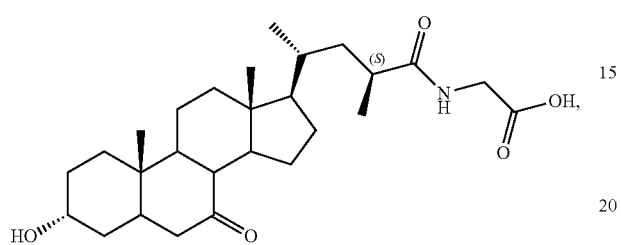
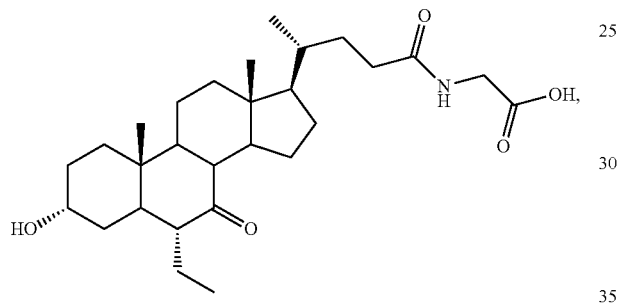
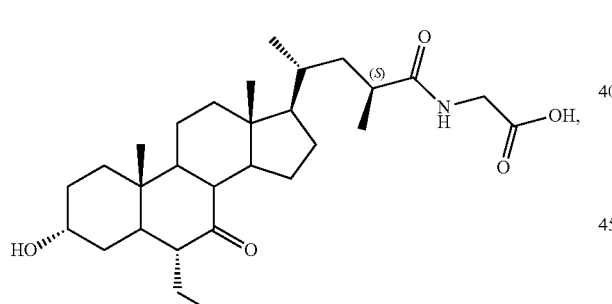
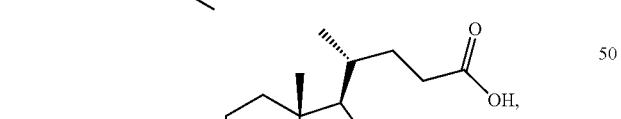
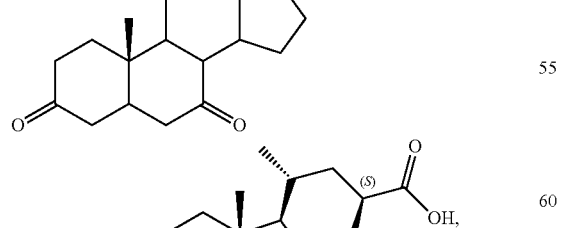
44
-continued
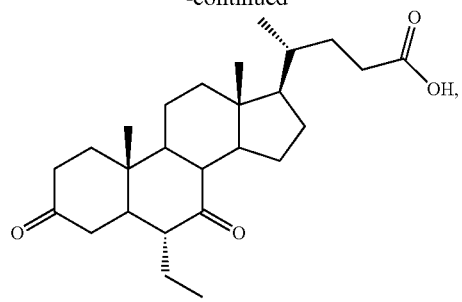
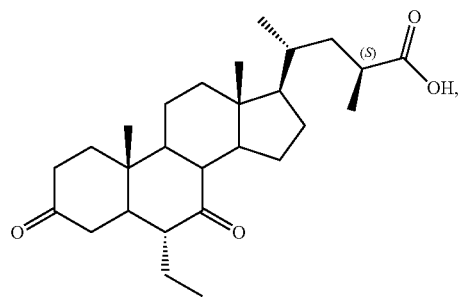
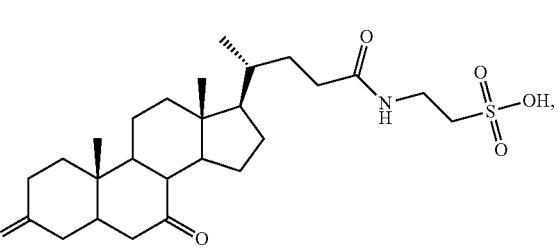
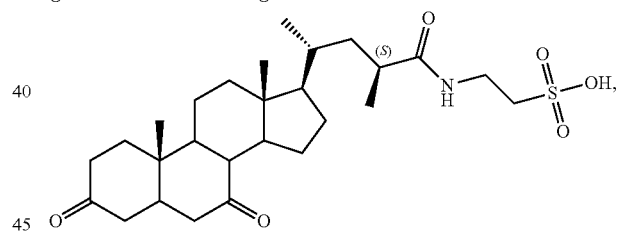
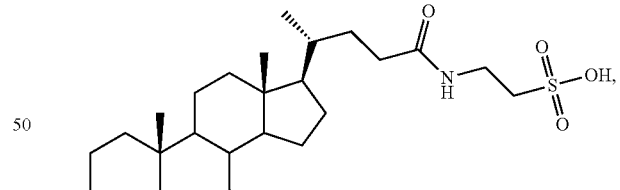
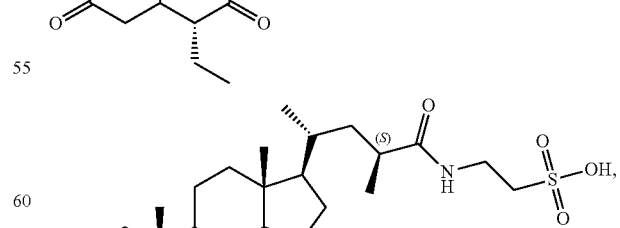

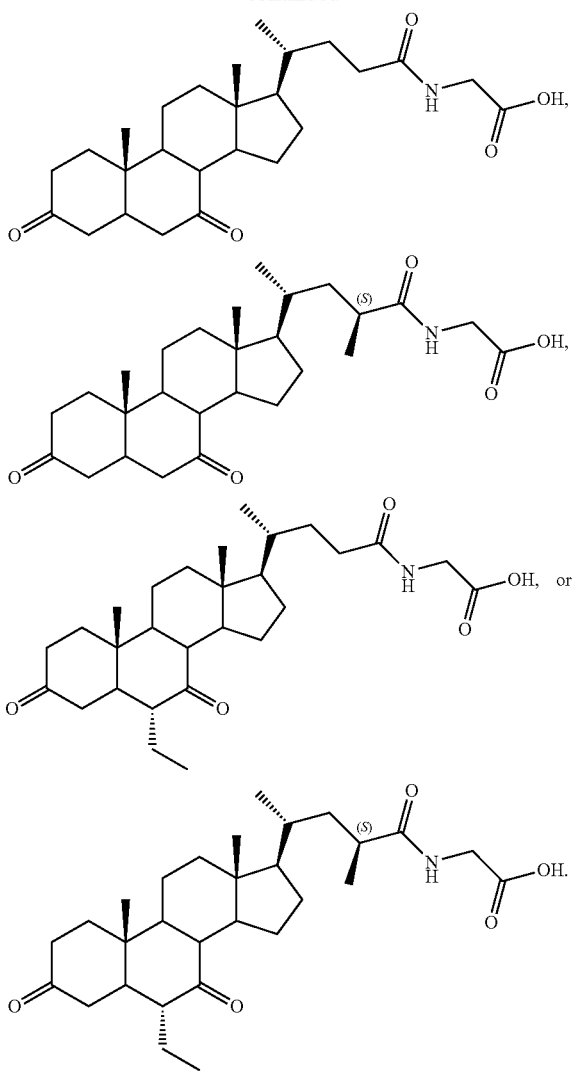

Figure 4:
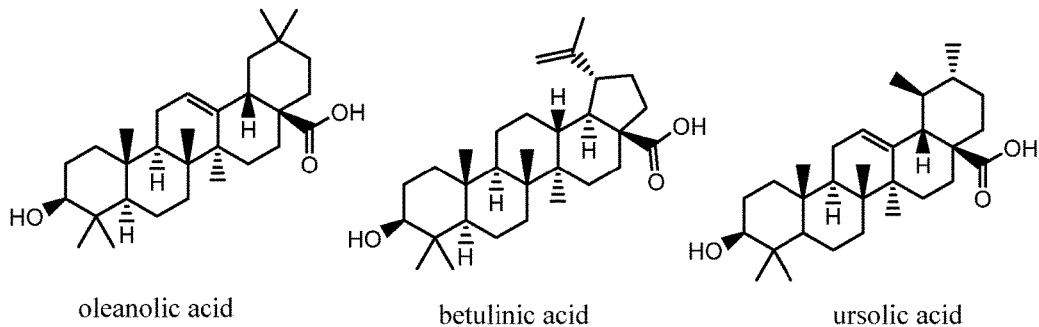
FIG. 4 Chemical structures of natural TGR5 agonists: oleanolic acid, betulinic acid, and ursolic acid.

In embodiments, the TGR5 ligand is a natural product TGR5 agonist or a synthetic TGR5 agonist derivative. In embodiments, the natural product TGR5 agonist is a natural triterpenoid TGR5 agonist and the TGR5 synthetic agonist derivative is a synthetic TGR5 triterpenoid agonist derivative. The natural TGR5 triterpenoid agonist may be oleanolic acid, betulinic acid, or ursolic acid as shown in FIG. 4. The synthetic TGR5 triterpenoid agonist derivative may have the formula:

(V)

or (VI)

In the formulae above, $L^3$ is a bond, substituted or unsubstituted alkylene, or substituted or unsubstituted heteroalkylene. $X^4$ —C(O)NH-$L^4$-$R^{22}$, —C(O)O-$L^4$-$R^{22}$, —C(O)-$L^4$-$R^{22}$, S(O)$_{n2}$-$L^4$-$R^{22}$, —S(OR$^{13}$)(OR$^{14}$)O-$L^4$-$R^{22}$, or a first acid moiety. The symbol n2 is 1, 2, or 3. $L^4$ is independently a bond, substituted or unsubstituted alkylene, substituted or unsubstituted heteroalkylene. $R^{15}$, $R^{16}$, $R^{17}$, $R^{18}$, $R^{19}$, $R^{20}$, and $R^{21}$ are independently hydrogen, halogen, —N$_3$, —CF$_3$, —CCl$_3$, —CBr$_3$, —CI$_3$, —CN, —CHO, —OR$^{13}$, —NR$^{13}$R$^{14}$, —CONR$^{13}$R$^{14}$, —NO$_2$, —SR$^{13}$, —SO$_{n3}$R$^{13}$, —SO$_{n3}$OR$^{13}$, —SO$_{n3}$NR$^{13}$R$^{14}$, —NHNR$^{13}$R$^{14}$, —ONR$^{13}$R$^{14}$, —NHC(O)NHNR$^{13}$R$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n3 is 1 or 2. The symbols z15 and z17 are independently 1, 2, 3, 4, 5, 6, 7, 8 or 9. The symbols z16, z18, and z19 are independently 1, 2, 3, 4, 5, or 6. The symbol z20 is 1, 2, 3, 4, 5, 6, or 7. The symbol z21 is 1, 2, 3, or 4. And $R^{22}$ is a second acid moiety.

$L^3$ may be a bond or substituted or unsubstituted alkylene. $L^3$ may be a bond or substituted or unsubstituted heteroalkylene. $L^3$ may be substituted or unsubstituted alkylene or substituted or unsubstituted heteroalkylene. $L^3$ may be a bond. In embodiments, $L^3$ is substituted or unsubstituted alkylene. In embodiments, $L^3$ is $R^{35}$-substituted or unsubstituted alkylene. $L^3$ may be substituted or unsubstituted $C_1$-$C_{20}$ alkylene. $L^3$ may be $R^{35}$-substituted or unsubstituted $C_1$-$C_{20}$ alkylene. $L^3$ may be substituted or unsubstituted $C_1$-$C_{10}$ alkylene. $L^3$ may be $R^{35}$-substituted or unsubstituted $C_1$-$C_{10}$ alkylene. $L^3$ may be substituted or unsubstituted $C_1$-$C_5$ alkylene. $L^3$ may be $R^{35}$-substituted or unsubstituted $C_1$-$C_5$ alkylene. $L^3$ may be substituted or unsubstituted heteroalkylene. $L^3$ may be $R^{35}$-substituted or unsubstituted heteroalkylene. $L^3$ may be substituted or unsubstituted 2 to 20 membered heteroalkylene. $L^3$ may be $R^{35}$-substituted or unsubstituted 2 to 20 membered heteroalkylene. $L^3$ may be substituted or unsubstituted 2 to 10 membered heteroalkylene. $L^3$ may be $R^{35}$-substituted or unsubstituted 2 to 10 membered heteroalkylene. $L^3$ may be substituted or unsubstituted 2 to 6 membered heteroalkylene. $L^3$ may be $R^{35}$-substituted or unsubstituted 2 to 6 membered heteroalkylene.

$R^{35}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC (O)H, —NHC(O)OH, —NHOH, —OCF$_3$, —OCHF$_2$, R$^{36}$-substituted or unsubstituted alkyl, R$^{36}$-substituted or unsubstituted heteroalkyl, R$^{36}$-substituted or unsubstituted cycloalkyl, R$^{36}$-substituted or unsubstituted heterocycloalkyl, R$^{36}$-substituted or unsubstituted aryl, or R$^{36}$-substituted or unsubstituted heteroaryl.

R$^{36}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, cycloalkyl, unsubstituted heterocycloalkyl, unsubstituted 5 aryl, or unsubstituted heteroaryl.

X$^4$ may be —C(O)NH-L$^4$-R$^{22}$, —C(O)O-L$^4$-R$^{22}$, —C(O)-L$^4$-R$^{22}$, —S(O)$_{n2}$-L$^4$-R$^{22}$, or —S(OR$^{13}$)(OR$^4$)O-L$^4$-R$^{22}$. X$^4$ may be an acid moiety. If X$^4$ is —C(O)NH-L$^4$-R$^{22}$, —C(O)O-L$^4$-R$^{22}$, —C(O)-L$^4$-R$^{22}$, —S(O)$_{n2}$-L$^4$-R$^{22}$, or —S(OR$^{13}$)(OR$^{14}$)O-L$^4$-R$^{22}$, L$^4$ may independently be a bond or substituted or unsubstituted alkylene. L$^4$ may independently be a bond. L$^4$ may independently be substituted or unsubstituted alkylene. In embodiments, L$^4$ is independently substituted or unsubstituted alkylene. In embodiments, L$^4$ is independently R$^{35}$-substituted or unsubstituted alkylene. L$^4$ may independently be substituted or unsubstituted C$_1$-C$_{20}$ alkylene. L$^4$ may independently be R$^{35}$-substituted or unsubstituted C$_1$-C$_{20}$ alkylene. L$^4$ may independently be substituted or unsubstituted C$_1$-C$_{10}$ alkylene. L$^4$ may independently be R$^{35}$-substituted or unsubstituted C$_1$-C$_{10}$ alkylene. L$^4$ may independently be substituted or unsubstituted C$_1$-C$_5$ alkylene. L$^4$ may independently be R$^{35}$-substituted or unsubstituted C$_1$-C$_5$ alkylene. L$^4$ may independently be substituted or unsubstituted heteroalkylene. L$^4$ may independently be R$^{35}$-substituted or unsubstituted heteroalkylene. L$^4$ may independently be substituted or unsubstituted 2 to 20 membered heteroalkylene. L$^4$ may independently be R$^{35}$-substituted or unsubstituted 2 to 20 membered heteroalkylene. L$^4$ may independently be substituted or unsubstituted 2 to 10 membered heteroalkylene. L$^4$ may independently be R$^{35}$-substituted or unsubstituted 2 to 10 membered heteroalkylene. L$^4$ may independently be substituted or unsubstituted 2 to 6 membered heteroalkylene. L$^4$ may independently be R$^{35}$-substituted or unsubstituted 2 to 6 membered heteroalkylene.

R$^{15}$, R$^{16}$, R$^{17}$, R$^{18}$, R$^{19}$, R$^{20}$, and R$^{21}$ may independently be hydrogen, halogen, —N$_3$, —CF$_3$, —CCl$_3$, —CBr$_3$, —CI$_3$, —CN, —CHO, —OR$^{13}$, —NR$^{13}$R$^{14}$, —CONR$^{13}$R$^{14}$, —NO$_2$, —SR$^{13}$, —SO$_3$R$^{13}$, —SO$_{n3}$OR$^3$, —SO$_{n3}$NR$^{13}$R$^{14}$, —NHNR$^{13}$R$^{14}$, —ONR$^{13}$RO$^{14}$, or —NHC(O)NHNR$^3$R$^4$. In embodiments, R$^{15}$, R$^{16}$, R$^{17}$, R$^{18}$, R$^{19}$, R$^{20}$, and R$^{21}$ are independently hydrogen, halogen, or —OH. R$^{15}$, R$^{16}$, R$^{17}$, R$^{18}$, R$^{19}$, R$^{20}$, and R$^{21}$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^{15}$, R$^{16}$, R$^{17}$, R$^{18}$, R$^{19}$, R$^{20}$, and R$^{21}$ are independently hydrogen, halogen, —OR$^3$, NR$^{13}$R$^{14}$, —CF$_3$, —NO$_2$, or substituted or unsubstituted alkyl. In embodiments, R$^{13}$ and R$^{14}$ are independently hydrogen, substituted or unsubstituted alkyl, or substituted or unsubstituted aryl. The symbol n3 may be 1. The symbol n3 may be 2.

In embodiments, if X$^4$ is an acid moiety, the acid moiety is —COOH (i.e. COO$^-$) or —SO$_3$H (i.e. SO$_3^-$). In embodiments, X$^4$ is —COOH (i.e. —COO$^-$). In embodiments, X$^4$ is —SO$_3$H (i.e. —SO$_3^-$). In embodiments, R$^{22}$ is —COOH (i.e. —COO$^-$). In embodiments, R$^{22}$ is —SO$_3$H (i.e. —SO$_3^-$).

The synthetic TGR5 triterpenoid agonist derivatives described herein may have the formula:

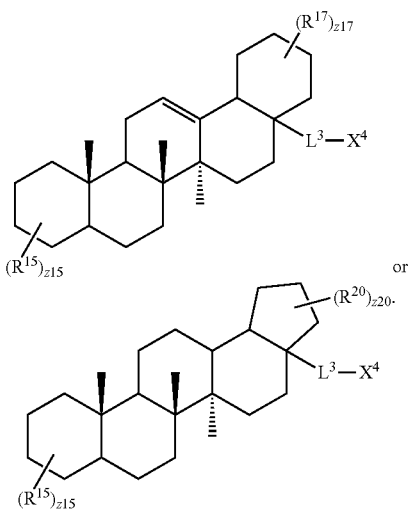

or

The synthetic TGR5 triterpenoid agonist derivatives described herein may have the formulae:

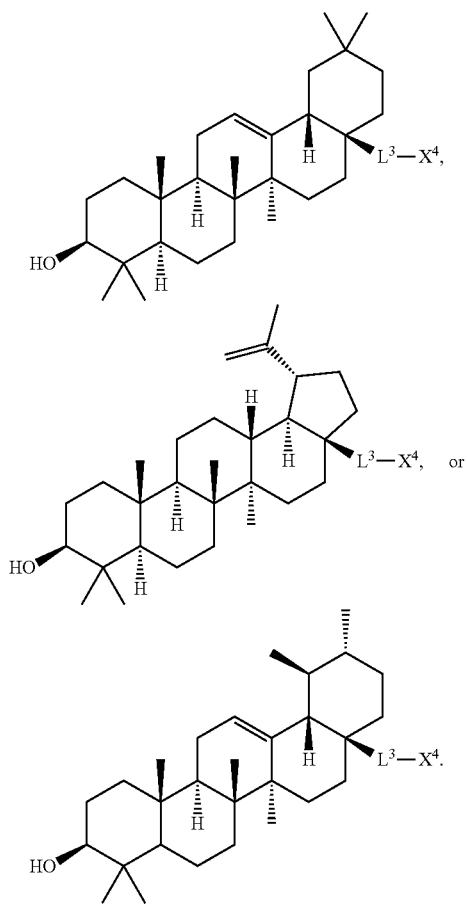

L³ and X⁴ are as described herein, including embodiments thereof.

In embodiments, the complexes described herein increase the solubility or bioavailability of metformin or a metformin analogue. Thus, in embodiments, the complexes described herein require a decreased amount of metformin or metformin analogue than metformin alone, to achieve the desired therapeutic result. In embodiments, the metformin-based TGR5 agonist complexes provided herein are agonists of TGR5 and lead to a rise in intracellular levels of cAMP.

II. Pharmaceutical Compositions

Also provided herein are pharmaceutical compositions containing the compositions and complexes described herein. Thus, in one aspect is a pharmaceutical composition that includes a metformin or metformin analogue as described herein, including embodiments, and a TGR5 ligand as described herein, including embodiments, together with a pharmaceutically acceptable excipient. In embodiments, the pharmaceutical composition includes a complex that includes metformin or metformin analogue as described herein, including embodiments, non-covalently bound to a TGR5 ligand as described herein, including embodiments. In embodiments, the metformin or metformin analogue and the TGR5 ligand form a salt.

In another aspect is a pharmaceutical composition that includes a complex that includes metformin or metformin analogue as described herein, including embodiments, non-covalently bound to a TGR5 ligand as described herein, including embodiments. The complex is as described herein. In embodiments, the metformin or metformin analogue and TGR5 ligand form a salt. Thus, in embodiments, the non-covalent bond is an ionic bond. In embodiments, the non-covalent bond is a hydrogen bond.

The metformin may be present at a therapeutically effective amount. The metformin may be present at therapeutically effective amount of less than about 3000 mg to less than about 10 mg. The metformin may be present at therapeutically effective amount of less than about 2500 mg to less than about 20 mg. The metformin may be present at therapeutically effective amount of less than about 2500 mg to less than about 30 mg. The metformin may be present at therapeutically effective amount of less than about 2500 mg to less than about 100 mg. The metformin may be present at therapeutically effective amount of less than about 2500 mg to less than about 500 mg. The metformin may be present at therapeutically effective amount of less than about 2500 mg to less than about 1000 mg.

The metformin may be present at therapeutically effective amount of less than about 3000, 2500, 2000, 1750, 1500, 1250, 1000, 800, 750, 500, 400, 350, 300, 250, 200, 175, 150, 125, 100, 75, 50, 40, 30, 20, or 10 mg. The metformin may be present at therapeutically effective amount of less than about 3000 mg. The metformin may be present at therapeutically effective amount of less than about 2500 mg. The metformin may be present at therapeutically effective amount of less than about 2000 mg. The metformin may be present at therapeutically effective amount of less than about 1750 mg. The metformin may be present at therapeutically effective amount of less than about 1500 mg. The metformin may be present at therapeutically effective amount of less than about 1250 mg. The metformin may be present at therapeutically effective amount of less than about 1000 mg. The metformin may be present at therapeutically effective amount of less than about 800 mg. The metformin may be present at therapeutically effective amount of less than about 750 mg. The metformin may be present at therapeutically effective amount of less than about 500 mg. The metformin may be present at therapeutically effective amount of less than about 400 mg. The metformin may be present at therapeutically effective amount of less than about 350 mg. The metformin may be present at therapeutically effective amount of less than about 300 mg. The metformin may be present at therapeutically effective amount of less than about 250 mg. The metformin may be present at therapeutically effective amount of less than about 200 mg. The metformin may be present at therapeutically effective amount of less than about 175 mg. The metformin may be present at therapeutically effective amount of less than about 150 mg. The metformin may be present at therapeutically effective amount of less than about 125 mg. The metformin may be present at therapeutically effective amount of less than about 100 mg. The metformin may be present at therapeutically effective amount of less than about 75 mg. The metformin may be present at therapeutically effective amount of less than about 50 mg. The metformin may be present at therapeutically effective amount of less than about 40 mg. The metformin may be present at therapeutically effective amount of less than about 30 mg. The metformin may be present at therapeutically effective amount of less than about 25 mg. The metformin may be present at therapeutically effective amount of less than about 20 mg. The metformin may be present at therapeutically effective amount of less than about 10 mg.

In embodiments, the therapeutically effective amount of metformin present in the pharmaceutical composition is about 5% lower than a metformin dose administered without being in a complex with a TGR5 ligand. The therapeutically effective amount of metformin present in the pharmaceutical composition may be about 10% lower than a metformin dose administered without being in a complex with a TGR5 ligand. The therapeutically effective amount of metformin present in the pharmaceutical composition may be about 20% lower than a metformin dose administered without being in a complex with a TGR5 ligand. The therapeutically effective amount of metformin present in the pharmaceutical composition may be about 25% lower than a metformin dose administered without being in a complex with a TGR5 ligand. The therapeutically effective amount of metformin present in the pharmaceutical composition may be about 30% lower than a metformin dose administered without being in a complex with a TGR5 ligand. The therapeutically effective amount of metformin present in the pharmaceutical composition may be about 40% lower than a metformin dose administered without being in a complex with a TGR5 ligand. The therapeutically effective amount of metformin present in the pharmaceutical composition may be about 50% lower than a metformin dose administered without being in a complex with a TGR5 ligand. The therapeutically effective amount of metformin present in the pharmaceutical composition may be about 55% lower than a metformin dose administered without being in a complex with a TGR5 ligand. The therapeutically effective amount of metformin present in the pharmaceutical composition may be about 60% lower than a metformin dose administered without being in a complex with a TGR5 ligand. The therapeutically effective amount of metformin present in the pharmaceutical composition may be about 70% lower than a metformin dose administered without being in a complex with a TGR5 ligand. The therapeutically effective amount of metformin present in the pharmaceutical composition may be about 75% lower than a metformin dose administered without being in a complex with a TGR5 ligand. The therapeutically effective amount of metformin present in the pharmaceutical composition may be about 80% lower than a metformin dose administered without being in a complex with a TGR5 ligand. The therapeutically effective amount of metformin present in the pharmaceutical composition may be about 85% lower than a metformin dose administered without being in a complex with a TGR5 ligand. The therapeutically effective amount of metformin present in the pharmaceutical composition may be about 90% lower than a metformin dose administered without being in a complex with a TGR5 ligand. The therapeutically effective amount of metformin present in the pharmaceutical composition may be about 95% lower than a metformin dose administered without being in a complex with a TGR5 ligand. The therapeutically effective amount of metformin present in the pharmaceutical composition may be about 96% lower than a metformin dose administered without being in a complex with a TGR5 ligand. The therapeutically effective amount of metformin present in the pharmaceutical composition may be about 97% lower than a metformin dose administered without being in a complex with a TGR5 ligand. The therapeutically effective amount of metformin present in the pharmaceutical composition may be about 98% lower than a metformin dose administered without being in a complex with a TGR5 ligand. The therapeutically effective amount of metformin present in the pharmaceutical composition may be about 99% lower than a metformin dose administered without being in a complex with a TGR5 ligand.

In embodiments, the complex of the metformin or metformin analogue and the TGR5 ligand renders the pharmaceutical composition more palatable than metformin administered alone. Thus, when formulated for oral administration as described herein, the patient may exhibit increased adherence compared to a patient administered metformin alone.

In embodiments, the complexes described herein can be formulated alone or in combination with one or more additional active agents. Thus, in embodiments of the pharmaceutical compositions, the pharmaceutical composition includes an additional agent in a therapeutically effective amount. The additional agent may be an anti-diabetes agent as described herein (e.g. pioglitazone, a sulfonylurea (e.g. glipizide or glibenclamide), a dipeptidyl peptidase-4 inhibitor (e.g. sitagliptin, saxagliptin), or a meglitinide (e.g. repaglinide)). In embodiments, the pharmaceutical compositions include two or more anti-diabetes agents. The additional agent may be an anti-cancer agent as described herein (e.g. Vincristine, Irinotecan, Vemurafenib, Paclitaxel, Cisplatin, Oxaliplatin, Carboplatin, Bevacizumab (AVASTIN®), Gefitinib, Pertuzumab, Trastuzumab, Ganitumab, Erlotinib, Letrozole, Lapatinib, Temozolomide, Gemcitabine, Capecitabine, Epirubicin, Fluorouracil, Temsirolimus, or Docetaxel (taxane)). In embodiments, the pharmaceutical compositions include two or more anti-cancer agents. The additional agent may be a cardiovascular disease treating agent (e.g. simvastatin, metoprolol, valsartan). Thus, the preparations can also be combined, when desired, with other active substances (e.g. to reduce metabolic degradation).

The complexes described herein can be formulated for transdermal administration, topical administration, or formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The complexes described herein may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The complexes described herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the complexes described herein can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles. Oral formulations herein may be formulated to reduce or minimize metallic taste or undesirable palatability commonly associated with metformin.

Pharmaceutical compositions provided by the present invention include compositions wherein the active ingredient (e.g. complexes described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, and/or reducing, eliminating, or slowing the progression of disease symptoms (e.g. symptoms of cancer, diabetes, or cardiovascular disease. Determination of a therapeutically effective amount of a compound of the invention is well within the capabilities of those skilled in the art, especially in light of the disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and complexes described herein. Adjustment and manipulation of established dosages (e.g., frequency and duration) are well within the ability of those skilled in the art.

For any complex described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state. Thus, using the teachings provided herein, an effective prophylactic or therapeutic treatment regimen can be planned that does not cause substantial toxicity and yet is effective to treat the clinical symptoms demonstrated by the particular patient. This planning should involve the careful choice of the complex, and combination with other therapies and agents as described herein, by considering factors such as compound potency, relative bioavailability, patient body weight, presence and severity of adverse side effects, preferred mode of administration and the toxicity profile of the selected agent.

III. Kits

Kits containing the compositions and pharmaceutical compositions described herein are also contemplated. In one aspect, the kit includes a first pharmaceutical composition that includes a metformin or metformin analogue and a pharmaceutically acceptable excipient, and a second pharmaceutical composition that includes a TGR5 ligand as described herein and a pharmaceutically acceptable excipient. The first and second pharmaceutical compositions may be supplied as a solution or as powders. The first and second pharmaceutical compositions may be stored within the same vessel/container or in separate vessels/containers. Accordingly, the first and second pharmaceutical compositions may be admixed to form the complexes described herein, including embodiments thereof.

In another aspect, the kit includes a metformin or metformin analogue, a TGR5 ligand as described herein, including embodiments, and a pharmaceutically acceptable excipient. The components (i.e. metformin or metformin analogue, TGR5 ligand, and pharmaceutically acceptable excipient) may be supplied as a ready-made solution or as powders. In embodiments, the components are supplied as powders. The powders may be supplied at predetermined amounts to facilitate easy dissolution at predetermined concentrations. The powders may be supplied in individual vessels/containers (i.e. each powdered component in a separate vessel/container) or may be supplied combined in any number of vessels/containers. Similarly, when the components are supplied as a ready-made solution, the solution may be supplied at a predetermined concentration. Each component may be provided separately in a separate solution. Alternatively, each component may provide in any number of solutions (i.e. at least two components supplied in one solution).

The kits described herein include the metformin or metformin analogue and the TGR5 ligand as a complex described herein. The metformin may be present at a therapeutically effective amount as described herein.

IV. Methods

Provided herein are methods of treating cancer. In one aspect, the method includes treating cancer in a subject in need thereof by administering a combined therapeutically effective amount of a metformin or metformin analogue as described herein and a TGR5 ligand as described herein.

The cancer may be a solid tumor. The cancer may be a cancer associated with hyperinsulinemia. The cancer may be melanoma, sarcoma, leukemia (e.g. acute lymphoblastic leukemia, chronic lymphocytic leukemia, acute myeloblastic leukemia), carcinoma (e.g. adenocarcinoma), lymphoma (e.g. Hodgkin Lymphoma, B-cell Lymphoma, Burkitt Lymphoma), brain cancer, head and neck cancer, thyroid cancer, kidney cancer, stomach cancer, pancreatic cancer, prostate cancer, peritoneal cavity cancer, fallopian tube cancer, endometrial cancer, lung cancer, non-small cell lung cancer, esophageal cancer, medulloblastoma, glioblastoma, lymphoma, colorectal cancer, gastric cancer, liver cancer, ovarian cancer or breast cancer. The cancer may be colorectal cancer, gastric cancer, liver cancer, ovarian cancer or breast cancer. The gastric cancer may be Her2 positive gastric cancer. The breast cancer may be Her2 positive breast cancer. The breast cancer may be triple-negative breast cancer.

In embodiments, the cancer is melanoma. In embodiments, the cancer is sarcoma. In embodiments, the cancer is leukemia (e.g. acute lymphoblastic leukemia, chronic lymphocytic leukemia, acute myeloblastic leukemia). In embodiments, the cancer is carcinoma (e.g. adenocarcinoma). In embodiments, the cancer is lymphoma (e.g. Hodgkin Lymphoma, B-cell Lymphoma, Burkitt Lymphoma). In embodiments, the cancer is brain cancer. In embodiments, the cancer is head and neck cancer. In embodiments, the cancer is thyroid cancer. In embodiments, the cancer is kidney cancer. In embodiments, the cancer is pancreatic cancer. In embodiments, the cancer is prostate cancer. In embodiments, the cancer is peritoneal cavity cancer. In embodiments, the cancer is fallopian tube cancer. In embodiments, the cancer is endometrial cancer. In embodiments, the cancer is lung cancer. In embodiments, the cancer is non-small cell lung cancer. In embodiments, the cancer is esophageal cancer. In embodiments, the cancer is medulloblastoma. In embodiments, the cancer is glioblastoma. In embodiments, the cancer is colorectal cancer. In embodiments, the cancer is gastric cancer. In embodiments, the cancer is liver cancer. In embodiments, the cancer is ovarian cancer. In embodiments, the cancer is breast cancer.

In embodiments, the cancer is refractory to anti-cancer agent treatment. In embodiments, the complexes described herein are co-administered with an anti-cancer agent. The anti-cancer agent is as described herein. The anti-cancer agent may be Vincristine, Irinotecan, Vemurafenib, Paclitaxel, Cisplatin, Oxaliplatin, Carboplatin, Bevacizumab (AVASTIN®), Gefitinib, Pertuzumab, Trastuzumab, Ganitumab, Erlotinib, Letrozole, Lapatinib, Temozolomide, Gemcitabine, Capecitabine, Epirubicin, Fluorouracil, Temsirolimus, or Docetaxel (taxane). The complexes herein may be co-administered with chemo-radiotherapy or Topoisomerase I Inhibitors. Such administration may also include administration of anti-cancer agents.

In embodiments the complexes herein may be administered to treat Li-Fraumeni Syndrome.

Also provided herein are methods of treating diabetes and its associated diseases. In one aspect is a method of treating diabetes in a subject in need thereof by administering a combined therapeutically effective amount of a metformin or metformin analogue as described herein and a TGR5 ligand as described herein. The subject may be a type 2 diabetes subject. In embodiments, the complexes described herein may be co-administered with anti-diabetes agents described herein. The anti-diabetes agent may be pioglitazone, a sulfonylurea (e.g. glipizide or glibenclamide), a dipeptidyl peptidase-4 inhibitor (e.g. sitagliptin, saxagliptin), or a meglitinide (e.g. repaglinide).

In another aspect is a method of treating metabolic disease associated with diabetes in a subject in need thereof by administering a combined therapeutically effective amount of a metformin or metformin analogue as described herein and a TGR5 ligand as described herein. In embodiments, the metabolic disease is hyperglycemia, insulin resistance, hyperinsulinemia, dyslipidemia, or hypertriglyceridemia. Thus, in certain aspects is a method of treating hyperglycemia, insulin resistance, hyperinsulinemia, dyslipidemia, or hypertriglyceridemia by administering a combined therapeutically effective amount of a metformin or metformin analogue as described herein and a TGR5 ligand as described herein. In embodiments, the dyslipidemia is hyperlipidemia. The hyperlipidemia may be hypercholesterolemia.

In another aspect is a method of treating hyperglycemia, insulin resistance, hyperinsulinemia, dyslipidemia, or hypertriglyceridemia in a non-diabetic patient by administering a combined therapeutically effective amount of a metformin or metformin analogue as described herein and a TGR5 ligand as described herein.

The methods also include methods of treating hypertension in a subject in need thereof by administering a combined therapeutically effective amount of a metformin or metformin analogue as described herein and a TGR5 ligand as described herein. The hypertension may be arterial hypertension. In embodiments, the complex described herein is coadministered with a blood pressure lowering agent such as a diuretic, beta blocker, ACE inhibitor, Angiotensin II receptor blocker, calcium channel blocker, alpha blocker, vasodilator, or combination thereof.

In yet another aspect is a method of treating fibrinolysis in a subject in need thereof by administering a combined therapeutically effective amount of a metformin or metformin analogue as described herein and a TGR5 ligand as described herein. In still another aspect is a method of treating endothelial dysfunction in a subject in need thereof by administering a combined therapeutically effective amount of a metformin or metformin analogue as described herein and a TGR5 ligand as described herein. In embodiments, the methods described herein are performed in a non-diabetic patient. The methods herein include a method of decreasing glycated hemoglobin (HbA1c) in a subject in need thereof by administering a combined therapeutically effective amount of a metformin or metformin analogue as described herein and a TGR5 ligand as described herein. Also provided is a method of reducing liver weight or kidney weight in a subject in need thereof by administering a combined therapeutically effective amount of a metformin or metformin analogue as described herein and a TGR5 ligand as described herein.

In another aspect, a method of treating fatty liver disease in a subject in need thereof is provided. The method includes administering a combined therapeutically effective amount of a metformin or metformin analogue and a TGR5 ligand as described herein. In embodiments, the fatty liver disease is nonalcoholic fatty liver disease.

The methods described herein may be useful in treating conditions associated with cardiovascular disease. Thus in one aspect is a method of reducing blood pressure in a subject in need thereof by administering a combined therapeutically effective amount of a metformin or metformin analogue as described herein and a TGR5 ligand as described herein. The subject may be a diabetic or non-diabetic patient. The reduction may be in systolic or diastolic blood pressure. In another aspect is a method of treating cardiovascular disease in a subject in need thereof by administering a combined therapeutically effective amount of a metformin or metformin analogue as described herein and a TGR5 ligand as described herein. The cardiovascular disease may be coronary heart disease, atherosclerosis, myocardial infarction, or atherothrombosis. In embodiments, the cardiovascular disease is in a diabetic patient (e.g. type 2 diabetic patient). In embodiments, the cardiovascular disease is in a non-diabetic patient. In embodiments, the complexes described herein are co-administered with a cardiovascular therapy agent. The cardiovascular therapy agent may be a diuretic, beta blocker, ACE inhibitor, Angiotensin II receptor blocker, calcium channel blocker, alpha blocker, vasodilator, or combination thereof.

The methods described herein may be useful in treating conditions associated with polycystic ovary syndrome. In one aspect is a method for treating polycystic ovary syndrome in a subject in need thereof by administering a combined therapeutically effective amount of a metformin or metformin analogue and a TGR5 ligand as described herein. In embodiments, the polycystic ovary syndrome is in a diabetic patient (e.g. type 2 diabetic patient). In embodiments, the polycystic ovary syndrome is in a non-diabetic patient. In embodiments, the complexes described herein are co-administered with an anti-PCOS agent. The anti-PCOS agent may be spironolactone, finasteride, progesterone, medroxyprogesterone, estradiol (e.g. ethinyl estradiol), levonorgestrel, elfornithine, clomiphen, and gonadotropins (e.g. luteinizing hormone and follicle-stimulating hormone). The anti-PCOS agent may be spironolactone. The anti-PCOS agent may be progesterone, medroxyprogesterone, estradiol (e.g. ethinyl estradiol), or levonorgestrel, or a combination therapy thereof.

The TGR5 ligand described in the methods herein may be a natural product TGR5 agonist or a synthetic TGR5 agonist derivative as described herein in the "compositions" section. Thus, the natural product TGR5 agonist may be a natural triterpenoid TGR5 agonist or a natural product bile acid as described herein. The synthetic TGR5 agonist derivative may be a synthetic TGR5 triterpenoid agonist derivative or a synthetic bile acid derivative as described by formula (V) or (VI), including embodiments thereof. In embodiments, the TGR5 ligand is a synthetic bile acid derivative described by formula (II), (III), or (IV) including embodiments thereof. In embodiments, the metformin or metformin analogue and the TGR5 ligand form a complex as described herein. The complex may be a salt that is formed between the metformin or metformin analogue and the TGR5 ligand.

The metformin may be present at therapeutically effective amount of less than about 3000 mg to less than about 10 mg. The metformin may be present at therapeutically effective amount of less than about 2500 mg to less than about 20 mg. The metformin may be present at therapeutically effective amount of less than about 2500 mg to less than about 30 mg. The metformin may be present at therapeutically effective amount of less than about 2500 mg to less than about 100 mg. The metformin may be present at therapeutically effective amount of less than about 2500 mg to less than about 500 mg. The metformin may be present at therapeutically effective amount of less than about 2500 mg to less than about 1000 mg.

The metformin may be present at therapeutically effective amount of less than about 3000, 2500, 2000, 1750, 1500, 1250, 1000, 800, 750, 500, 400, 350, 300, 250, 200, 175, 150, 125, 100, 75, 50, 40, 30, 20, or 10 mg. The metformin may be present at therapeutically effective amount of less than about 3000 mg. The metformin may be present at therapeutically effective amount of less than about 2500 mg. The metformin may be present at therapeutically effective amount of less than about 2000 mg. The metformin may be present at therapeutically effective amount of less than about 1750 mg. The metformin may be present at therapeutically effective amount of less than about 1500 mg. The metformin may be present at therapeutically effective amount of less than about 1250 mg. The metformin may be present at therapeutically effective amount of less than about 1000 mg. The metformin may be present at therapeutically effective amount of less than about 800 mg. The metformin may be present at therapeutically effective amount of less than about 750 mg. The metformin may be present at therapeutically effective amount of less than about 500 mg. The metformin may be present at therapeutically effective amount of less than about 400 mg. The metformin may be present at therapeutically effective amount of less than about 350 mg. The metformin may be present at therapeutically effective amount of less than about 300 mg. The metformin may be present at therapeutically effective amount of less than about 250 mg. The metformin may be present at therapeutically effective amount of less than about 200 mg. The metformin may be present at therapeutically effective amount of less than about 175 mg. The metformin may be present at therapeutically effective amount of less than about 150 mg. The metformin may be present at therapeutically effective amount of less than about 125 mg. The metformin may be present at therapeutically effective amount of less than about 100 mg. The metformin may be present at therapeutically effective amount of less than about 75 mg. The metformin may be present at therapeutically effective amount of less than about 50 mg. The metformin may be present at therapeutically effective amount of less than about 40 mg. The metformin may be present at therapeutically effective amount of less than about 30 mg. The metformin may be present at therapeutically effective amount of less than about 25 mg. The metformin may be present at therapeutically effective amount of less than about 20 mg. The metformin may be present at therapeutically effective amount of less than about 10 mg.

In embodiments, the therapeutically effective amount of metformin present in the methods described herein is about 5% lower than a metformin dose administered without being in a complex with a TGR5 ligand. The therapeutically effective amount of metformin present in the methods described herein may be about 10% lower than a metformin dose administered without being in a complex with a TGR5 ligand. The therapeutically effective amount of metformin present in the methods described herein may be about 20% lower than a metformin dose administered without being in a complex with a TGR5 ligand. The therapeutically effective amount of metformin present in the methods described herein may be about 25% lower than a metformin dose administered without being in a complex with a TGR5 ligand. The therapeutically effective amount of metformin present in the methods described herein may be about 30% lower than a metformin dose administered without being in a complex with a TGR5 ligand. The therapeutically effective amount of metformin present in the methods described herein may be about 40% lower than a metformin dose administered without being in a complex with a TGR5 ligand. The therapeutically effective amount of metformin present in the methods described herein may be about 50% lower than a metformin dose administered without being in a complex with a TGR5 ligand. The therapeutically effective amount of metformin present in the methods described herein may be about 55% lower than a metformin dose administered without being in a complex with a TGR5 ligand. The therapeutically effective amount of metformin present in the methods described herein may be about 60% lower than a metformin dose administered without being in a complex with a TGR5 ligand. The therapeutically effective amount of metformin present in the methods described herein may be about 70% lower than a metformin dose administered without being in a complex with a TGR5 ligand. The therapeutically effective amount of metformin present in the methods described herein may be about 75% lower than a metformin dose administered without being in a complex with a TGR5 ligand. The therapeutically effective amount of metformin present in the methods described herein may be about 80% lower than a metformin dose administered without being in a complex with a TGR5 ligand. The therapeutically effective amount of metformin present in the methods described herein may be about 85% lower than a metformin dose administered without being in a complex with a TGR5 ligand. The therapeutically effective amount of metformin present in the methods described herein may be about 90% lower than a metformin dose administered without being in a complex with a TGR5 ligand. The therapeutically effective amount of metformin present in the methods described herein may be about 95% lower than a metformin dose administered without being in a complex with a TGR5 ligand. The therapeutically effective amount of metformin present in the methods described herein may be about 96% lower than a metformin dose administered without being in a complex with a TGR5 ligand. The therapeutically effective amount of metformin present in the methods described herein may be about 97% lower than a metformin dose administered without being in a complex with a TGR5 ligand. The therapeutically effective amount of metformin present in the methods described herein may be about 98% lower than a metformin dose administered without being in a complex with a TGR5 ligand. The therapeutically effective amount of metformin present in the methods described herein may be about 99% lower than a metformin dose administered without being in a complex with a TGR5 ligand.

V. Examples

1. EXAMPLE 1

Novel metformin-based TGR5 agonist complexes (proton transfer complexes or salts) are described herein which may act as anti-diabetic and anti-cancer agents. These complexes may significantly impact the type 2 diabetes and cancers to targeted therapy (glucose homeostasis). These novel TGR5 agonists are evaluated in vitro by using luciferase-based reporter and cAMP assays and in vivo in male diabetic db/db mice model to elucidate their biological properties. The metformin-based TGR5 agonist complexes provided herein may be agonists of TGR5 and lead to a rise in intracellular levels of cAMP. These complexes could enhance the absorption of metformin in the intestine and improve the bioavailability of metformin. These complexes may provide an important addition to the range of medicines to enhance metformin efficacy. Indeed, the novel metformin-based TGR5 complexes herein could be employed individually or in combination with other anti-diabetic or anti-cancer agents for treating the targeted metabolic syndrome or cancers.

The present invention relates to metformin-based TGR5 complexes (e.g. salts) of the anti-diabetic agent metformin. In particular, it was discovered herein that the TGR5 ligands (e.g. agonists) form complexes with metformin. TGR5 ligands include the bile acid and their novel derivatives, or natural TGR5 agonists such as oleanolic acid (OA), betulinic acid (BA), and ursolic acid (UA), preferably TGR5 bile acid agonistic or TGR5 natural agonistic organic carboxylic acids, optionally in combination with other anti-diabetic agent and to a method employing such complexes for targeted metabolic therapy to treat diabetes or cancers. Using these metformin-based TGR5 ligand complexes specifically could maintain glucose homeostasis in patients and reduce the dosage of metformin—representing attractive strategies in the development of treatment against metabolic diseases and cancers. Further, this strategy might offer physicians another valuable treatment choice in the management of targeted progressive diseases.

The TGR5 agonists forming the complexes (e.g. salts) with metformin preferably include an organic carboxylic acid which includes saturated TGR5 bile acid agonists and TGR5 natural or synthetic agonists such as UDCA, 6EUDCA, CA, 6ECDCA, 23(S)-methyl-UDCA, and tauro- and glycol-form carboxylic acids such as tauro-UDCA, tauro-CA, glycol-UDCA, glycol-CA, and others as described herein. Described herein are complexes (e.g. salts) of metformin in a 1:1 stoichiometric (molar ratio) with a TGR5 ligand as described herein and complexes (e.g. salts) of metformin in a 1:1 stoichiometric (molar ratio) with a TGR5 natural agonists oleanolic acid, betulinic acid (BA), and ursolic acid.

Diabetes mellitus is now a major health epidemic and is categorized into two subclasses: type 1, known as insulin dependent diabetes mellitus (IDDM), and type 2, noninsulin dependent diabetes mellitus (NIDDM).[1] Type 2 diabetes is a chronic and progressive metabolic disorder of carbohydrate and lipid metabolism and accounts for the nearly 90% of diabetes mellitus and results from impaired insulin secretion and reduced peripheral insulin sensitivity—a burgeoning, worldwide health problem affecting almost twenty-six million people in the United States.[2] Current oral therapies of this disease are limited by availability of effective medications, including insulin secretagogues, such as sulfonylureas; activators of the peroxisome proliferator-activated receptor-γ (PPAR-γ), such as the thiazolidinediones; and effectors of the glucose-lowering, exemplified with metformin. Indeed, all of the existing oral hypoglycemic agents have subsequent failure after long term administration. Deficiencies associated with currently available treatments include hypoglycemic episodes, weight gain, gastrointestinal problems, edema, and loss of responsiveness over time.

Recent efforts have been made to improve therapies targeting the variety of pathways involved in diabetes and prediabetic insulin resistance in the metabolic syndrome, and to promote continued exploration of alternative targets involved in maintenance of glucose homeostasis. Two bile acid activated receptors were identified—the nuclear farnesoid-X receptor (FXR) in 1995,[3] and the G protein coupled receptor (GPCR) TGR5 in 2002.[4] FXR and TGR5 were demonstrated to have roles in the regulation of the intricate network governing lipid, cholesterol, glucose homeostasis and energy homeostasis, the transport and metabolism of fatty acids and triglycerides.[5] Thus, FXR and TGR5 emerged as possible biological targets for the treatment of diabetes and associated metabolic disorders and cancers.

Bile acids are signaling molecules with systemic endocrine functions and have long been known to play a central role in the digestive process. They are well known for their role in the solubilization of lipid-soluble nutrients due to their hydrophilic/hydrophobic balance. Bile acids are amphiphilic molecules, which influences their organization in solution, and presumably plays a role in their ability to promote the absorption of polar drugs across membranes. Recent research indicated that bile acids are the purported endogenous agonists for TGR5 and FXR.[6] Through signaling effects at FXR and TGR5 receptors, bile acids may regulate a number of cellular processes including those related to their own enterohepatic circulation, but also processes relevant to glucose, cholesterol, and triglyceride metabolism. TGR5 mediates several non-genomic functional responses induced by binding of bile acids.[7]

TGR5 is a member of the rhodopsin-like subfamily of G-protein-coupled receptor GPCRs and is expressed in liver, skeletal muscle, brown adipose tissues, monocytes and signaling in the Kuppfer cells.[8] TGR5 has been found to be expressed on the surface of enteroendocrine L-cells in the distal intestine that these cells secrete GLP-1. It was also found on the surface of other putative incretins such as PYY. Activation of the TGR5 receptor upon ligand binding results in $G\alpha_s$-coupled activation of adenylate cyclase. The subsequent downstream signaling cascade may drive multiple effects that are cell type-dependent including, for example, enhanced glucagon-like peptide-1 (GLP-1) release from intestinal cells. This offers improved glycemic control through potentiation of glucose-dependent insulin secretion.[9] Moreover, the secretion of GLP-1 and PYY in these cells is induced by agonism of TGR5 via a signaling pathway using cAMP (cyclic adenosine 5'-monophosphate). Agonism of the TGR5 receptor thus likely leads to cAMP production, which in turn likely leads to an increase in circulating GLP-1 and other possibly beneficial incretins. In vivo data from diabetic and obesity animal models demonstrate that beneficial therapeutic effects are observed following activation of TGR5.[10] Medicines causing elevated GLP-1 have been pursued as anti-diabetic agents. More recently, the use of a GLP-1 receptor agonist peptide in clinical treatment has been approved by FDA. Thus medicines that are peptide analogs of GLP-1 or increase GLP-1, e.g. DPP-IV inhibitors, have proved beneficial.[11] However, despite these available therapies, the incidence of diabetes has continued to increase as described above, since therapies are severely limited by parenteral administration and low in vivo stability.[12] Collectively, there is a distinct and pressing need for new diabetic medications. Agonism of TGR5 receptor provides one strategy towards that end. Accordingly, identification of small molecule agonists of TGR5 is of high interest. For these reasons, TGR5 agonists may be useful agents not only to treat diabetes with concurrent management of glucose levels and body weight but also potentially address other aspects of metabolic syndrome.

To find a suitable candidate for TGR5 clinical studies, a number of bile acid derivatives and natural products of TGR5 agonists have been disclosed. Several potent and selective TGR5 agonists with in vitro activity have been evaluated (See e.g. U.S. application Ser. No. 14/159,995). These results demonstrated TGR5 agonists are useful for treating diabetes and other metabolic disorders where activation of the TGR5 receptor is beneficial.

More than 70% of diabetics use some sort of pharmaceutical therapy. Example therapies currently include metformin hydrochloride (glucose lowering agent, (N,N dimethylbiguanidinium chloride).[14] Metformin is one of potent anti-diabetic agent used as a first-line treatment for patients with type II diabetes, in particular, in overweight and obese patients. Oral absorption of metformin is variable and incomplete. Metformin has an oral bioavailability of 50-60% under fasting conditions, and is absorbed slowly. Peak plasma concentrations ($C_{max}$) are reached within one to three hours of taking immediate-release metformin. The plasma protein binding of metformin is negligible, as reflected by its very high apparent volume of distribution (300-1000 L after a single dose). Steady state is usually reached in one or two days and metformin is not metabolized. It is cleared from the body by tubular secretion and excreted unchanged in the urine. Metformin is undetectable in blood plasma within 24 hours of a single oral dose and has an average elimination half-life in plasma is 6.2 hours. Metformin is distributed to (and appears to accumulate in) red blood cells, with a much longer elimination half-life: 17.6 hours (reported as ranging from 18.5 to 31.5 hours in a single-dose study of non-diabetic people). Metformin is highly basic (pKa about 12.4) and is fully protonated under physiological conditions. Thus, metformin is slowly and incompletely absorbed.

The currently marketed metformin hydrochloride salt was approved by the United States Food and Drug Administration (FDA) in 1995 as an oral hypoglycemic agent. Metformin may be administered as an immediate-release or extended-release formation. Given alone or in combination with a sulfonylurea and insulin, metformin reduces hyperglycemia. In addition, metformin is known to increase circulating GLP-1 levels. Further aspects of metformin pathway still remain poorly understood.

Type 2 diabetes is strongly correlated with obesity, a central component of the metabolic syndrome, and cancer. In addition, the burden of diabetes is driven by vascular complications such as cardiovascular disease. Hyperglycemia appears central to both the vascular consequences of diabetes and the progressive nature of the disease itself.[16] Recent studies showed incremental reductions in glycosylated hemoglobin (HbA1C), a marker of protein glycation, lowered the risk of diabetes-related events, including myocardial infarction and microvascular complications. Thus, reducing HbA1C values to <7% has become the recommended standard for patients with Type 2 diabetes. Metformin can decrease the level of HbA1c by about 1-2%. Because the medication does not increase the amount of insulin produced by the body, it is less likely to cause dangerously low blood sugar (hypoglycemia), as many other diabetes medications can do.

However, the poor bioavailability of metformin HCl (only ~50%) requires large effective doses. When combined with a rapid kidney excretion,[17] the administration of metformin commonly results uncomfortable gastrointestinal adverse effects at effective doses (0.5-2.5 g per day). These gastrointestinal adverse effects include abdominal discomfort and pain, nausea, vomiting, diarrhea, anorexia, metallic taste, and raising the risk of lactic acidosis. The metallic taste, in many instances, discourages proper use by both children and adults due to poor palatability.

Metformin recently emerged as a potential anticancer agent. Small studies in cancer patients with or without diabetes suggest metformin may benefit in lowering insulin levels. The ability of metformin to lower circulating insulin may be particularly important for the treatment of cancers, including for example, those known to be associated with hyperinsulinemia (e.g. breast and colon cancer). Epidemiological, preclinical and clinical evidence supports the use of metformin as a cancer therapeutic. Moreover, metformin may exhibit direct inhibitory effects on cancer cells by, without being bound by any particular theory, inhibiting mammalian target of rapamycin (mrTOR) signaling and protein synthesis. The large doses of metformin required for treatment discourage its use due to high incidence of gastrointestinal disturbance such as diarrhea.[19]

We hypothesized, without being bound by any particular theory, that metformin/TGR5 ligand complexes might be represent an alternative strategy to overcome the drawbacks of metformin therapy discussed herein. These complexes could improve lipophilicity and enhance intestinal absorption to levels greater than the metformin hydrochloride alone. Thus, the complexes increase both the bioavailability of metformin and its efficacy.

We hypothesized, without being bound by any particular theory, that a pharmaceutical composition containing a metformin/TGR5 ligand complex in which metformin could be conjugated to the TGR5 agonist chosen from natural or synthetic TGR5 agonists. These complexes could reduce side effects of metformin, especially uncomfortable gastrointestinal adverse effects, also could improve taste properties as compared to the hydrochloride salt thus enhancing patient compliance, and finally, enhance the efficacy of metformin.

The incorporation of positive charge of metformin into, for example, a TGR5 bile acid or its synthetic derivatives has been investigated in this study. The behavior and properties of metformin-based TGR5 agonist complexes act in TGR5 activation and may raise new possibilities for the delivery of hydrophilic metformin across membrane barriers to enhance its efficacy. Thus, the complexes described herein represent an important step toward identification of more effective options to treat diabetes and cancers.

2. EXAMPLE 2

We designed, synthesized, and evaluated a class of metformin-based TGR5 agonist complexes to evaluate how increasing the efficacy of metformin affects its drug effective. The methodology employs conventional and traditional salt forming procedures. Thus, for example, the complex was prepared in a straightforward manner by a transformation of metformin HCl to free base by using NaOH (sodium hydroxide) or KOH (potassium hydroxide) in ethanol or isopropyl alcohol or other suitable solvent. Treatment of the free base with a natural or synthetic derivative TGR5 agonist resulted in the production of metformin TGR5 agonist complexes. We also used alternative preparations of complexes using a series of sodium salts of bile acid and their derivatives in methanol or other suitable solvent with metformin hydrochloride. The reaction mixture was stirred at room temperature overnight, after work-up, solidified with EtOAc to obtain complexes with adequate yields. The desired metformin-based TGR5 agonist complex could be recovered by filtration, and dried to form a colorless solid (in a 1:1 molar ratio metformin:TGR5 agonist).

These complexes was evaluated in vitro and in vivo. The complexes enhanced the efficacy of metformin and improved the lipophilicity and the oral drug bioavailability of metformin using this strategy.

A comparison of metformin-based TGR5 bile acid complexes suggests several factors may be involved in the success of such complexes. We reasoned bile acids and their derivatives, as applied to metformin, were not only transport enhancer agents but also activated cell surface receptor TGR5. Such activation may make the complexes more effective than the components alone. Additionally, as described above, metformin is fully protonated under physiological conditions and is therefore slowly and incompletely absorbed from the upper intestine after oral administration. This may lead to toxicity related to lactic acidosis. In contrast, the complexes avoid protonation of metformin because the hydrophilic positively charged of metformin is protonated by TGR5 ligand of the complex. Thus, the complexes enhance the absorption and the risk of lactic acidosis should be irrelevant.

The potential efficacy of the different bile acid related compounds from their ability to increase the intranasal absorption of insulin in rats has been judged.[20] We reasoned, without being bound by any particular theory, that the lipophilicity of the complexes herein has been increased by, at least in part, creating an extensive lipid surface of TGR5 agonists. The increased lipophilicity resulted in enhanced oral absorption of metformin. Additionally, the activation of TGR5 via metformin-based TGR5 agonist complex increases the hydrophobic surface and increases absorption of insulin into the circulation. According to our in vitro and in vivo data, these more lipophilic metformin-based TGR5 agonist complexes could greatly enhance the absorption compared with metformin itself, yielding greater bioavailability and efficacy of metformin. One advantage of this complex approach is that the lipophilicity appears to be a critical parameter in improving efficacy of metformin and plays a role in the determinant of transport activity. The TGR5 ligand also plays an important role in the transfer of hydrophilic metformin across membranes.

The combinations of metformin and PPARγ and PPARα agonists have been suggested recently.[22] The combination is intended to reduce hyperglycemia. However, unlike TGR5 ligands described herein, PPAR agonists have potential side-effect especially for weight gaining. TGR5 ligands are also shown to benefit type 2 diabetes and dyslipidemia, particularly in the glucose homeostasis. So the metformin-complex may be particularly useful in cases involving both of type 2 diabetes, dyslipidemia, and possibly cardiovascular disease.[23] We have shown in vitro that metformin is not a ligand for the TGR5. Thus, the TGR5 ligand may activate the TGR5 receptor. The complexes were evaluated in vitro using luciferase-based reporter and cAMP assays to elucidate their biological properties. Surprisingly, the complexes are agonists of TGR5 and lead to a rise in intracellular levels of cAMP (See FIG. 5). Thus, the design of the complexes appears to result in synergy between metformin and the TGR5 ligand—that the whole complex has more than an additive effect from its component parts.

Figure 8:
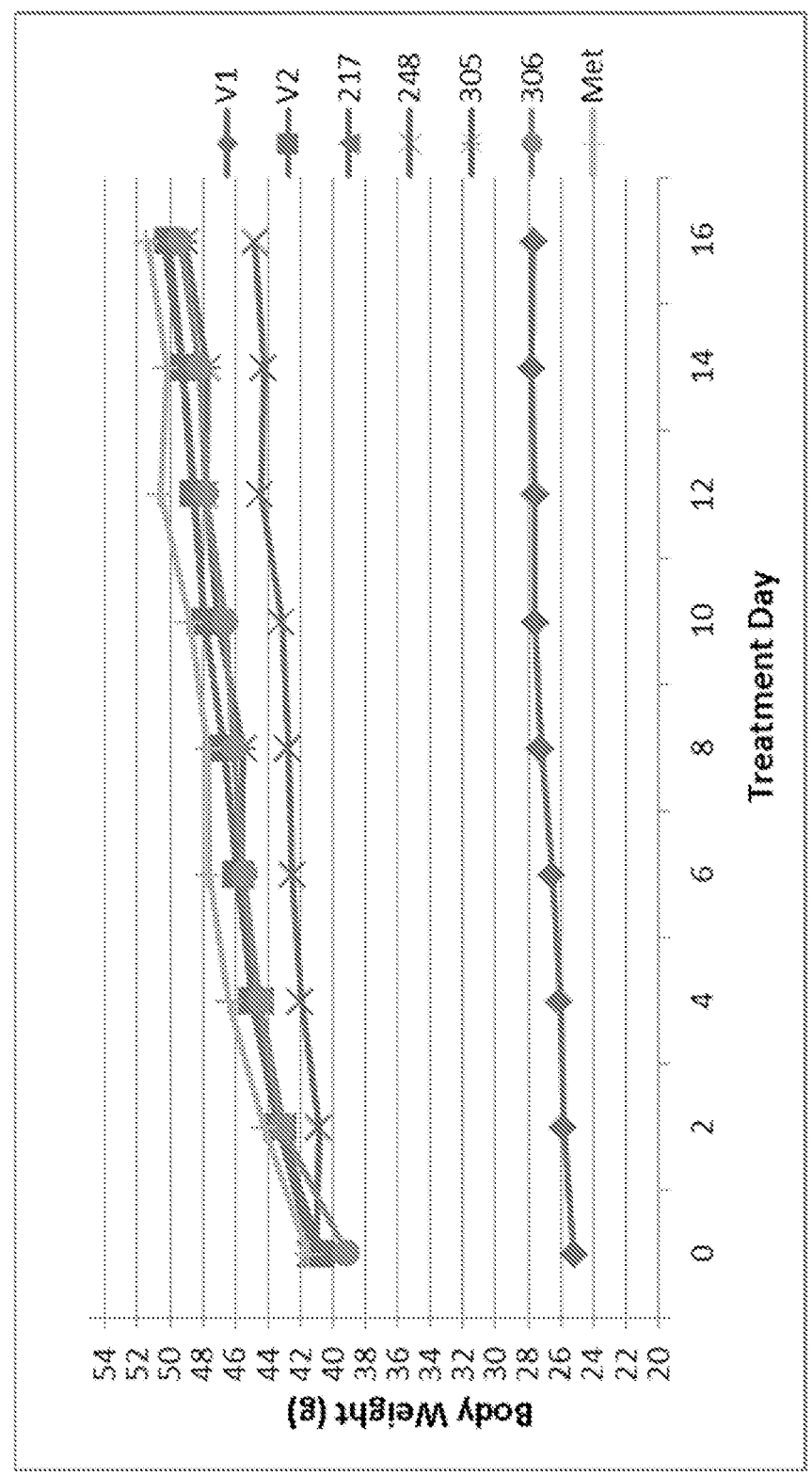
FIG. 8 Effect on body weight of administration of ligand and complex administered daily for 5 weeks in db/db mice (seven per group), with vehicle controls. (V1=vehicle 1 (Lean, Non-diabetic mice): V2=Vehicle 2 (Obese, Diabetic mice): 217=6α-ethyl CDCA; 248=6α-ethyl UDCA; 305=metformin/6α-ethyl CDCA complex; 306=metformin/ 6α-ethyl UDCA complex; Met=metformin).
Figure 9:
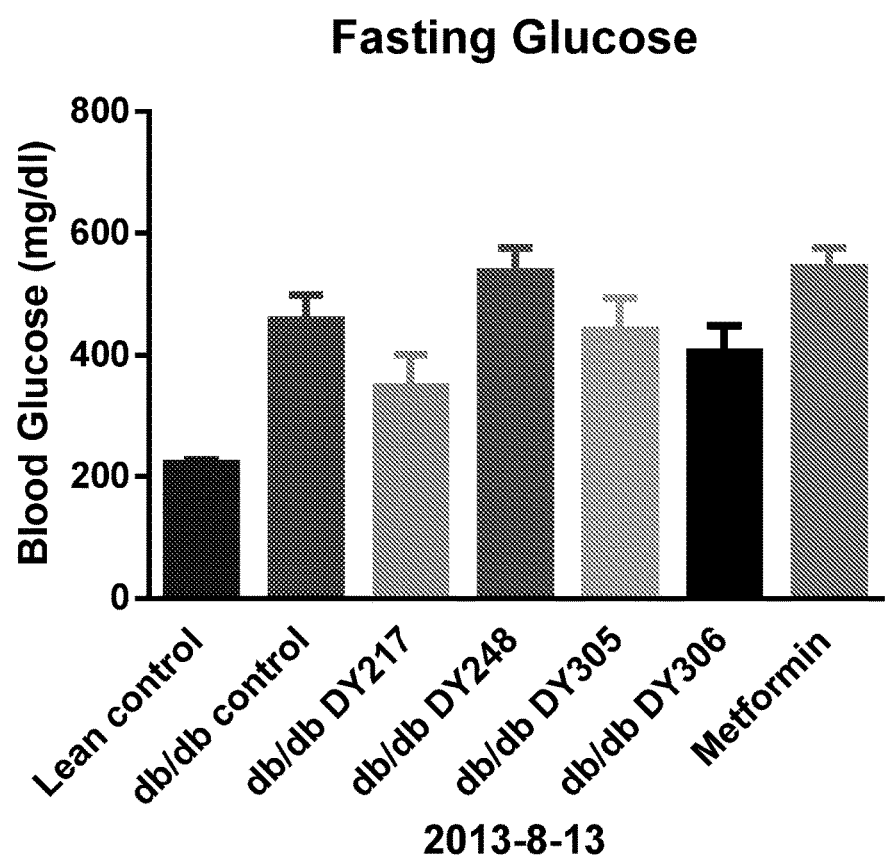
FIG. 9. Histogram depicting effect of metformin-based TGR5 complexes on fasting glucose levels: complexes and ligands were tested in high glucose db/db mice at a lower dose of 30 mg/kg of body weight administered daily for 5 weeks; the metformin-based TGR5 agonist complexes DY305 and DY306 caused a decline in the fast blood glucose by ~10-25% as compared to the vehicle-treated control db/db mice (30 mg/kg BW, 0.057 mmol of metformin-based TGR5 agonist complexes, and 250 mg/kg BW, 1.52 mmol of metformin). (Lean=no metformin or agonist, Non-diabetic mice; db/db=no metformin or agonist, Obese Diabetic mice; db/db DY217=no metformin and 30 mg 6α-ethyl CDCA in db/db mice treatment; db/db DY248=no metformin and 30 mg 6α-ethyl UDCA in db/db mice treatment; db/db DY305=30 mg total complex (metformin and DY217(6α-ethyl CDCA)) corresponding to 1:1 stoichiometry in db/db mice; db/db DY306=30 mg total complex (metformin and DY248(6α-ethyl UDCA)) corresponding to 1:1 stoichiometry in db/db mice; Metformin—250 mg metformin in db/db mice treatment). Legend: x-axis (histogram columns left to right): lean control, db/db control, db/db DY217, db/db DY248, db/db DY305, db/db DY306, metformin; y-axis: blood glucose (mg/dl).
Figure 10:
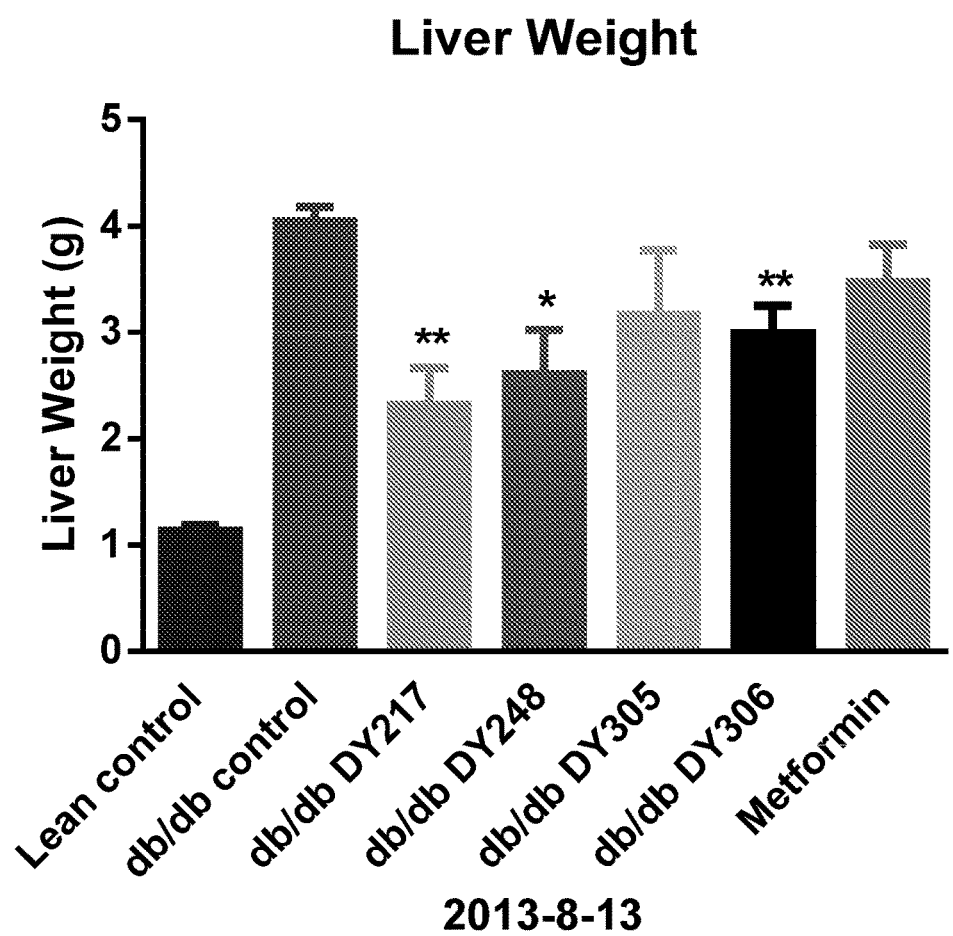
FIG. 10 Histogram depicting effect of metformin-based TGR5 complexes on liver weight: The metformin-based TGR5 agonist complexes were tested in high glucose db/db mice at a lower dose of 30 mg/kg of body weight administered daily for 5 weeks. The metformin-based TGR5 agonist complexes DY305 and DY306 caused a decline in the liver weight by ~5-10% as compared to the vehicle-treated control db/db mice (30 mg/kg BW metformin-based TGR5 agonist complexes, 250 mg/kg BW metformin). The dose of the metformin-based TGR5 agonist complex DY306 (30 mg, 0.057 mmol) via i.p. injection was 3% of that of metformin (250 mg, 1.52 mmol), assumed that the metformin-based complex DY305 and DY306 would be absorbed more efficiently than metformin. (Lean=no metformin or agonist, Non-diabetic mice; db/db=no metformin or agonist, Obese Diabetic mice; db/db DY217=no metformin and 30 mg 6α-ethyl CDCA in db/db mice treatment; db/db DY248=no metformin and 30 mg 6α-ethyl UDCA in db/db mice treat; db/db DY305=30 mg total complex (metformin and DY217(6α-ethyl CDCA)) corresponding to 1:1 stoichiometry in db/db mice; db/db DY306=db/db DY306=30 mg total complex (metformin and DY248(6α-ethyl UDCA)) corresponding to 1:1 stoichiometry in db/db mice; Metformin—250 mg metformin in db/db mice treatment). Legend: x-axis (histogram columns left to right): lean control, db/db control, db/db DY217, db/db DY248, db/db DY305, db/db DY306, metformin; y-axis: liver weight (g).
Figure 11:
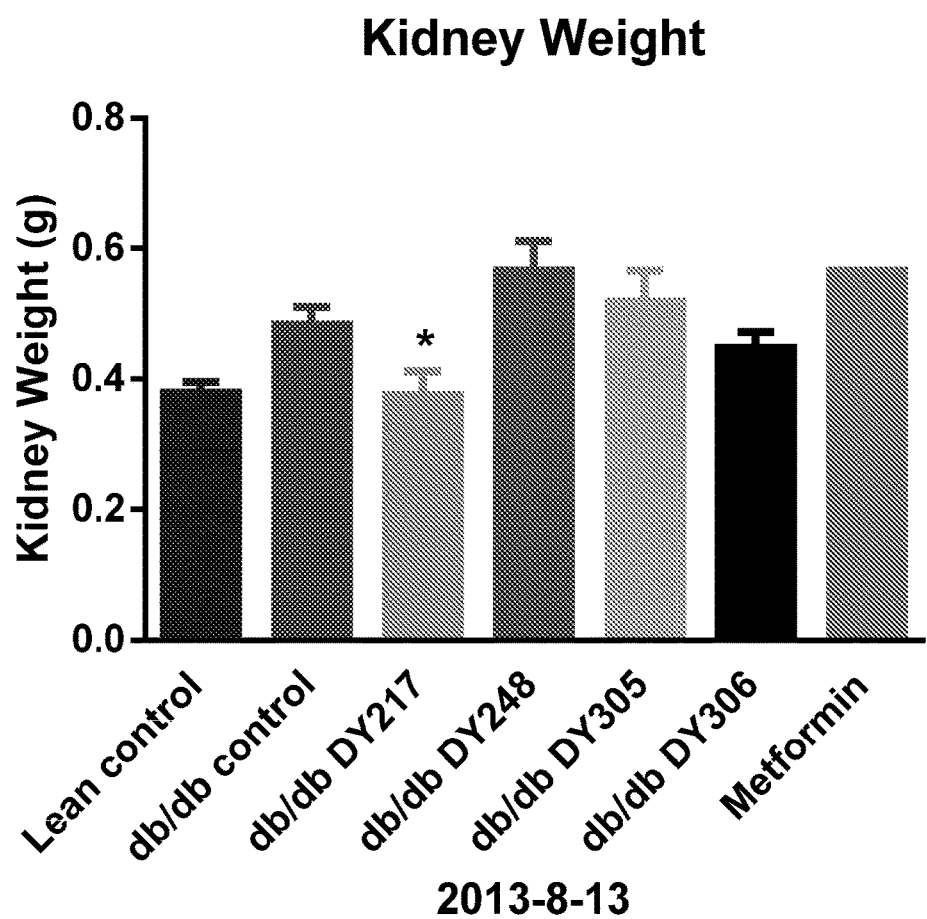
FIG. 11 Histogram depicting effect of metformin-based TGR5 complexes on kidney weight: The metformin-based TGR5 agonist complexes were tested in high glucose db/db mice at a lower dose of 30 mg/kg of body weight administered daily for 5 weeks. The metformin-based TGR5 agonist complexes DY305 and DY306 caused a decline in the kidney weight by ~5-20% as compared to the vehicle-treated control db/db mice (30 mg/kg BW metformin-based TGR5 agonist complexes, 250 mg/kg BW metformin). The dose of the metformin-based TGR5 agonist complex DY306 (30 mg, 0.057 mmol) via i.p. injection was 3% of that of metformin (250 mg, 1.52 mmol), assumed that the metformin-based complex DY305 and DY306 would be absorbed more efficiently than metformin. (Lean=no metformin or agonist, Non-diabetic mice; db/db=no metformin or agonist, Obese Diabetic mice; db/db DY217=no metformin and 30 mg 6α-ethyl CDCA in db/db mice treatment; db/db DY248=no metformin and 30 mg 6α-ethyl UDCA in db/db mice treat; db/db DY305=30 mg total complex (metformin and DY217(6α-ethyl CDCA)) corresponding to 1:1 stoichiometry in db/db mice; db/db DY306=db/db DY306=30 mg total complex (metformin and DY248(6α-ethyl UDCA)) corresponding to 1:1 stoichiometry in db/db mice; Metformin—250 mg metformin in db/db mice treatment). Legend: x-axis (histogram columns left to right): lean control, db/db control, db/db DY217, db/db DY248, db/db DY305, db/db DY306, metformin; y-axis: kidney weight (g).

Our in vivo data indicated the daily doses of metformin could be reduced (metformin alone is taken up to a maximal daily human dosage of over 2 g). Metformin is known to be absorbed via saturable paracellular route.[25] Absorption of the more lipophilic complexes was likely increased in part due to passive transcellular diffusion via TGR5 activation. For example, the dose of the complex DY306 (30 mg, 0.057 mmol) via i.p. injection required only 3% of the standard dose of metformin (250 mg, 1.52 mmol) (FIG. 8). Thus, the complexes appear to be better absorbed from the gastrointestinal tract than metformin alone. This avoids many of the unwanted gastrointestinal adverse effects associated with metformin. Further, the results indicate the daily doses of metformin could be reduced by upwards of at least 50%.

The complexes described herein bind and activate TGR5. They are therefore useful for treating diseases and disorders where activation of the TGR5 receptor is beneficial such as type 2 diabetes, metabolic syndrome, obesity, dyslipidemia, inflammatory diseases (chronic and acute), and hypercholesterolemia, and cancers.

The dual actions of anti-obesity and anti-diabetic properties on the TGR5 make its agonists an attractive choice for the development of drugs for treating diabetes and related metabolic disorders. The in vivo efficacies of active complexes were comparable to that exerted by metformin in HbA1c, blood glucose and HOMA index, but required significantly lower metformin doses. The preliminary results indicate that the novel complexes could serve as potential drug candidates to promote the bioavailability of metformin and clinical usefulness for treating diabetes and cancers.

3. EXAMPLE 3

A series of metformin/TGR5 ligand complexes was designed, synthesized, and characterized by $^1$H and $^{13}$C NMR spectroscopy, and combustion analysis. These complexes were prepared in a by a transformation of metformin HCl to free base—achieved using NaOH or KOH in ethanol or isopropyl alcohol. Treatment of the free base with bile acids or natural TGR5 agonists resulted in the production of twenty-five metformin-based TGR5 agonist complexes. The preparations of complexes can be made by a series of sodium salts of bile acid and their derivatives in methanol with metformin hydrochloride. The reaction mixture was stirred for overnight at room temperature, after work-up, solidified with EtOAc to obtain the complexes. The reaction between metformin and TGR5 ligands using a 1:1 molar ratio was performed to prepare the colorless final complex. The melting points of complexes are different from starting materials, i.e. the metformin and the respective TGR5 ligand. Both $^1$H NMR and elemental analysis correspond to a 1:1 stoichiometry. The molecular structures of metformin-based TGR5 agonist complexes are represented in FIGS. 1-5. Further details of the individual complex are listed in Table 1. The molecular structures of exemplary metformin-based TGR5 bile acid complexes are represented in FIG. 1. The complex formation was completed using the reaction described.

The tauro-form and glyco-form of metformin-based TGR5 bile acid agonist complexes can be prepared by coupling metformin hydrochloride to a series of sodium tauro-bile acid and sodium glyco-bile acid or sodium forms directly via a reaction in methanol or other suitable solvent. See FIG. 2 and FIG. 3).

Oleanolic acid (OA), betulinic acid (BA), and ursolic acid (UA) (FIG. 4), the most commonly studied triterpenoids, exhibit modest biological activity along. These natural TGR5 agonists belong to the bioactive phytochemical terpenoids which are ubiquitous triterpenoids in plant kingdom, medicinal herbs, and are integral part of the human diet. Indeed, OA has been marketed in China as an oral drug for the treatment of liver disorders in humans. Since metformin possesses poor cell penetration and poor absorption in the intestine, it has limited its bioavailability in the body. Accordingly, complexes including metformin or metformin analogues and the TGR5 agonists OA, BA, and UA could not only improve lipophilicity and enhance intestine absorption but also increase the bioavailability of metformin. These complexes may reduce the required daily doses of metformin, and therefore decrease the uncomfortable adverse effects associated with metformin therapy. In addition, the complexes increase the solubility of metformin.

Figure 5:
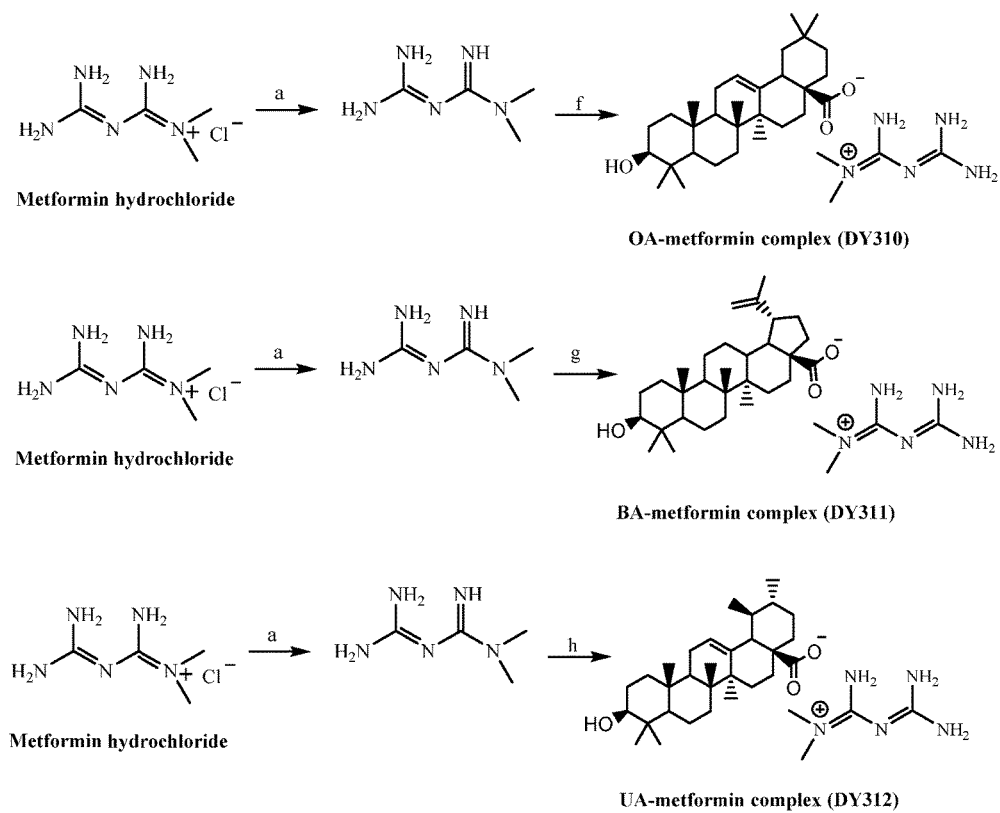
FIG. 5 Synthesis of metformin-based TGR5 natural product OA, BA, and UA complexes, reaction conditions: (a) NaOH/MeOH; (f) OA, n-butanol, reflux 12 h (g), BA, n-butanol, reflux 12 h, and (h), UA, n-butanol, reflux 12 h.
Figure 7A:
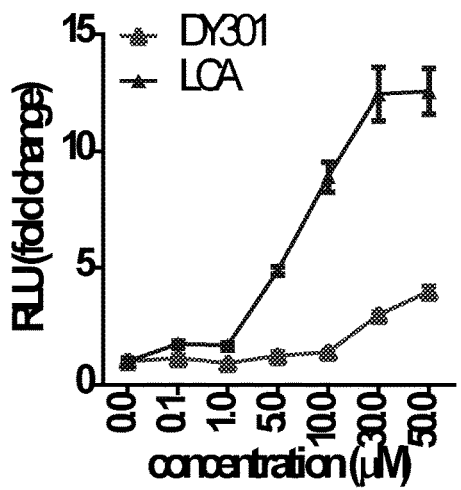
FIGS. 7A7F. HEK293 overexpressing TGR5 cells were transfected 100 ng pCRE-luc reporter along with 10 ng pCMV-beta-galactosidase by HiPerfect (Qiagen). 24 hours post transfection, cells were treated with vehicle (DMSO) and appropriate ligand or complex as indicated. Luciferase- and beta-gal activities were assayed 24 hours later. (DY301=metformin/CA complex; DY302=metformin/ UDCA complex; DY306=metformin/6α-ethyl UDCA complex; DY 305=metformim/6α-ethyl CDCA complex; DY310=metformin/oleanolic acid complex). Legend.
Figure 7B:
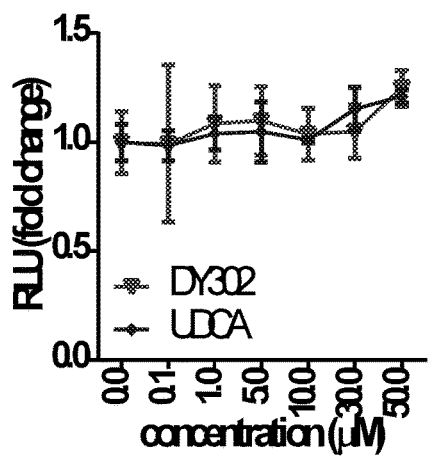
FIG. 7B: DY302 and UDCA.
Figure 7C:
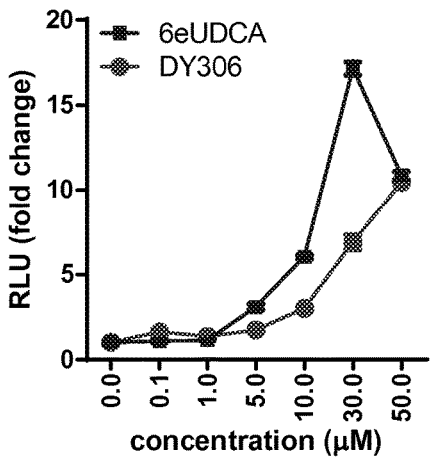
FIG. 7C: DY306 and 6eUDCA.
Figure 7D:
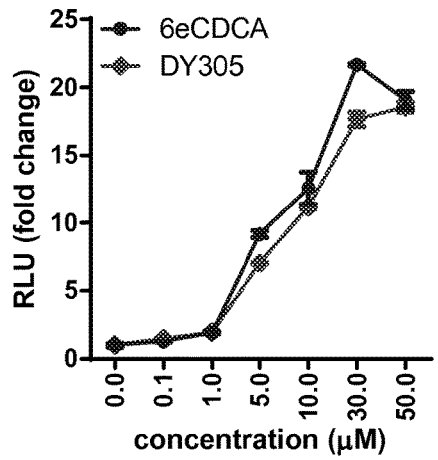
FIG. 7D: 6eCDCA and DY305.
Figure 7E:
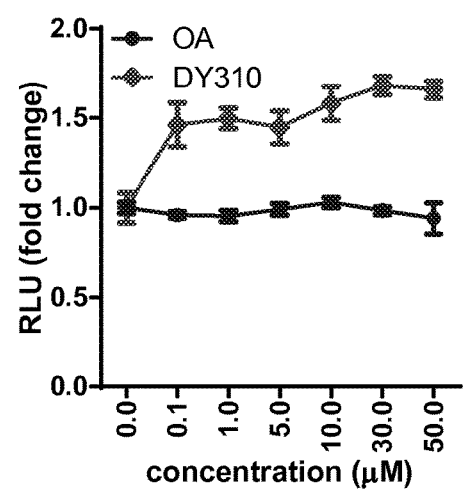
FIG. 7E: DY310 and OA.
Figure 7F:
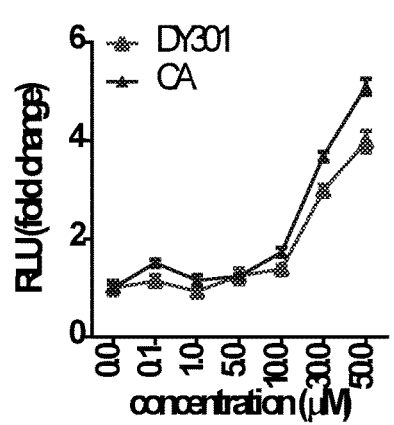

The metformin-based TGR5 natural product agonist complexes were synthesized through the facile and simple synthetic procedures starting from commercially available starting materials as shown by FIG. 5. The transformation of metformin hydrochloride to free base was achieved using 1M NaOH (sodium hydroxide) solution in methanol or ethanol. The complex formation reaction was performed by treatment of the metformin free base with OA, BA, and UA under reflux condition for 12 hrs and resulted in the production of metformin-based OA, BA, and UA complexes.

TABLE 1

A list of metformin-based TGR5 agonist proton transfer complexes.

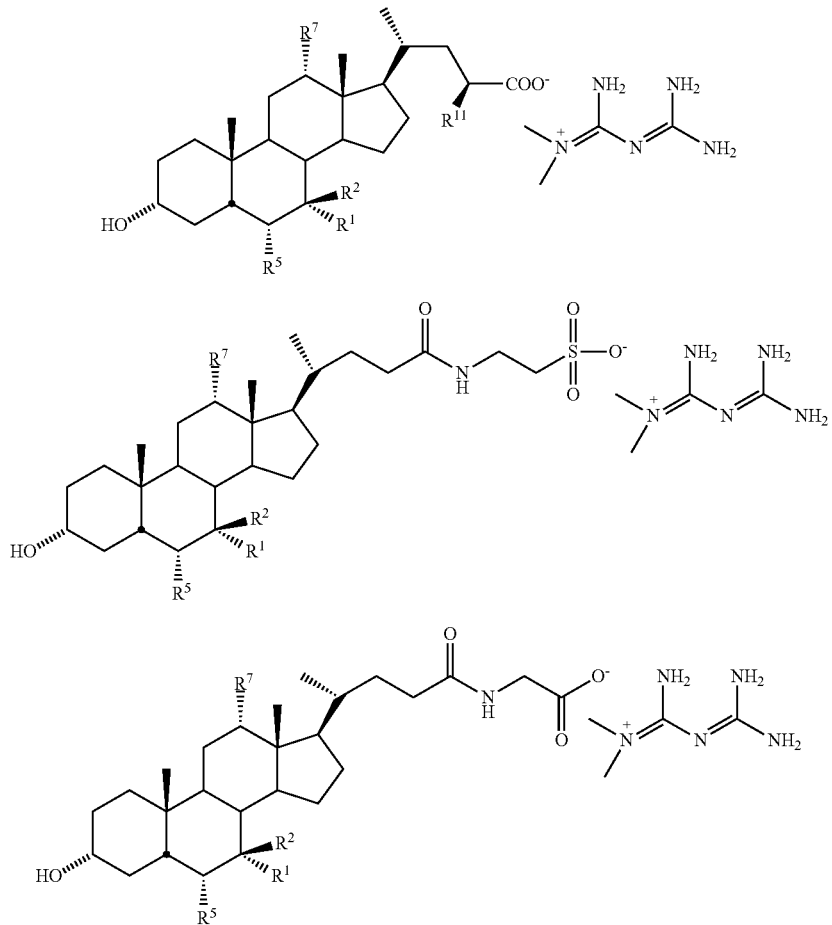

| No. | Metformin-TGR5 ligand complex | $R^1$ | $R^2$ | $R^7$ | $R^5$ | $R^{11}$ |
|---|---|---|---|---|---|---|
| DY301 | metformin-CA complex | OH | H | OH | H | H |
| DY302 | metformin-UDCA complex | H | OH | H | H | H |
| DY303 | metformin-CDCA complex | OH | H | H | H | H |
| DY304 | metformin-tauro-UDCA complex | H | OH | H | H |  |
| DY305 | metformin-6eCDCA complex | OH | H | H | Et | H |
| DY306 | metformin-6eUDCA complex | H | OH | H | Et | H |
| DY307 | metformin-tauro-CA complex | OH | H | OH | H |  |
| DY308 | metformin-LCA complex | H | H | H | H | H |
| DY309 | metformin-23m-LCA complex | H | H | H | H | $CH_3$ |
| DY313 | metformin-6eLCA complex | OH | H | H | Et | $CH_3$ |
| DY314 | metformin-DCA complex | H | H | OH | H | H |
| DY325 | metformin-23m-CDCA complex | OH | H | H | H | $CH_3$ |
| DY326 | metformin-23m-UDCA complex | H | OH | H | H | $CH_3$ |
| DY327 | metformin-tauro-LCA complex | H | H | H | H |  |
| DY328 | metformin-tauro-CDCA complex | OH | H | H | H |  |
| DY329 | metformin-glyco-CA complex | OH | H | OH | H |  |
| DY330 | metformin-tauro-DCA complex | H | H | OH | H |  |
| DY331 | metformin-glyco-CDCA complex | OH | H | H | H |  |
| DY332 | metformin-glyco-UDCA complex | H | OH | H | H |  |

TABLE 1-continued

| DY333 | metformin-glyco-LCA complex | H | H | H | H |
| DY334 | metformin-glyco-DCA complex | H | H | OH | H |

To assess functional activity, we performed a series of luciferase reporter-based assays to evaluate the biological effects of the synthesized metformin-based TGR5 agonist complexes. The complexes were evaluated in cell-based assays for in vitro potency and selectivity, using HEK293 cells stably-expressing human TGR5 and transfected with the cAMP-sensitive reporter plasmid pCRE-Luc. Complexes were evaluated for their ability to activate TGR5 at 0.1, 0.5, 1, 5.0, 10, 30, and 50 µM test concentrations. All of the tested complexes displayed TGR5 specificity and potency relative to their native bile acids and natural TGR5 agonists, represented in FIGS. 7A-7F.

The in vitro data showed that metformin did not directly activate TGR5 to induce cAMP formation in HEK293 cells. Nonetheless, the complexes activated TGR5 receptor. Thus, the combinatorial synthesis of metformin with TGR5 agonists to synthesize the complex resulted in synergistic activity between metformin and the TGR5 agonist. The metformin-based complex DY310 exhibited greater potency in luciferase assays than oleanolic acid against TGR5. LCA, UDCA, 6ECDCA, 6EUDCA, and CA were selected to assess their biological activity against TGR5. Their corresponding complex series, DY301, DY302, DY306, and DY305 displayed same potency compared to native UDCA, 6eUDCA, 6eCDCA, and CA. The most potent and specific metformin-based TGR5 agonist complexes we observed was DY305 and DY306.

A series of metformin/TGR5 ligand complexes (e.g. salts) were prepared. Several complexes were more effective on body weight, fasting glucose, liver weight, kidney weight effects, and HbA1c than metformin alone using db/db mice (See FIGS. 7A-7F, 8, 9, 10, and 11).

The complexes were administered daily for 5 weeks to measure the effect in body weight of male db/db mice. The results are displayed in FIG. 8. There was a dose dependent decrease in body weight gain when administered daily for 5 weeks, and between each dose group and vehicle control, throughout the remainder of the administered daily for 5 weeks experiment. Although the decrease in body weight gain appears to last for administered daily for 5 weeks, the effect on body weight was maintained throughout the dosing period. Complex DY305 is effective in body weight loss. Complexes DY305 and DY306 did exhibited effect in body weight loss but the effect was not significant, perhaps due to an insufficient dose (30 mg/kg BW, 0.057 mmol, metformin-based TGR5 agonist complexes, 250 mg/kg BW metformin, 1.52 mmol).

The dose of the complex DY306 (30 mg, 0.057 mmol) via i.p. injection was 3% of that of metformin (250 mg, 1.52 mmol)—a dose significantly lower than concentrations currently administered. The glucose tolerance test (GTT) in db/db mice was tested after 5 weeks of treatment. See FIG. 9. The overnight-fasted db/db mice were subjected to glucose tolerance test post-2.0 g/kg of body weight of oral glucose load. The fasting baseline blood glucose values at 0 min were found to be lower in all the treated groups compared to the vehicle-treated control group at the corresponding time. The treatment did not significantly inhibit the rise in postprandial blood glucose level of db/db mice after glucose load of 2.0 g/kg of body weight.

Figure 12:
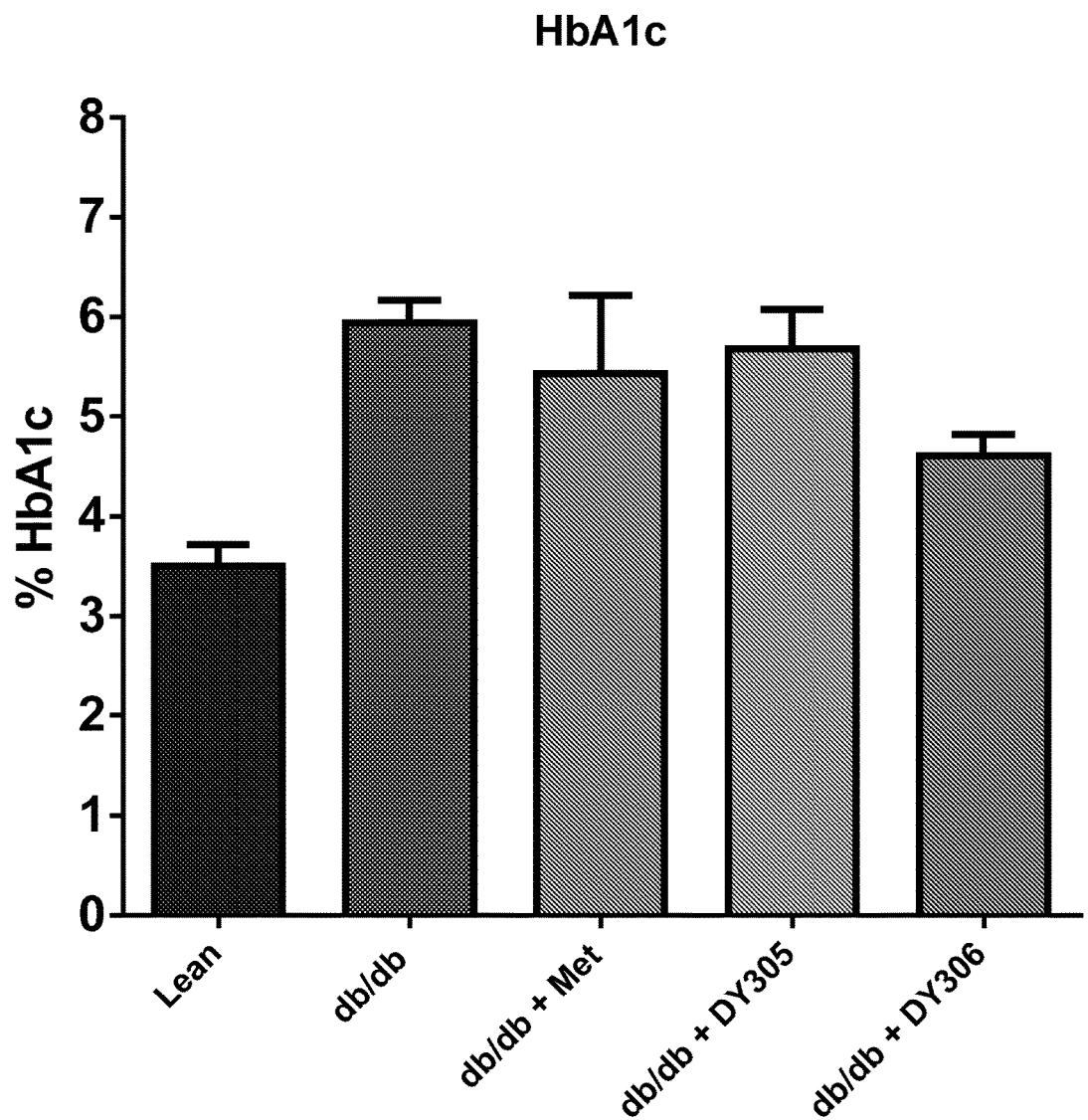
FIG. 12 Histogram depicting effect of metformin-based TGR5 agonist complexes on HbA1c levels (type 2 diabetic male db/db mice model (30 mg/kg BW metformin-based TGR5 agonist complexes, 250 mg/kg BW metformin). The dose of the metformin-based TGR5 agonist complex DY306 (30 mg, 0.057 mmol) via i.p. injection was 3% of that of metformin (250 mg, 1.52 mmol), assumed that the metformin-based complex DY306 would be more efficiently in HbA1c lowering than metformin. (Lean=no metformin or agonist, Non-diabetic mice; db/db=no metformin or agonist, Obese Diabetic mice; db/db DY217=no metformin and 30 mg 6α-ethyl CDCA in db/db mice treatment; db/db DY248=no metformin and 30 mg 6α-ethyl UDCA in db/db mice treat; db/db DY305=30 mg total complex (metformin and DY217(6-ethyl CDCA)) corresponding to 1:1 stoichiometry in db/db mice; db/db DY306=db/db DY306=30 mg total complex (metformin and DY248(6α-ethyl UDCA)) corresponding to 1:1 stoichiometry in db/db mice; Metformin—250 mg metformin in db/db mice treatment). Legend: x-axis (histogram columns left to right): lean, db/db, db/db+metformin (Met), db/db+DY 305, db/db+DY 306; y-axis: % HbA1c.

Glycated hemoglobin (HbA1c) is often used as a marker for glycemic control. Elevated HbA1c is regarded as an independent risk factor for coronary heart disease (CHD) and stroke in subjects with diabetes. We decided to test the potential of metformin/TGR5 agonist complexes to modulate HbA1c levels. The metformin/TGR5 agonist complex DY306 dose dependently blocked the increase of HbA1c in db/db mice (FIG. 12). The treatment with metformin-based TGR5 agonist complex DY306 improved glycemic control in the db/db mouse model. These findings indicate that metformin/TGR5 agonist complexes may be a new class of therapeutic agents for enhancing the efficacy of metformin.

4. EXAMPLE 4

The metformin/TGR5 agonist complexes are stable complexes, with the TGR5 agonist anion, stabilized by strong intramolecular hydrogen bonds with the cations of metformin. The TGR5 agonist may promote the complexation through N—H . . . O hydrogen bonds. That is, the cations of metformin to oxygens of TGR5 agonist thereby possibly creating a dense hydrogen-bonding network. We reasoned that, without being bound by any particular theory, that in the presence of cations of metformin, a TGR5 agonist links through its oxygen atoms to a metformin and exists as a salt. We believe, without being bound by any particular theory, that this salt may undergo an intramolecular complexation and transform into a solid hydrogen-bonded complex as demonstrated by FIG. 13.

The TGR5 derivatives, 6eCDCA and 6eUDCA, are more potent TGR5 than CDCA and UDCA. 6ECDCA is actually in phase II clinical trials for the treatment of cholestasis in subjects with primary biliary cirrhosis and for the management of nonalcoholic steatohepatitis in patients with the metabolic syndrome. We previously developed an improved synthetic pathway to produce 6eCDCA.[27] UDCA is the only drug in the bile acid series that has been approved by FDA for the treatment of primary biliary cirrhosis (PBC), an autoimmune disease characterized by progressive cholestasis. UDCA, in contrast to toxic hydrophobic bile acids, has also been shown to suppress the inflammatory response and as such, is increasingly being employed for the treatment of hepatic and intestinal inflammatory diseases. In addition, treatment with UDCA may improve metabolism by lowering serum levels of primary bile acids. We identified UDCA and 6EUDCA as TGR5 agonists with $EC_{50}$ values of 2.39 and 1.49 VM, respectively. Data analysis to determine $EC_{50}$ values was performed with GraphPad Prism software using a cAMP standard curve and sigmoidal dose-response (variable slope) equation based on dose-response curves with tested compounds. Its conjugates, the Tauro-UDCA and Glyco-UDCA derivatives, were identified as TGR5 agonists.[13]

It is interesting to note that in addition to its use in diabetics, metformin is also effective in the treatment of cancer and is being explored as an antiviral and anticancer agent.[28] Metformin may also kill cancer stem cells. These cancer stem cells make up only a small portion of a cancer, but may be responsible for resistance to chemotherapy or for causing recurrence of the cancer. Further, metformin is being tested in clinical trials not only as a treatment for cancer, but as a way to prevent it in people at increased risk, including cancer survivors who have a higher risk of a second primary cancer.

The dose-ranging, double-blind, placebo-controlled study in patients could examine two dosing regimens: twice daily (DY302 100 mg or less) and once daily (DY302 200 mg or less). For both regimens, the DY302 dose could be lowered if glucose or HbA1c could be reduced.

5. EXAMPLE 5

Chemistry General Procedure: Organic reagents were purchased from commercial suppliers unless otherwise noted and were used without further purification. All solvents were analytical or reagent grade. All reactions were carried out in flame-dried glassware under argon or nitrogen. Melting points were determined and reported automatically by an optoelectronic sensor in open capillary tubes and were uncorrected. $^1$H NMR and $^{13}$C NMR spectra were measured at 500 MHz and 125 MHz respectively, using CDCl$_3$ or DMSO-d$_6$ as the solvents and tetramethylsilane (Me$_4$Si) as the internal standard. Flash column chromatography was performed using Sigma-Aldrich silica gel 60 (200-400 mesh), carried out under moderate pressure by using columns of an appropriate size packed and eluted with appropriate eluents. Silica gel chromatography was performed on a BIOTAGE® flash column gradient pump system using 15 cm long columns. All reactions were monitored by TLC on precoated plates (silica gel HLF). TLC spots were visualized either by exposure to iodine vapors or by irradiation with UV light. Organic solvents were removed in vacuum by rotary evaporator. Elemental analyses were performed by Columbia Analytical Services Inc., Tucson, Ariz.

General procedure for the preparation of metformin-based TGR5 bile acid agonist complexes: Metformin hydrochloride (0.5 g, 3.01 mmol) was added to a solution of 5 mL of iso-PrOH and the reaction mixture was stirred at RT for 30 min. Potassium hydroxide (0.18 g, 3.21 mmol) was added to the stirred solution, at 50° C. for 1 h, and then the reaction mixture was cooled to room temperature. The solid part (NaCl) was filtered off and the filter-cake was washed with ethanol and EtOAc. The combined filtrates were concentrated under reduced pressure affording a white solid as a metformin free base. To a solution of metformin free base (0.38 g, 3.01 mmol) in 25 mL of methanol, the appropriate bile acids or their derivatives (1 equiv) was added. The resulting mixture was stirred for overnight. The solvent was evaporated under reduced pressure, and the residue was dissolved in chloroform. The chloroform solution was evaporated under reduced pressure to dryness and solidified by EtOAc. The precipitate was collected by filtration and washed with Hexanes to afford metformin-complex as white solids.

General procedure for the preparation of metformin-based TGR5 agonist complexes with tauro-form or glycol-form: To a solution of sodium tauro or sodium glycol bile cholate (3.03 mmol) in 25 mL of methanol, metformin hydrochloride (0.5 g, 3.03 mmol) was added and the reaction mixture was stirred at room temperature overnight. After removing the solvent under reduced pressure, 10% MeOH in isopropanol (20 mL) was added to the reaction mixture. The solid part (NaCl) was filtered off. The solvent was evaporated under reduced pressure, and the residue was dissolved in chloroform. The chloroform solution was evaporated under reduced pressure to dryness and solidified by EtOAc. The precipitate was collected by filtration and washed with hexanes to afford metformin-complex as white solids.

Examples of complex preparations: Metformin-CA complex (compound DY301). Metformin hydrochloride (0.5 g, 3.01 mmol) was added to 2 mL of 1 M NaOH and the reaction mixture was stirred at RT for 30 min. Water was evaporated in vacuo, and the residue was dissolved in 5 mL of methanol. The solvent was evaporated, and the residue was redissolved in 5 mL of methanol and NaCl was filtered. The filtered solution was evaporated to yield a metformin free base as a white solid (0.38 g, 99%). To a solution of metformin free base (0.38 g, 3.01 mmol) in methanol (10 mL) was added cholic acid (CA) (1.22 g, 3.01 mmol), and the reaction mixture was heated to 50° C. and stirred at 50° C. overnight. The solvent was removed and the residue was solidified by EtOAc to provide white solids 1.31 g (81% yield), mp. 187.9° C. $^1$H NMR (DMSO-d$_6$): (selected data), δ 7.19 (broad, NH), 3.77 (s, 1H), 3.59, (s, 1H), 3.14 (m, 1H), 2.91 (s, 6H), 2.15 (m, 2H), 0.89 (d, 3H), 0.79 (s, 3H), 0.56 (s, 3H). $^{13}$C NMR (DMSO-d$_6$) δ 180.7, 161.8, 73.8, 73.2, 69.0, 49.2, 44.3, 42.0, 38.3, 38.1, 37.7, 35.0, 33.2, 31.3, 30.2, 29.0, 25.7, 25.4, 20.0, 15.5. Anal. Calcd for $C_{28}H_{51}N_5O_5 \cdot 3H_2O$: C, 56.88; H, 8.69; N, 11.84. Found: C, 56.66; H, 8.61; N, 11.65. Both $^1$H NMR and elemental analysis correspond to a 1:1 stoichiometry.

Metformin-UDCA complex, (compound DY302). Metformin hydrochloride (0.1 g, 0.6 mmol) was added to 2 mL of 1 M NaOH and the reaction mixture was stirred at RT for 30 min. Water was evaporated in vacuo, and the residue was dissolved in 5 mL of methanol. The solvent was evaporated, and the residue was redissolved in 5 mL of methanol and NaCl was filtered. The filtered solution was evaporated to yield a metformin free base as a white solid (0.07 g, 99%). To a solution of metformin in DMF (2 mL), UDCA (0.23 g, 0.6 mmol) was added. The reaction mixture was stirred overnight. The solvent was removed and the residue was solidified by EtOAc to provide white solids 0.12 g (40% yield), mp. 198.8° C. $^1$H NMR (DMSO-d$_6$): (selected data), δ 7.01 (br, NH), 3.31 (s, 6H), 1.94 (m, 2H), 1.82 (m, 2H), 1.05 (s, 3H), 0.99 (d, 3H), 0.61 (s, 3H). $^{13}$C NMR (CDCl$_3$) δ 181.2, 163.1, 162.3, 72.9, 72.7, 59.2, 58.5, 46.2, 45.5, 43.2, 43.1, 41.0, 40.7, 38.7, 38.5, 38.2, 37.1, 36.0, 33.6, 31.6, 30.1, 26.6, 24.2, 21.9, 15.4. Anal. Calcd for $C_{28}H_{51}N_5O_4 \cdot 4H_2O$: C, 56.63; H, 8.66; N, 10.11. Found: C, 56.69; H, 8.88; N, 10.00. Both $^1$H NMR and elemental analysis correspond to a 1:1 stoichiometry.

Metformin-6ECDCA complex, (compound DY305). Metformin hydrochloride (0.5 g, 3.01 mmol) was added to 5 mL of 1 M NaOH and the reaction mixture was stirred at RT for 30 min. Water was evaporated in vacuo, and the residue was dissolved in 10 mL of methanol. The solvent was evaporated, and the residue was redissolved in 10 mL of methanol and NaCl was filtered. The filtered solution was evaporated to yield a metformin free base as a white solid (0.37 g, 97%). To a stirred suspension of metformin free base (0.37 g, 2.86 mmol) in iso-PrOH (5 mL) was added 6α-ethyl-chenodeoxycholic acid (6ECDCA) (0.9 g, 2.13 mmol) and the reaction mixture was heated to 50° C. and stirred overnight. The solvent was removed and the residue was solidified by EtOAc to provide white solids 0.78 g (71%, yield), mp. 167.8° C. $^1$H NMR (D$_2$O): (selected data), δ 8.31 (s, 2H), 3.67 (s, 1H), 3.33 (s, 1H), 2.91 (s, 6H), 2.09 (s, 2H), 0.99 (m, 2H), 0.82 (d, 3H), 0.77 (t, 6H), 0.54 (s, 3H). $^{13}$C NMR (D$_2$O) δ 177.0, 163.1, 162.3, 74.7, 73.4, 57.9, 52.9, 47.9, 44.3, 42.7, 42.2, 38.5, 37.1, 35.9, 35.2, 32.4, 30.8, 26.2, 26.0, 24.8, 23.7, 20.9, 14.5, 14.2. Anal. Calcd for $C_{30}H_{55}N_5O_4 \cdot 3H_2O$: C, 59.47; H, 9.48; N, 11.56. Found: C, 59.48; H, 9.11, N, 11.53. Both $^1$H NMR and elemental analysis correspond to a 1:1 stoichiometry.

Metformin-6EUDCA complex, (compound DY306). Metformin hydrochloride (0.05 g, 0.3 mmol) was added to 5 mL of 1 M NaOH and the reaction mixture was stirred at RT for 30 min. Water was evaporated in vacuo, and the residue was dissolved in 5 mL of methanol. The solvent was evaporated, and the residue was redissolved in 5 mL of methanol and NaCl was filtered. The filtered solution was evaporated to yield a metformin free base as a white solid (0.049 g, 98%). To a solution of metformin in DMF (2 mL), 6EUDCA (0.12 g, 0.3 mmol) was added. The reaction mixture was stirred overnight. The solvent was removed and the residue was solidified by EtOAc to provide white solids 0.076 g (48% of yield), mp: 255.9° C. $^1$H NMR (DMSO-d$_6$): (selected data), δ 8.37 (broad, NH), 3.67 (s, 1H), 3.79 (s, 1H), 3.50 (s, 1H), 2.99 (s, 6H), 2.12 (m, 2H), 0.99 (m, 2H), 0.89 (m, 6H), 0.82 (d, 3H), 0.58 (s, 3H). $^{13}$C NMR (DMSO-d$_6$): δ 173.9, 160.3, 160.3, 74.7, 73.4, 58.5, 55.3, 48.1, 44.3, 42.7, 42.2, 40.4, 40.2, 38.3, 37.1, 35.2, 32.4, 30.8, 30.7, 28.3, 27.3, 23.7, 20.9, 14.5, 14.3. Anal. Calcd for $C_{30}H_{57}N_5O_4 \cdot 10H_2O$: C, 49.35; H, 7.59; N, 9.59. Found: C, 49.11; H, 7.45, N, 9.10. Both $^1$H NMR and elemental analysis correspond to a 1:1 stoichiometry.

Metformin-tauroUDCA Complex, (Compound DY304). To a solution of sodium tauroursodeoxycholate (0.5 g, 0.95 mmol) in 25 mL of methanol, metformin hydrochloride (0.16 g, 0.95 mmol) was added and the reaction mixture was stirred at RT for overnight. After removing the solvent under reduced pressure, 10% MeOH in iso-propanol (20 mL) was added to the reaction mixture. The solid part (NaCl) was filtered off. The solvent was evaporated under reduced pressure, and the residue was dissolved in chloroform. The chloroform solution was evaporated under reduced pressure to dryness and solidified by EtOAc. The precipitate was collected by filtration and washed with Hexanes to afford metformin-complex as white solids 0.42 g (72% yield), mp. 173.8° C. $^1$H NMR (CDCl$_3$/CD$_3$OD): (selected data), δ 7.89 (broad, 2H), 7.19 (d, 2H), 6.47 (s, broad, 2H), 3.61 (s, 2H), 3.51 (s, broad, 2H), 3.07 (s, 6H), 2.98 (s, 2H), 2.25 (m, 1H), 2.11 (m, 2H), 0.99 (d, 3H), 0.74 (s, 3H). $^{13}$C NMR (CDCl$_3$/CD$_3$OD): δ 178.3, 73.6, 73.4, 58.9, 57.9, 52.9, 45.9, 45.5, 43.0, 42.2, 40.1, 39.5, 38.3, 37.6, 35.7, 34.7, 32.5, 31.1, 29.4, 25.4, 23.9, 20.5, 14.7. Anal. Calcd for $C_{30}H_{56}N_6O_6S$: C, 57.30; H, 8.98; N, 13.36. Found: C, 56.99; H, 8.45, N, 12.97. Both $^1$H NMR and elemental analysis correspond to a 1:1 stoichiometry.

Metformin-tauroCA complex, (compound DY307). To a solution of sodium taurocholate hydrate (1.63 g, 3.03 mmol) in 25 mL of methanol, metformin hydrochloride (0.5 g, 3.03 mmol) was added and the reaction mixture was stirred at RT for overnight. After removing the solvent under reduced pressure, 10% MeOH in iso-propanol (20 mL) was added to the reaction mixture. The solid part (NaCl) was filtered off. The solvent was evaporated under reduced pressure, and the residue was dissolved in chloroform. The chloroform solution was evaporated under reduced pressure to dryness and solidified by EtOAc. The precipitate was collected by filtration and washed with Hexanes to afford metformin-complex as white solids 1.4 g (72% of yield), mp: 120.5° C. $^1$H NMR (CDCl$_3$/CD$_3$OD): (selected data), δ 7.61 (broad, 1H), 7.40 (d, 2H), 6.93 (s, 1H), 6.44 (s, broad, 2H), 4.04 (s, 1H), 3.90 (s, 1H), 3.70 (t, 2H), 3.49 (s, 1H), 3.32 (t, 2H), 3.14 (s, 3H), 3.13 (s, 1H), 3.02 (s, 3H), 2.32 (m, 1H), 1.07 (s, 3H), 0.97 (d, 3H), 0.76 (s, 3H). $^{13}$C NMR (CDCl$_3$/CD$_3$OD): δ 178.0, 162.1, 75.8.3, 74.4, 71.1, 53.0, 49.1, 48.7, 44.5, 42.3, 42.1, 38.3, 37.5, 35.2, 34.2, 32.8, 30.8, 30.4, 29.3, 25.9, 25.2, 20.0, 15.2. Anal. Calcd for $C_{30}H_{56}N_6O_7S \cdot 2H_2O$: C, 52.95; H, 8.39; N, 12.35. Found: C, 52.81; H, 9.00, N, 12.49. Both $^1$H NMR and elemental analysis correspond to a 1:1 stoichiometry.

Metformin-OA (compound DY310). Metformin hydrochloride (0.1 g, 0.6 mmol) was added to a solution of 2 mL of 1 M NaOH and the reaction mixture was stirred at RT for 30 min. Water was evaporated in vacuo, and the residue was dissolved in 5 mL of methanol. The solvent was evaporated, and the residue was redissolved in 5 mL of methanol and NaCl was filtered. The filtered solution was evaporated to yield free amine of basic metformin as a white solid (0.07 g 98%). To a solution of metformin in n-butanol (10 mL), oleanolic acid (OA) (0.27 g, 0.6 mmol) was added. The reaction mixture was warmed up to 70° C. and stirred overnight. The solvent was removed and the residue was solidified by Hexanes/EtOAc to provide white solids (0.27 g, 77%), mp: 254.7° C. $^1$H NMR (DMSO-d$_6$): (selected data), δ 7.92 (s, 2H), 7.17 (bs, 4H), 5.11 (s, 1H), 4.27 (s, 1H), 3.00 (s, 1H), 2.92 (s, 6H), 1.89 (m, 2H), 1.66 (m, 2H), 1.48 (s, 3H), 1.07 (s, 3H), 0.89 (t, 12H), 0.71 (s, 3H), 0.66 (s, 3H). $^{13}$C NMR (DMSO-d$_6$): δ 182.6, 163.3, 161.0, 147.5, 123.7, 79.6, 57.6, 49.7, 48.9, 43.7, 40.9, 36.4, 35.8, 35.3, 31.0, 30.1, 29.8, 28.4, 26.3, 25.7, 20.8, 18.8. Anal. Calcd for $C_{34}H_{59}N_5O_3$: C, 69.70; H, 10.15, N, 11.95. Found: C, 69.46; H, 9.87, N, 11.84. Both $^1$H NMR and elemental analysis correspond to a 1:1 stoichiometry.

6. EXAMPLE 6

Biology

Cell Culture: HEK293 and HEK293-TGR5 overexpressing cells were cultured in high glucose Dulbecco's modified Eagle's medium (DMEM, CELLGRO®, Manassas, Va.) with L-glutamine supplemented with 10% (vol/vol) heat-inactivated fetal bovine serum (Gemini Bio-Products, West Sacramento, Calif.). TGR5-overexpressing HEK293 cells were maintained in G418-containing media until plating. Cells were plated in 24-well plates ($5 \times 10^5$ cells/well) 24 h before transfection. Prior to transfection, cells were rinsed with PBS, and media was replaced with DMEM without phenol red supplemented with 10% super-stripped FBS.

TGR5 and FXR Luciferase Assay: To evaluate TGR5 activity of compounds, cells were transfected 100 ng pCRE-luc reporter along with pCMV-galactosidase (10 ng) as an internal control for normalization of transfection efficiency. Plasmids were complexed with 2 mL of FUGENE® 6 reagent (Promega, Madison, Wis.) in OPTIMEM® (Invitrogen, Carlsbad, Calif.) and cells were transfected for 18 h. The following day, cells were treated with vehicle and appropriate ligand as indicated. Luciferase and β-galactosidase activities were assayed 6 h later using Luciferase Assay System (Promega) and GALACTO-STAR™ (Applied Biosystems, Foster City, Calif.) reagents, respectively, and a MLX® luminometer (Dynex Technologies, Chantilly, Va.).

To evaluate the FXR activity of compounds, HEK293 cells were transfected with 25 ng of farnesoid X receptor expression plasmid (pCMX-hFXR), 25 ng of retinoid X receptor expression plasmid (pCMXhRXR), 100 ng of reporter plasmid (pEcREx6-TK-Luc), and 10 ng of pCMV-β-galactosidase as an internal control in each well, using FUGENE® 6 reagent. Approximately 18 h after transfection, cells were incubated for 12 h with different concentrations of each compound in DMEM without phenol red supplemented with 10% super-stripped FBS. Cells were lysed and normalized and luciferase activity was determined.

cAMP Assays: HEK293 overexpressing TGR5 were treated with vehicle and appropriate ligand for 30 min in induction buffer comprised of serum-free Krebs Ringer buffer supplemented with 100 mM Ro 20-1274 and 500 mM IBMX (Sigma, St. Louis, Mo.) and cAMP levels were determined in lysates using CAMP-GLO™ Assay Kit (Promega) according to the manufacturer's protocol. Data analysis to determine $EC_{50}$ values was performed with GraphPad Prism software using a cAMP standard curve and sigmoidal dose-response (variable slope) equation based on dose-response curves with tested compounds.

Animal Model: This project aimed to test the effects novel metformin-based TGR5 agonist complexes (or salts) and developed here at City of Hope, in modulating glucose and lipid metabolism and preventing weight loss and other metabolic alterations in diabetic db/db mice models. Experiments were conducted where the compounds and metformin and their complexes were tested in db/db mice separately. For each experiment, there were 8 groups of mice representing the different treatments. For all animal studies, the desired concentration of metformin-based TGR5 agonist complexes were dissolved in vehicle consisting of 20% PEG400, 58% Tween 80, 78% water (this method was successfully used in previous experiments without toxicity). Eleven-week old male normal and high-fat fed C57BL/6J mice and 7-week old male B6.BKS-Lepr$^{db}$ (db/db) mice (The Jackson Laboratory, Bar Harbor, Me.) were acclimatized for at least one week on a 12-hour light/dark cycle at 68-72° F., then fed either a standard (10% fat kcal) or high-fat diet containing 60 kcal % fat (Research Diets, Inc., New Brunswick, N.J.) for the duration of the study. All animals were access to their respective diets and water ad libitum. Mice were divided into untreated control, and metformin-based TGR5 agonist complexes or metformin treated groups and their individual TGR5 agonists. For each group, each mouse was given the drugs via i.p. injection, three times a week (Monday, Wednesday, Friday) for a total duration of 5 weeks. Before, and in the course of treatment, body weight, water and food consumption (by weighing before and after weights of water bottles and leftover food in individual cages) were measured 2×per week, while blood glucose measurements were conducted weekly via tail-bleeding while on physical restraint using disposable cone-shaped plastic holders (Kent Scientific). Various tissues (liver, skeletal muscles and adipose tissues) and blood (for lipid, insulin and glucose measurements), were collected and analyzed at the end of the experiment. Before termination of the study, glucose tolerance tests were performed on each mouse on the last week of treatment. For the glucose tolerance test (GTT), after an overnight fast, mice were injected intraperitoneally with glucose (2 g/kg body weight). Blood was sampled from the tail vein before and 15, 30, 60, 90, and 120 min after the injection, and plasma glucose concentrations were determined by a glucometer. Mice were euthanized by $CO_2$ asphyxiation according to the Association for Assessment and Accreditation of Laboratory Animal Care International guidelines. The different experimental groups had at least 8 animals each.

REFERENCES

1. Cowie, C. C., Eberhardt, M. S. *Diabetes* 1996 *Vital Statistics*; American Diabetes Association: Alexandria, Va.

2. Wild, S.; Roglic, G.; Green, A.; Sicree, R.; King, H. Global prevalence of diabetes: estimates for the year 2000 and projections for 2030. *Diabetes Care* 2004, 27, 1047-53.

3. Forman, B. M.; Goode, E.; Chen, J.; Oro, A. E.; Bradley, D. J.; Perlmann, T.; Noonan, D. J.; Burka, L. T.; McMorris, T.; Lamph, W. W.; Evans, R. M.; Weinberger, C. *Cell*. Identification of a nuclear receptor that is activated by farnesol metabolites. 1995, 81, 687-693.

4. Maruyama, T.; Miyamoto, Y.; Nakamura, T.; Tamai, Y.; Okada, H.; Sugiyama, E.; Nakamura, T.; Itadani, H.; Tanaka, K. Identification of membrane-type receptor for bile acids (M-BAR). *Biochem. Biophys. Res. Commun.* 2002, 298, 714-719.

5. Lefebvre, P.; Cariou, B.; Lien, F.; Kuipers, F.; Staels, B. Role of bile acids and bile acid receptors in metabolic regulation. *Physiol. Rev.* 2009, 89, 147-191.

6. Wang, H.; Chen, J.; Hollister, K.; Sower, L. C.; Forman, B. M. Endogenous bile acids are ligands for the nuclear receptor FXR/BAR. *Mol. Cell* 1999, 3, 543-553.

7. Katsuma, S.; Hirasawa, A.; Tsujimoto, G. Bile Acids Promote Glucagon-like Peptide-1 Secretion Through TGR5 in a Murine Enteroendocrine Cell. *Biochem Biophys Res Commun.* 2005, 329, 386-90.

8. Keitel, V.; Donner, M.; Winandy, S.; Kubitz, R.; Häussinger, D. Expression and function of the bile acid receptor TGR5 in Kupffer cells. *Biochem. Biophys. Res. Commun.* 2008, 372, 78-84.

9. Tiwari, A.; Maiti, P. TGR5: An Emerging Bile Acid G-protein Coupled Receptor Target for the Potential Treatment of Metabolic Disorders. *Drug Discovery Today* 2009, 14, 523-530.

10. Thomas, C.; Pellicciari, R.; Pruzanski, M.; Auwerx, J.; Schoonjans, K. Targeting bile-acid signalling for metabolic diseases, *Nature Reviews Drug Discovery* 7, 2008, 678-693.

11. American Diabetes Association. Standards of Medical Care in Diabetes 2007. *Diabetes Care* 2007, 30, S4-S41.

12. Thomas, C.; Gioiello, A.; Noriega, L.; Strehle, A.; Oury, J.; Rizzo, G.; Macchiarulo, A.; Yamamoto, H.; Mataki, C.; Pruzanski, M.; Pellicciari, R.; Auwerx, J.; Schoonjans, K. TGR5-mediated bile acid sensing controls glucose homeostasis. *Cell Metab.* 2009, 10, 167-177.

13. Sato, H.; Macchiarulo, A.; Thomas, C.; Gioiello, A.; Une, M.; Hofmann, A. F.; Saladin, R.; Schoonjans, K.; Pellicciari, R.; Auwerx, J. Novel potent and selective bile acid derivatives as TGR5 agonists: biological screening, structure-activity relationships, and molecular modeling studies. *J. Med. Chem.* 2008, 51, 1831-41.

14. Davidson, M. B.; Peters, A. L. An Overview of Metformin in the Treatment of Type 2 Diabetes Mellitus. *Am. J. Med.* 1997, 102, 99-110.

15. Kappe, C.; Patrone, C.; Holst, J. J.; Zhang, Q.; Sjoholm, A. Metformin protects against lipoapoptosis and enhances GLP-1 secretion from GLP-1-producing cells, *J Gastroenterol.* 2013, 48, 322-332.

16. Stratton, I. M.; Adler, A. I.; Neil, H. A. W.; Matthews, D. R.; Manley, S. E.; Cull, C. A.; Hadden, D.; Turner, R. C.; Holman, R. R. Association of Glycaemia with Macrovascular and Microvascular Complications of Type 2 Diabetes (UKPDS 35): Prospective Observational Study. *Br. Med. J.* 2000, 321, 405-412.

17. Tucker, G. T.; Casey, C.; Phillips, P. J.; Connor, H.; Ward, J. D.; Woods, H. F. Metformin Kinetics in Healthy Subjects and in Patients with Diabetes Mellitus. *Br. J. Clin. Pharmacol.* 1981, 12, 235-246.

18. Wahdan-Alaswad, R.; Fan, Z.; Edgerton, S. M.; Liu, B.; Deng, X-S.; Amadottir, S. S.; Richer, J. K.; Anderson, S. M. Thor, A. D. Glucose promotes breast cancer aggression and reduces metformin efficacy. *Cell Cycle.* 2013, 24, 3759-3769.

19. Dandona, P.; Fonseca, V.; Mier, A.; Beckett, A. G. Diarrhea and Metformin in a Diabetic Clinic. *Diabetes Care* 1983, 6, 472-474.

20. Gordon, G. S.; Moses, A. C.; Silver, R. D.; Flier, J. S.; Carey, M. C. Nasal absorption of insulin: enhancement by hydrophobic bile salts. *Proc. Natl. Acad. Sci. USA* 1985, 82, 7419-7423.

21. Bonhomme, Y. Briet, Ph. PCT Int. Appl. 1999, WO9940, 904.

22. Belcher, G.; Lambert, C.; Edwards, G.; Urquhart, R.; Matthews, D. R. Safety and Tolerability of Pioglitazone, Metformin, and Gliclazide in the Treatment of Type 2 Diabetes. *Diabetes Res. Clin. Pract.* 2005, 70, 53-62.

23. Porez, G; Prawitt, J; Gross, B; Staels, B. Bile acid receptors as targets for the treatment of dyslipidemia and cardiovascular disease. *J Lipid Res.* 2012, 53, 1723-37.

24. L. C. Y. Woo, V. G. Yuen, K. H. Thompson, J. H. Mcneill, C. Orvig, Vanadyl-biguanide complexes as potential synergistic insulin mimics. *J. Inorg. Biochem.* 1999, 76, 251-7.

25. Proctor, W. R.; Bourdet, D. L.; Thakker, D. R. Mechanism Underlying Saturable Intestinal Absorption of Metformin. Drug Metab. Dispos. 2008, 36, 1650-1658.

26. Genet, C.; Sterile, A.; Schmidt, C.; Boudjelal, G.; Lobstein, A.; Schoonjans, K.; Souchet, M.; Auwerx, J.; Saladin, R.; Wagner, A. Structure-Activity Relationship Study of Betulinic Acid. A Novel and Selective TGR5 Agonist, and Its Synthetic Derivatives: Potential Impact in Diabetes. *J. Med. Chem.* 2010, 53, 178-190.

27. Donna Yu, Daniell L. Mattern, Barry M. Forman. An improved synthesis of 6a-ethylchenodeoxycholic acid (6ECDCA), a potent and selective agonist for the Farnesoid X Receptor (FXR). *Steroids.* 2012, 77, 1335-1338.

28. Ben Sahra I, Le Marchand-Brustel Y, Tanti J F, Bost F: Metformin in cancer therapy: a new perspective for an old anti-diabetic drug? *Mol Cancer Ther* 2010, 9, 1092-1099.

29. Ganie M A, Khurana M L, Nisar S, Shah P A, Shah Z A, Kulshrestha B, Gupta N, Zargar M A, Wani T A, Mudasir S, Mir F A, Taing S: Improved efficacy of low-dose spironolactone and metformin combination than either drug alone in the management of women with polycystic ovary syndrome (PCOS): a six-month, open-label randomized study. *J. clin. Endocrinol. Metat.* 2013, 98(9), 3599-3607.

Embodiments

Embodiment 1. A complex comprising a metformin or metformin analogue non-covalently bound to a TGR5 ligand.

Embodiment 2. A complex between a metformin or metformin analogue and a TGR5 ligand, wherein said TGR5 ligand is non-covalently bound to said metformin or metformin analogue.

Embodiment 3. The complex of embodiment 1 or 2, wherein said non-covalent bond is an ionic bond.

Embodiment 4. The complex of any one of embodiments 1 to 3, wherein said metformin or metformin analogue and said TGR5 ligand form a salt complex.

Embodiment 5. The complex of embodiment 1 or 2, wherein said non-covalent bond is a hydrogen bond.

Embodiment 6. The complex of any one of embodiments 1 to 5, wherein said TGR5 ligand is a natural product TGR5 agonist or a synthetic TGR5 agonist derivative.

Embodiment 7. The complex of embodiment 6, wherein, said natural product TGR5 agonist is a natural triterpenoid TGR5 agonist; and said TGR5 synthetic agonist derivative is a synthetic TGR5 triterpenoid agonist derivative.

Embodiment 8. The complex of embodiment 7, wherein said natural TGR5 triterpenoid agonist is oleanolic acid, betulinic acid, or ursolic acid.

Embodiment 9. The complex of embodiment 7, wherein said synthetic TGR5 triterpenoid agonist derivative has the formula:

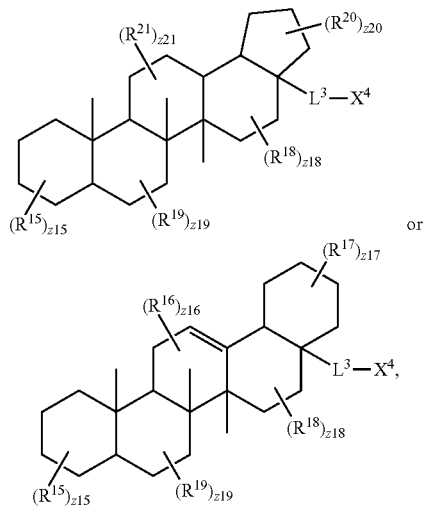

or wherein, $L^3$ is a bond, substituted or unsubstituted alkylene, or substituted or unsubstituted heteroalkylene; $X^4$ is —C(O)NH-$L^4$-$R^{22}$, —C(O)O-$L^4$-$R^{22}$, —C(O)-$L^4$-$R^{22}$, —S(O)$_{n2}$-$L^4$-$R^{22}$, —S(OR$^{13}$)(OR$^{14}$)O-$L^4$-$R^{22}$, or an acid moiety; n2 is 1, 2, or 3; $L^4$ is independently a bond, substituted or unsubstituted alkylene, substituted or unsubstituted heteroalkylene; $R^{15}$, $R^{16}$, $R^{17}$, $R^{18}$, $R^{19}$, $R^{20}$, and $R^{21}$ are independently hydrogen, halogen, —N$_3$, —CF$_3$, —CCl$_3$, —CBr$_3$, —CI$_3$, —CN, —CHO, —OR$^{13}$, —NR$^{13}$R$^{14}$, —CONR$^{13}$R$^{14}$, —NO$_2$, —SR$^{13}$, —SO$_{n3}$R$^{13}$, —SO$_{n3}$OR$^{13}$, —SO$_{n3}$NR$^{13}$R$^{14}$, —NHNR$^{13}$R$^{14}$, —ONR$^{13}$R$^{14}$, —NHC(O)NHNR$^{13}$R$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n3 is 1 or 2; z15 and z17 are independently 1, 2, 3, 4, 5, 6, 7, 8 or 9; z16, z18, and z19 are independently 1, 2, 3, 4, 5, or 6; z20 is 1, 2, 3, 4, 5, 6, or 7; z21 is 1, 2, 3, or 4; and $R^{22}$ is an acid moiety.

Embodiment 10. The complex of embodiment 9, wherein said synthetic TGR5 triterpenoid agonist derivative has the formula:

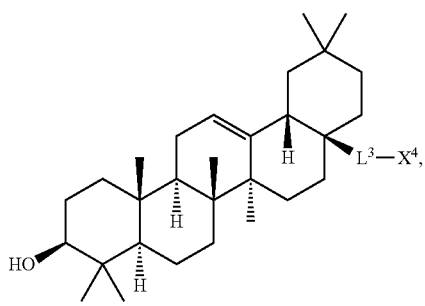

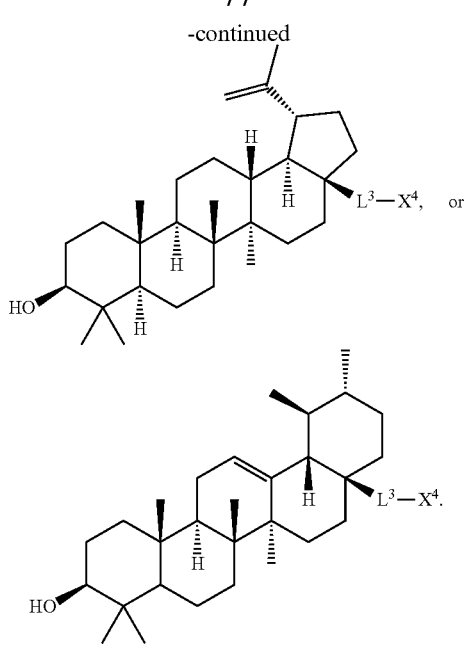

Embodiment 11. The complex of embodiment 9 or 10, wherein $X^4$ is an acid moiety.

Embodiment 12. The complex of any one of embodiments 9 to 11, wherein said acid moiety is —COOH or —SO$_3$H.

Embodiment 13. The complex of any one of embodiments 1 to 5, wherein said TGR5 ligand is a natural product bile acid or a synthetic bile acid derivative.

Embodiment 14. The complex of embodiment 13, wherein said natural product bile acid is cholic acid (CA), lithocholic acid (LCA), chenodeoxycholic acid (CDCA), ursodeoxycholic acid (UDCA), deoxycholic acid (DCA), or a natural analogue thereof.

Embodiment 15. The complex of embodiment 13 or 14, wherein said TGR5 ligand is a synthetic_bile acid derivative having the formula:

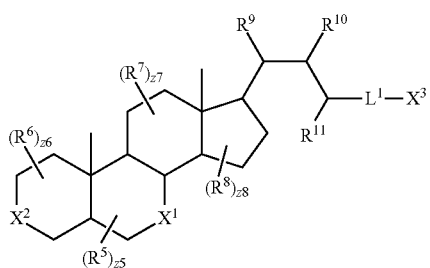

wherein, $L^1$ is a bond, substituted or unsubstituted alkylene, or substituted or unsubstituted heteroalkylene; $X^1$ is C(O) or C(R$^1$)(R$^2$); $X^2$ is C(O) or C(R$^3$)(R$^4$); $X^3$ is —C(O)NH-L$^2$-R$^{12}$, —C(O)O-L$^2$-R$^{12}$, —C(O)-L$^2$-R$^{12}$, —S(O)$_{n1}$-L$^2$-R$^{12}$, —S(OR$^{13}$)(OR$^{14}$)O-L$^2$-R$^{12}$, or an acid moiety; n1 is 1, 2, or 3; $L^2$ is independently a bond, substituted or unsubstituted alkylene, substituted or unsubstituted heteroalkylene; R$^1$, R$^2$, R$^3$, R$^4$ and R$^{11}$ are independently hydrogen or unsubstituted alkyl; R$^5$, R$^6$, R$^7$, R$^8$, R$^9$, and R$^{10}$ are independently hydrogen, halogen, —N$_3$, —CF$_3$, —CCl$_3$, —CBr$_3$, —CI$_3$, —CN, —CHO, —OR$^{13}$, —NR$^{13}$R$^{14}$, —CONR$^{13}$R$^{14}$, —NO$_2$, —SR$^{13}$, —SO$_{n3}$R$^{13}$, —SO$_{n3}$OR$^{13}$, —SO$_{n3}$NR$^{13}$R$^{14}$, —NHNR$^{13}$R$^{14}$, —ONR$^{13}$R$^{14}$, —NHC(O)NHNR$^{13}$R$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n3 is 1 or 2; z5 is 1, 2, 3, 4, 5, or 6; z6 and z8 are independently 1, 2, 3, 4, 5, 6, 7, or 8; z7 is 1, 2, 3, 4, 5, 6, or 7; R$^{12}$ is an acid moiety; and R$^{13}$ and R$^{14}$ are independently are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 16. The complex of embodiment 15, wherein R$^6$, R$^8$, and R$^{10}$ are independently hydrogen.

Embodiment 17. The complex of embodiment 15 or 16, wherein R$^{11}$ is unsubstituted alkyl.

Embodiment 18. The complex of any one of embodiments 15 to 17, wherein R$^{11}$ is attached to a chiral carbon having (S) stereochemistry.

Embodiment 19. The complex of any one of embodiments 15 to 18, wherein R$^5$ is unsubstituted alkyl and z5 is 1.

Embodiment 20. The complex of any one of embodiments 15 to 19, wherein R$^5$ is attached to a chiral carbon having an α-stereochemistry on the 6-position.

Embodiment 21. The complex of any one of embodiments 15 to 20, wherein said synthetic_bile acid derivative has formula:

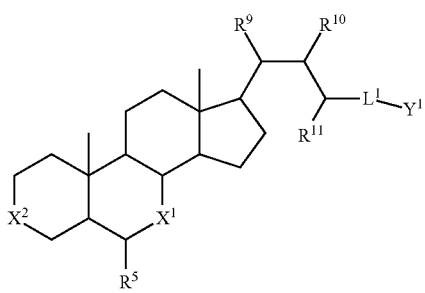

Embodiment 22. The complex of any one of embodiments 15 to 21, wherein $X^1$ is C(R$^1$)(R$^2$); and $X^2$ is C(R$^3$)(R$^4$).

Embodiment 23. The complex of embodiment 22 wherein said synthetic bile acid derivative has the formula:

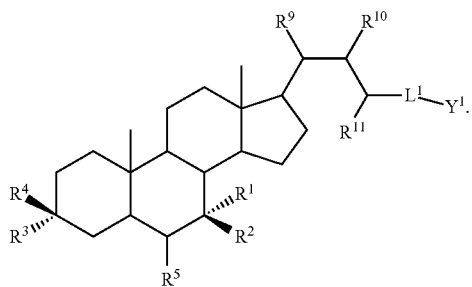

Embodiment 24. The complex of any one of embodiments 15 to 23, wherein R$^1$ and R$^2$ are hydrogen and R$^3$ is —OH.

Embodiment 25. The complex of any one of embodiments 15 to 23, wherein R$^1$ is —OH and R$^3$ is —OH.

Embodiment 26. The complex of any one of embodiments 15 to 21, wherein $X^1$ is C(O); and $X^2$ is C(O) or C(R$^3$)(R$^4$), and wherein R$^3$ is —OH.

Embodiment 27. The complex of any one of embodiments 15 to 21, wherein $X^1$ and $X^2$ are independently C(O).

Embodiment 28. The complex of any one of embodiments 15 to 27, wherein, $L^1$ is a bond or substituted or unsubstituted alkylene; $X^3$ is —C(O)NH-$L^2$-$R^2$, —C(O)O-$L^2$-$R^{12}$, or —C(O)-$L^2$-$R^{12}$; $L^2$ is independently substituted or unsubstituted alkylene; and $R^{12}$ is an acid moiety.

Embodiment 29. The complex of any one of embodiments 15 to 27, wherein, $L^1$ is a bond, substituted or unsubstituted alkylene; and $X^3$ is an acid moiety.

Embodiment 30. The complex of any one of embodiments 6 to 28, wherein said acid moiety forms a non-covalent bond with metformin.

Embodiment 31. The complex of any one of embodiments 6 to 27 and 29 to 30, wherein said acid moiety is —COOH or —SO$_3$H.

Embodiment 32. The complex of any one of embodiments 15 to 31, wherein said synthetic bile acid derivative has the formula:

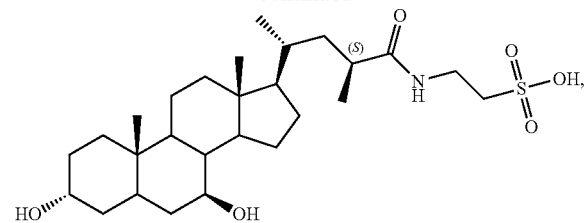

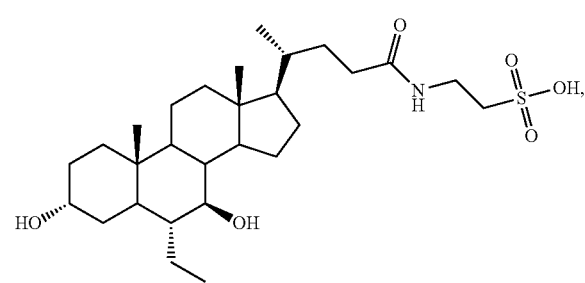

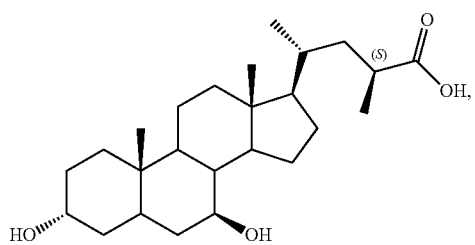

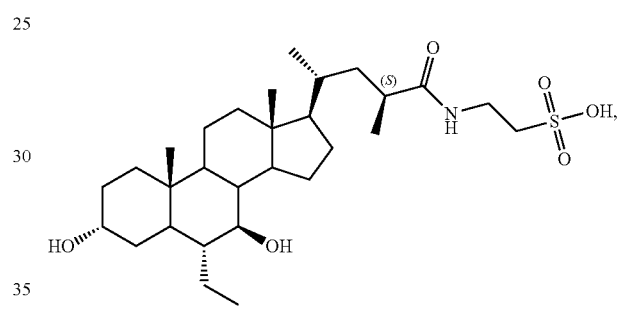

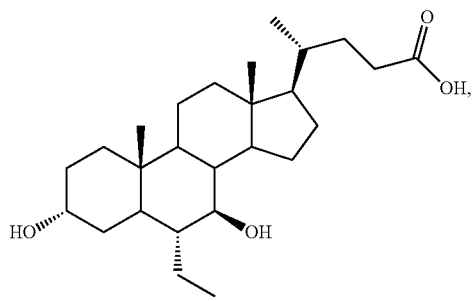

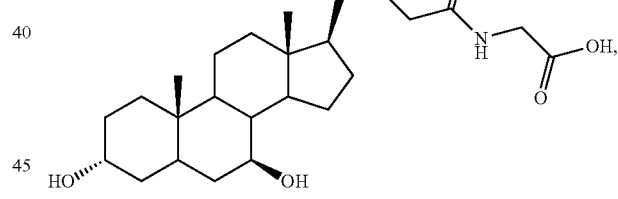

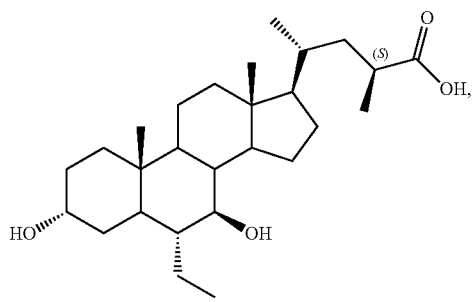

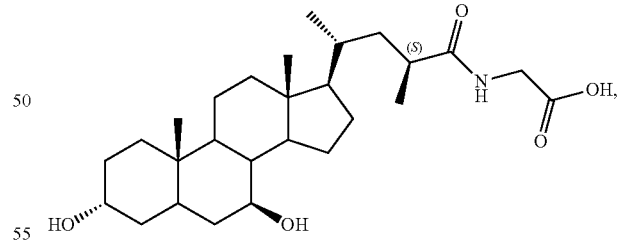

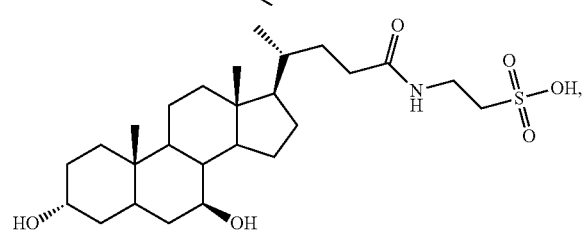

81

-continued

82

-continued

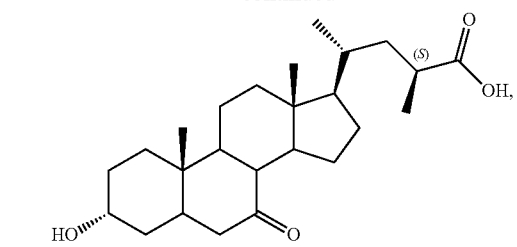

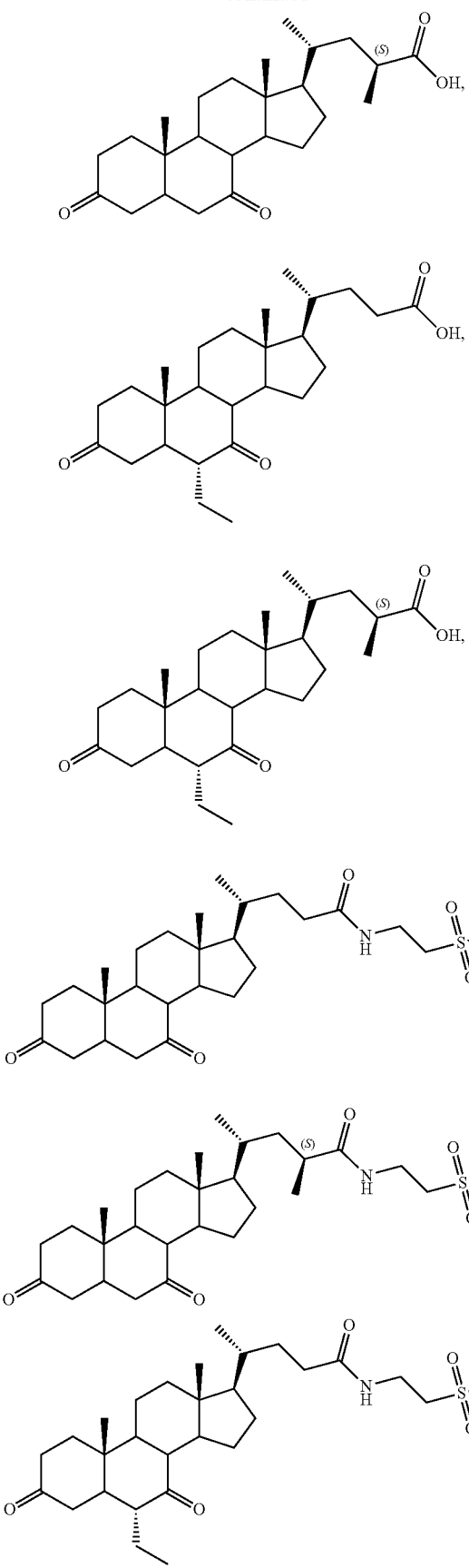
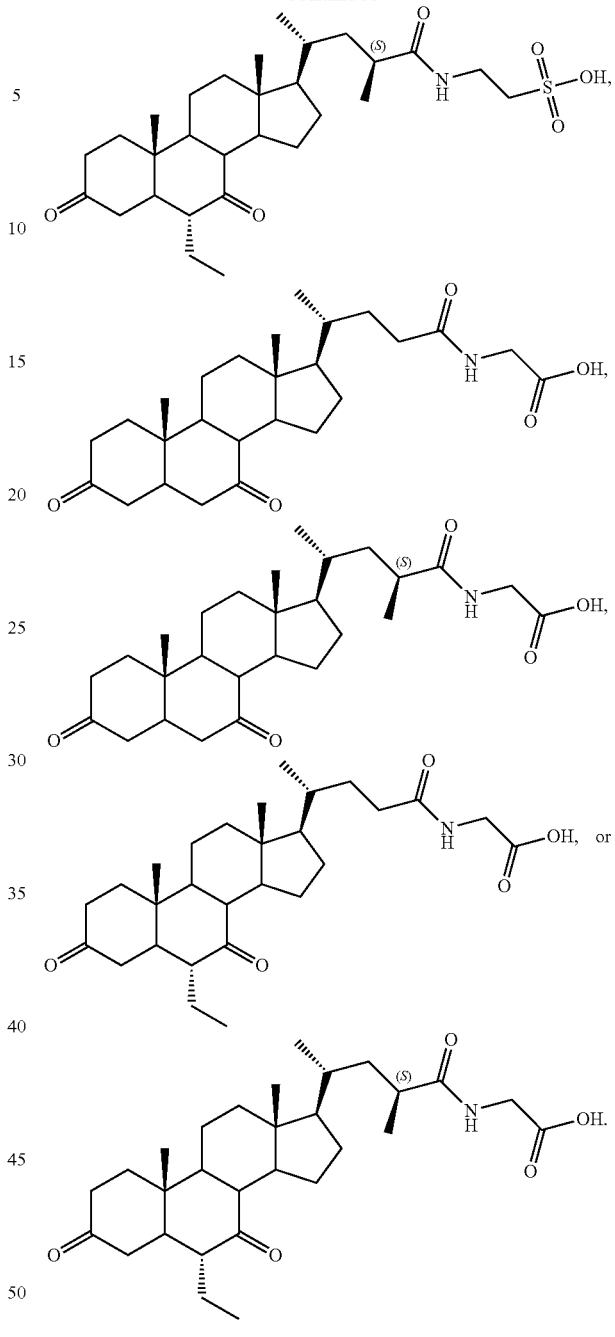

Embodiment 33. The complex of any one of embodiments 1 to 32, wherein said metformin or metformin analogue and said TGR5 ligand are present at a 1:1 molar ratio.

Embodiment 34. A pharmaceutical composition comprising: a metformin or a metformin analogue; a TGR5 ligand; and a pharmaceutically acceptable excipient.

Embodiment 35. The pharmaceutical composition of embodiment 34, wherein said metformin or metformin analogue and said TGR5 ligand form the complex of any one of embodiments 1 to 33

Embodiment 36. The pharmaceutical composition of embodiment 34 or 35, wherein said metformin or metformin analogue and said TGR5 ligand form a salt.

Embodiment 37. A method of treating cancer in a subject in need thereof, said method comprising administering a combined therapeutically effective amount of a metformin or metformin analogue and a TGR5 ligand.

Embodiment 38. The method of embodiment 37, wherein said cancer is colorectal cancer, gastric cancer, liver cancer, ovarian cancer, or breast cancer.

Embodiment 39. A method of treating diabetes in a subject in need thereof, said method comprising administering a combined therapeutically effective amount of a metformin or metformin analogue and a TGR5 ligand.

Embodiment 40. A method of treating a metabolic disease associated with diabetes in a subject in need thereof, said method comprising administering a combined therapeutically effective amount of a metformin or metformin analogue and a TGR5 ligand.

Embodiment 41. The method of embodiment 40, wherein said metabolic disease is hyperglycemia, insulin resistance, hyperinsulinemia, dyslipidemia, or hypertriglyceridemia.

Embodiment 42. A method of treating hyperglycemia in a subject in need thereof, said method comprising administering a combined therapeutically effective amount of a metformin or metformin analogue and a TGR5 ligand.

Embodiment 43. A method of treating insulin resistance in a subject in need thereof, said method comprising administering a combined therapeutically effective amount of a metformin or metformin analogue and a TGR5 ligand.

Embodiment 44. A method of treating hyperinsulinemia in a subject in need thereof, said method comprising administering a combined therapeutically effective amount of a metformin or metformin analogue and a TGR5 ligand.

Embodiment 45. A method of treating dyslipidemia in a subject in need thereof, said method comprising administering a combined therapeutically effective amount of a metformin or metformin analogue and a TGR5 ligand.

Embodiment 46. The method of embodiment 45, wherein said dyslipidemia is hyperlipidemia.

Embodiment 47. The method of embodiment 46, wherein said hyperlipidemia is hypercholesterolemia.

Embodiment 48. A method of treating hypertriglyceridemia in a subject in need thereof, said method comprising administering a combined therapeutically effective amount of a metformin or metformin analogue and a TGR5 ligand.

Embodiment 49. A method of treating hypertension in a subject in need thereof, said method comprising administering a combined therapeutically effective amount of a metformin or metformin analogue and a TGR5 ligand.

Embodiment 50. The method of embodiment 49, wherein said hypertension is arterial hypertension.

Embodiment 51. A method of treating fibrinolysis in a subject in need thereof, said method comprising administering a combined therapeutically effective amount of a metformin or metformin analogue and a TGR5 ligand.

Embodiment 52. A method of treating endothelial dysfunction in a subject in need thereof, said method comprising administering a combined therapeutically effective amount of a metformin or metformin analogue and a TGR5 ligand.

Embodiment 53. A method of reducing blood pressure in a subject in need thereof, said method comprising administering a combined therapeutically effective amount of a metformin or metformin analogue and a TGR5 ligand.

Embodiment 54. The method of embodiment 53, wherein said method reduces systolic or diastolic blood pressure in said subject.

Embodiment 55. A method of treating polycystic ovary syndrome in a subject in need thereof, said method comprising administering a combined therapeutically effective amount of a metformin or metformin analogue and a TGR5 ligand.

Embodiment 56. A method of treating cardiovascular disease in a subject in need thereof, said method comprising administering a combined therapeutically effective amount of a metformin or metformin analogue and a TGR5 ligand.

Embodiment 57. The method of embodiment 56, wherein said cardiovascular disease comprises coronary heart disease, atherosclerosis, myocardial infarction, or atherothrombosis.

Embodiment 58. The method of embodiment 56 or 57, wherein said cardiovascular disease is in a non-diabetic patient.

Embodiment 59. A method of decreasing glycated hemoglobin (HbA1c) in a subject in need thereof, said method comprising administering a combined therapeutically effective amount of a metformin or metformin analogue and a TGR5 ligand.

Embodiment 60. A method of reducing liver weight in a subject in need thereof, said method comprising administering a combined therapeutically effective amount of a metformin or metformin analogue and a TGR5 ligand.

Embodiment 61. A method of reducing kidney weight in a subject in need thereof, said method comprising administering a combined therapeutically effective amount of a metformin or metformin analogue and a TGR5 ligand.

Embodiment 62. The method of any one of embodiments 37 to 61, wherein said metformin or metformin analogue and said TGR5 ligand form the complex of any one of embodiments 1 to 33.

Embodiment 63. The method of any one of embodiments 37 to 62, wherein said metformin is present at an amount in said combined therapeutically effective amount of less than about 2500 mg.

Embodiment 64. The method of any one of embodiments 37 to 62, wherein said metformin is present at an amount in said combined therapeutically effective amount of less than about 1000 mg.

Embodiment 65. The method of any one of embodiments 37 to 62, wherein said metformin is present at an amount in said combined therapeutically effective amount of less than about 800 mg.

Embodiment 66. The method of any one of embodiments 37 to 62, wherein said metformin is present at an amount in said combined therapeutically effective amount of less than about 500 mg.

Embodiment 67. The method of any one of embodiments 37 to 62, wherein said metformin is present at an amount in said combined therapeutically effective amount of less than about 200 mg.

Embodiment 68. The method of any one of embodiments 37 to 62, wherein said metformin is present at an amount in said combined therapeutically effective amount of less than about 150 mg.

Embodiment 69. The method of any one of embodiments 37 to 62, wherein said metformin is present at an amount in said combined therapeutically effective amount of less than about 100 mg.

Embodiment 70. The method of any one of embodiments 37 to 62, wherein said metformin is present at an amount in said combined therapeutically effective amount of less than about 50 mg.

Embodiment 71. The method of any one of embodiments 37 to 62, wherein said metformin is present at an amount in said combined therapeutically effective amount of less than about 20 mg.

Embodiment 72. A kit comprising: i) a first pharmaceutical composition comprising a metformin or a metformin analogue and a pharmaceutically acceptable excipient; and ii) a second pharmaceutical composition comprising a TGR5 ligand and a pharmaceutically acceptable excipient.

Embodiment 73. A kit comprising a pharmaceutical composition comprising: i) a metformin or a metformin analogue; ii) a TGR5 ligand; and iii) a pharmaceutically acceptable excipient.

Embodiment 74. The kit of embodiment 72 or 73, wherein said metformin or metformin analogue and said TGR5 ligand form the complex of any one of embodiments 1 to 33.

Embodiment 75. The kit of embodiment 72 or 73, wherein said metformin is present at a therapeutically effective amount of less than about 2500 mg.

Embodiment 76. The kit of embodiment 72 or 73, wherein said metformin is present at a therapeutically effective amount of less than about 1000 mg.

Embodiment 77. The kit of embodiment 72 or 73, wherein said metformin is present at a therapeutically effective amount of less than about 800 mg.

Embodiment 78. The kit of embodiment 72 or 73, wherein said metformin is present at a therapeutically effective amount of less than about 500 mg.

Embodiment 79. The kit of embodiment 72 or 73, wherein said metformin is present at a therapeutically effective amount of less than about 200 mg.

Embodiment 80. The kit of embodiment 72 or 73, wherein said metformin is present at a therapeutically effective amount of less than about 150 mg.

Embodiment 81. The kit of embodiment 72 or 73, wherein said metformin is present at a therapeutically effective amount of less than about 100 mg.

Embodiment 82. The kit of embodiment 72 or 73, wherein said metformin is present at a therapeutically effective amount of less than about 50 mg.

Embodiment 83. The kit of embodiment 72 or 73, wherein said metformin is present at a therapeutically effective amount of less than about 20 mg.

What is claimed is:

1. A complex of the following structure:

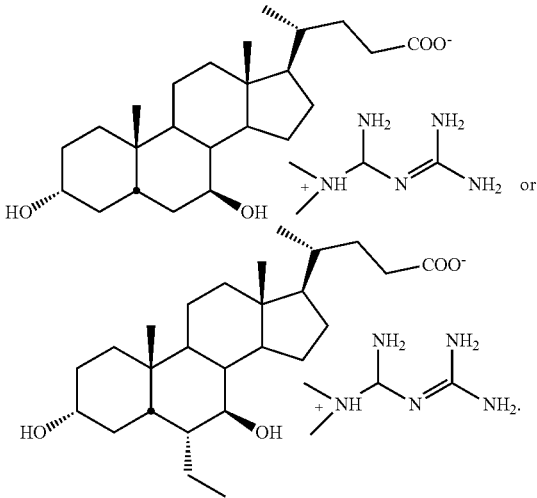

2. A pharmaceutical composition comprising the complex of claim 1, and a pharmaceutically acceptable excipient.

3. A method of treating a disease or disorder in a subject in need thereof, said method comprising administering a therapeutically effective amount of the complex of claim 1 to said subject, wherein said disease or disorder is colorectal cancer, gastric cancer, liver cancer, ovarian cancer, or breast cancer.

4. A method of treating a disease or disorder in a subject in need thereof, said method comprising administering a therapeutically effective amount of the complex of claim 1 to said subject, wherein said disease or disorder is diabetes, a metabolic disease, hypertension, fibrinolysis, endothelial dysfunction, polycystic ovary syndrome, coronary heart disease, atherosclerosis, myocardial infarction, atherothrombosis, or fatty liver disease.

5. The method of claim 4, wherein said metabolic disease is hyperglycemia, insulin resistance, hyperinsulinemia, dyslipidemia, or hypertriglyceridemia.

6. The method of claim 3, wherein the treating comprises reducing blood pressure, decreasing glycated hemoglobin (HbA1c), reducing liver weight or reducing kidney weight.

7. The method of claim 4, wherein said fatty liver disease is nonalcoholic fatty liver disease.

* * * * *